(12) United States Patent
Carbonell et al.

(10) Patent No.: US 7,408,030 B2
(45) Date of Patent: Aug. 5, 2008

(54) PURIFICATION OF IMMUNOGLOBULINS USING AFFINITY CHROMATOGRAPHY AND PEPTIDE LIGANDS

(75) Inventors: Ruben Carbonell, Raleigh, NC (US); Haiou Yang, Raleigh, NC (US); Patrick Gurgel, Cary, NC (US)

(73) Assignee: North Carolina State University, Raleigh, NC (US)

( * ) Notice: Subject to any disclaimer, the term of this patent is extended or adjusted under 35 U.S.C. 154(b) by 366 days.

(21) Appl. No.: 11/035,016

(22) Filed: Jan. 13, 2005

(65) Prior Publication Data
US 2006/0153834 A1 Jul. 13, 2006

(51) Int. Cl.
*C07K 7/06* (2006.01)
*C07K 1/22* (2006.01)
(52) U.S. Cl. ...................... 530/329; 530/413
(58) Field of Classification Search ................ 530/329, 530/413; 435/DIG. 35; 436/824
See application file for complete search history.

(56) References Cited

U.S. PATENT DOCUMENTS

| | | | | |
|---|---|---|---|---|
| 4,631,211 | A * | 12/1986 | Houghten | 428/35.5 |
| 5,834,318 | A | 11/1998 | Buettner | |
| 6,207,807 | B1 | 3/2001 | Fassina et al. | |
| 2006/0088895 | A1 * | 4/2006 | Wanders et al. | 435/7.32 |
| 2006/0153834 | A1 * | 7/2006 | Carbonell et al. | 424/133.1 |

OTHER PUBLICATIONS

Wang et al, Journal of Peptide Research, 64, 51-64, 2004.*
Tosoh Bioscience product catalog, "Affinity Chromatography" (no date), cover and pp. 38-42. Tosoh Bioscience, Montgomeryville, PA.
Kato Y, et al., "High-performance metal chelate affinity chromatography of proteins," Journal of Chromatography (1986) vol. 354, pp. 511-517.
Gurgel P V, et al., "Identification of peptide ligands generated by combinatorial chemistry that bind alpha-lactalburnin," Separation Science and Technology (2001), vol. 36(11), pp. 2411-2431, Marcel Dekker, Inc., NY, NY.

* cited by examiner

*Primary Examiner*—David A Saunders
(74) *Attorney, Agent, or Firm*—Myers Bigel Sibley & Sajovec, P.A.

(57) ABSTRACT

An immunoglobulin binding peptide having the general formula, from amino terminus to carboxy terminus, of $Z\text{-}R^1\text{—}R^2\text{—}R^3\text{—}R^4\text{—}R^5\text{—}R^6\text{—}X$, is described, wherein: $R^1$ is H or Y; $R^2$ is a hydrophobic, preferentially aromatic, amino acid (for example W, F, Y, V); $R^3$ is a positively charged or aromatic amino acid (for example R, H, F, W); $R^4$ is a hydrophobic or positively charged amino acid (for example G, Y, R, K, L); $R^5$ is a positively charged or aromatic amino acid (for example W, F, R, H, Y); $R^6$ a random amino acid but preferably hydrophobic or negatively charged (for example V, W, L, D, H); X is present or absent and when present is a linking group; and Z is present or absent and when present is a capping group bonded to the N terminus of $R^1$; and wherein the amino acids of said peptide are in D form, L form, or a combination thereof. Methods of using such peptides for the purification of Immunoglobulins are also described.

33 Claims, 26 Drawing Sheets

R = Hydrophilic polymer
Ligand = $X_6X_5X_4X_3X_2X_1$

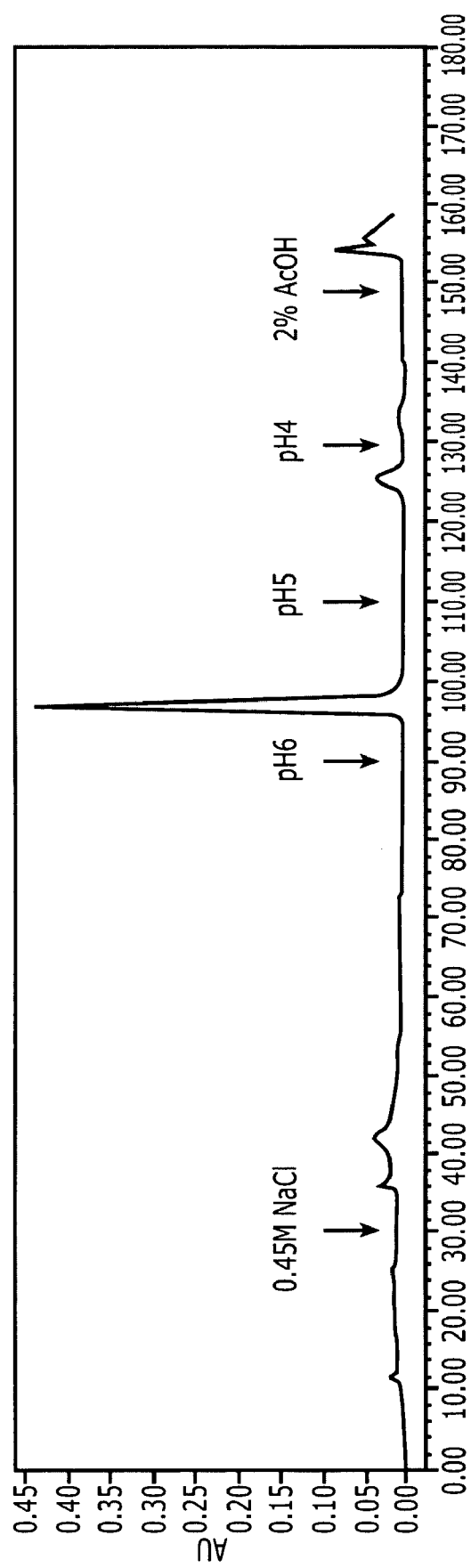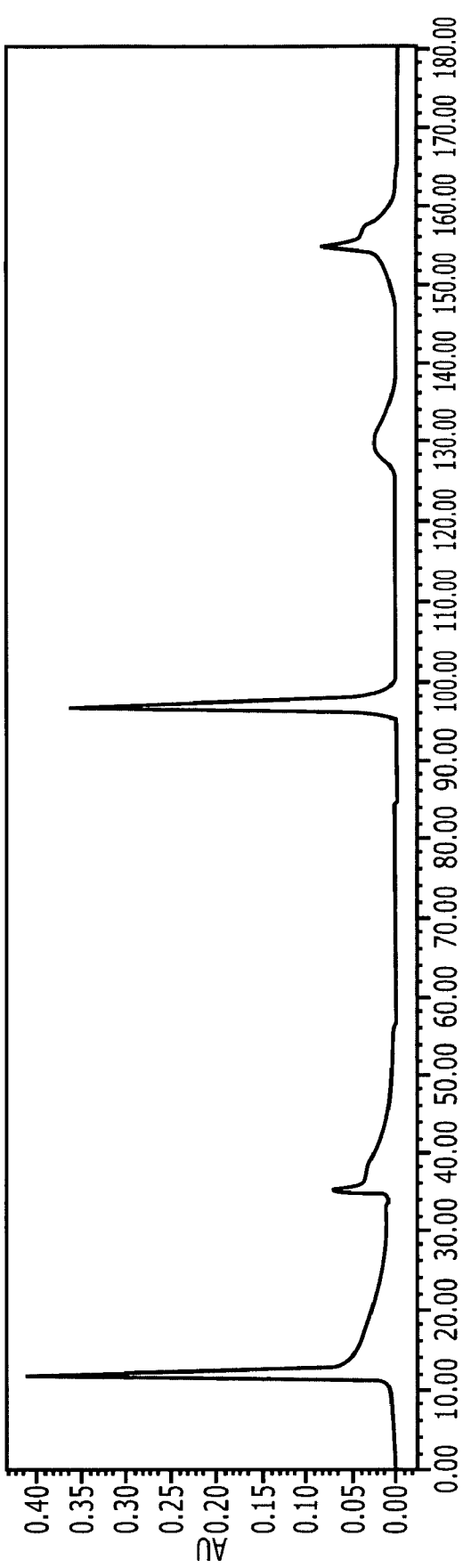
FIGURE 11a
FIGURE 11b

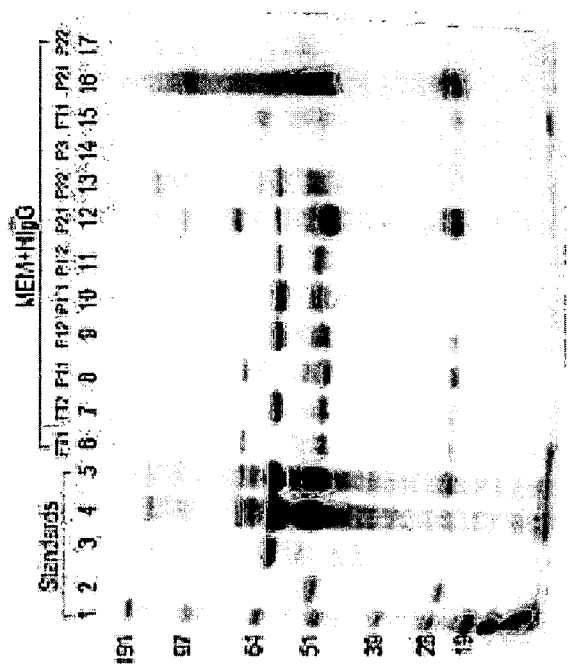
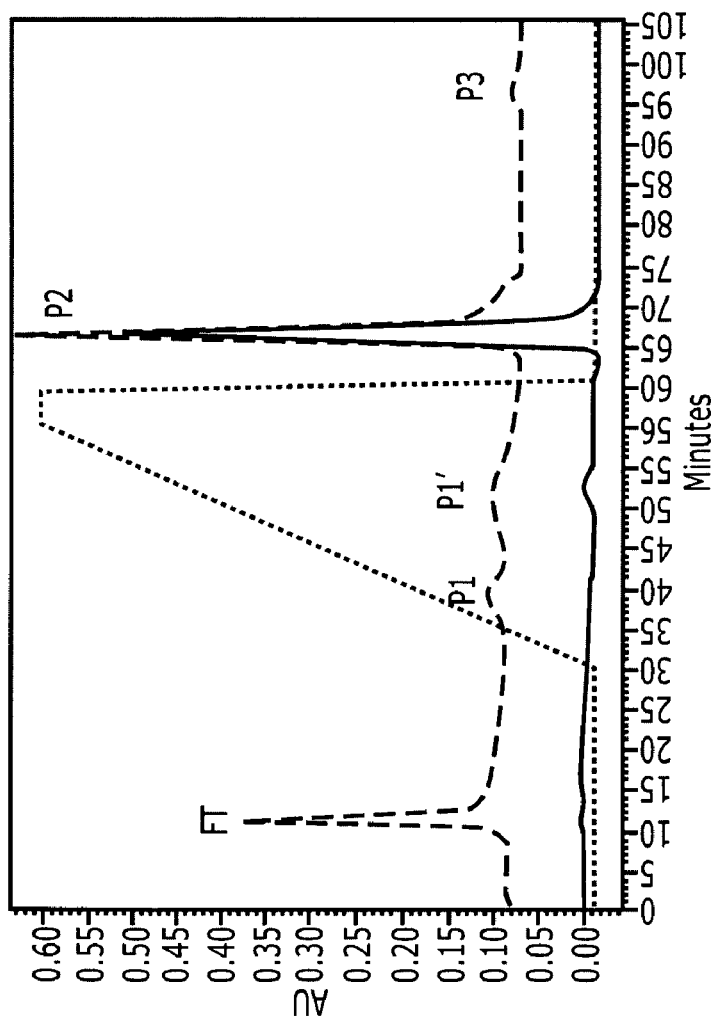
FIGURE 17b
FIGURE 17a

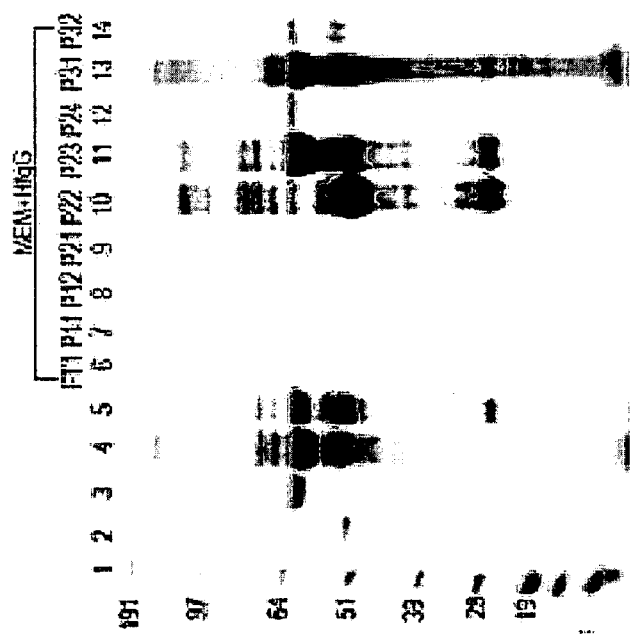
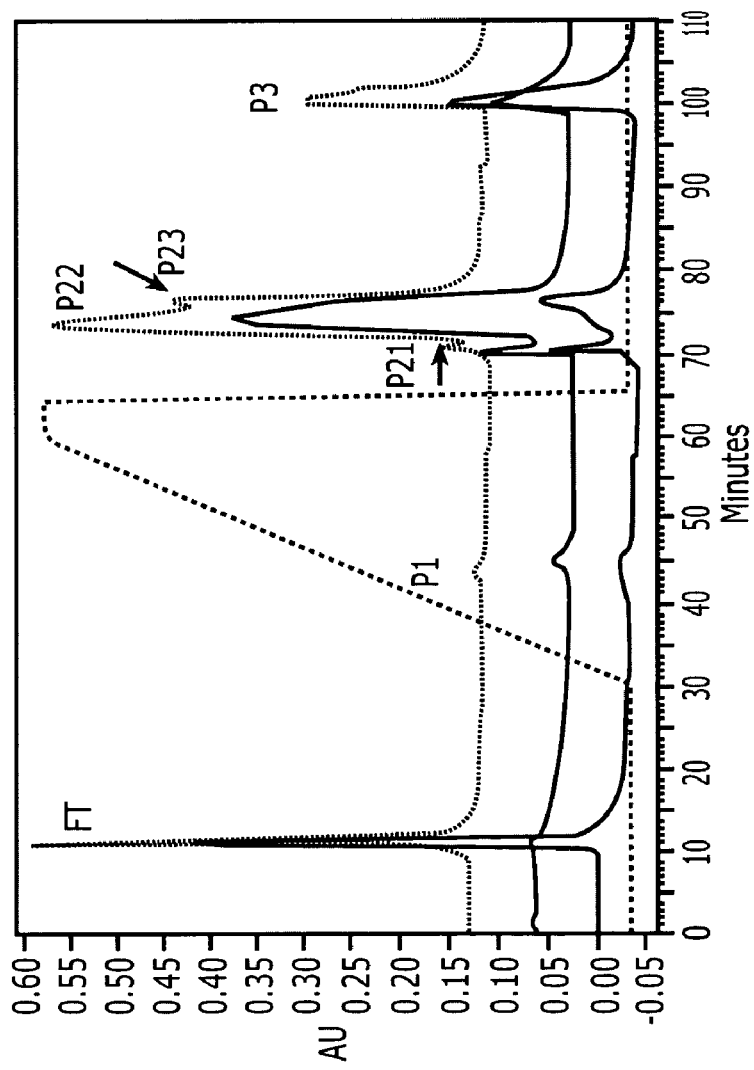
FIGURE 20b
FIGURE 20a

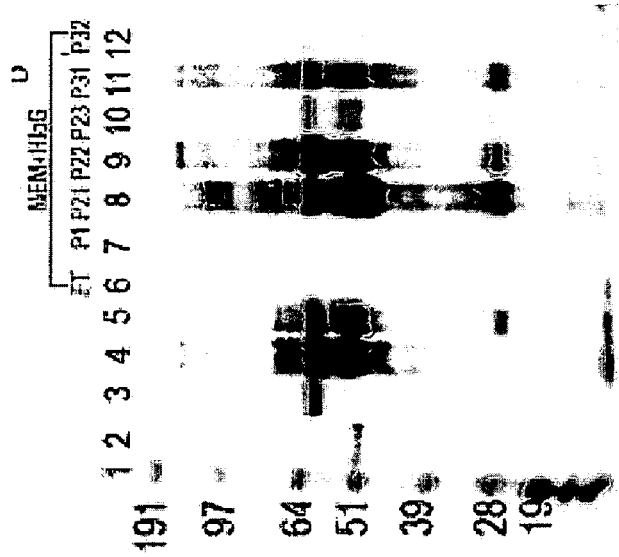
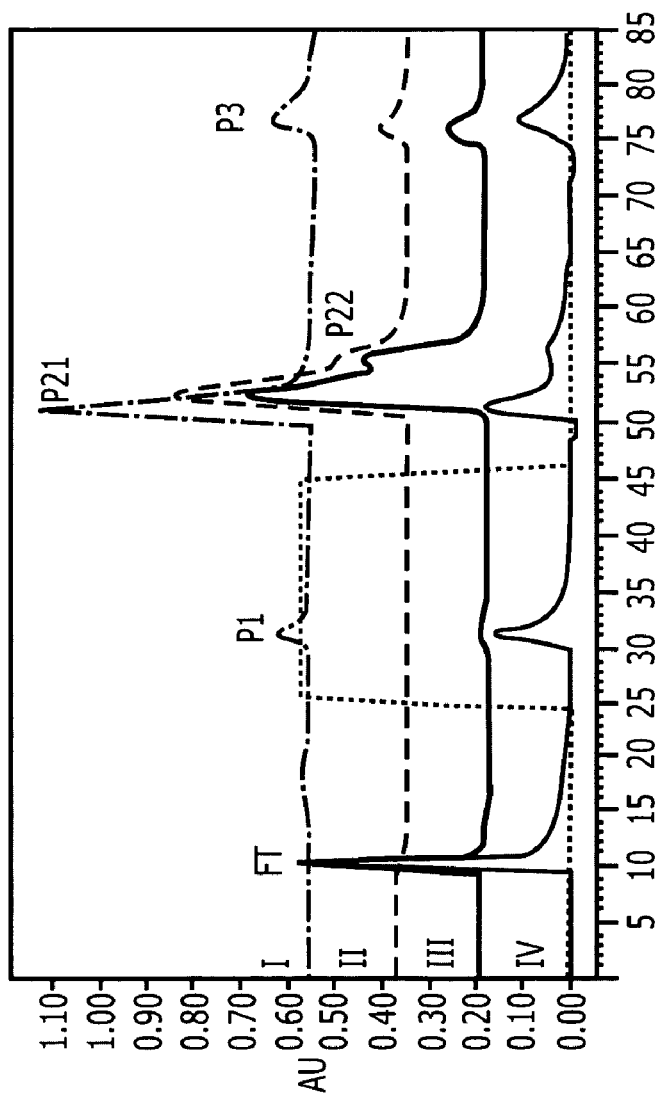
FIGURE 21b
FIGURE 21a

PURIFICATION OF IMMUNOGLOBULINS USING AFFINITY CHROMATOGRAPHY AND PEPTIDE LIGANDS

FIELD OF THE INVENTION

This invention concerns the making and use of peptide ligands for the purification of immunoglobulins from liquid containing immunoglobulins such as blood or blood plasma, plasma fractions, ascites fluid, aqueous cell culture, milk, and colostrums.

BACKGROUND OF THE INVENTION

The human immunoglobulins (Igs), a class of plasma proteins produced by the immune system as a response to parasitic invasion, can be divided into five classes, IgG, IgA, IgM, IgD, and IgE. Human IgG (HIgG) has an average concentration of 12 mg/ml in adult blood, and encompasses 75% of all human immunoglobulins. HIgG consists of four subclasses IgG1, 2, 3, and 4. Among these subclasses, IgG1 is the most dominant protein, making up anywhere between 43 to 75% of all the HIgG (J. Harris, *Blood Separation and Plasma Fractionation*, John Wiley & Sons, New York, 325p (1990)). The HIgG backbone consists of two identical "heavy" chains and two identical "light" chains (FIG. 1). Disulfide bonds form bridges between chains, which confer flexibility to the HIgG molecule.

HIgG is usually obtained from pooled plasma by the Cohn-Oncley process, which needs at least 4 steps to achieve an IgG purity of 85%. HIgG isolated by this technique tends to aggregate to form multimers (J. Harris, *Blood Separation and Plasma Fractionation*, John Wiley & Sons, New York, 325p (1990)). Monoclonal antibodies produced in cell culture from hybridoma cells is another source for the production of HIgG. Diafiltered supernatant of cell culture can be subjected to different processes, such as ammonium sulfate precipitation, ion-exchange chromatography (IEC), hydrophobic interaction chromatography (HIC), or affinity chromatography (J. Harris, *Blood separation and plasma fractionation*, New York: A John Wiley & Sons 325 p. (1990)) to purify HIgG. Ion exchange chromatography (R. Necina et al., *Biotechnology and Bioengineering* 60(6):689-698 (1998)) has been used to purify HIgG directly from cell culture supernatant containing 3% fetal calf serum (FCS) yielding a recovery of less than 70% and a HIgG:BSA ratio of 1:2. Ammonium sulfate precipitation generated even less purity than ion-exchange chromatography (J. Harris, *Blood separation and plasma fractionation*, New York: A John Wiley & Sons. 325 p. (1990)). Pretreatment of the cell culture supernatant is necessary prior to using HIC, due to the high salt concentration usually found in the supernatant. Hydrophobic charge induction chromatography (HCIC) (L. Guerrier, et al., *Journal of Chromatography* B 755(1-2):37-46 (2001); L. Guerrier, et al., *Bioseparation* 9(4):211-221 (2000)) can be another choice of HIgG purification, yielding a purity of 98% when the feedstock solution was from protein-free cell culture supernatant. However, when dealing with cell culture supernatant containing 5% FCS, an IEC step had to be coupled to HCIC, and the purity and recovery of HIgG were found to be 69% and 76% respectively.

Among the chromatographic methods, affinity chromatography deserves particular attention because, in principle, it allows the possibility of obtaining several fold purification with high recovery in a single step. Protein A and protein G are the most commonly used ligands in the purification of HIgG. However, several drawbacks, including their high cost, low stability, and the possibility of contaminating products, make it important to find a new ligand for IgG purification. Synthetic small ligands may overcome some of these disadvantages and have been studied by many research groups. Table 1, below, lists small ligands that have been used in HIgG affinity purification.

Table 1. Small ligands used in the purification of IgG.

TABLE 1

Small ligands used in the purification of IgG.

| | Company | Ligand | Support | Capacity | IgG Source | Elution | Purity/Recovery |
|---|---|---|---|---|---|---|---|
| 1. | Chinese Academy of Sciences, China | sulfamethazine | Poly(glycidyl methacrylate) | | HBP | 0.05M PBS, 0.25 NaCl, pH 5.5 | 90%/ |
| 2. | HoffmannLaRoche Inc. USA | EPIHRSTLTALL (SEQ ID NO:35) | Amino-NuGel | 320 µg/g gel | Culture | 0.2M NaCl/0.2M HOAc | |
| 3. | Research Institute for Green Technology, Japan | Mannosylerythritol lipid | Poly(2-hydroxyethyl methacrylate) | 106 mg/g gel | | 0.1M Acetate buffer, pH 3.6 | /80% |
| 4. | Tecnogen SCpA, Biopharmaceuticals, Italy | MAP AV13: GFRKYLHFRRHLL (SEQ ID NO:33) (AV13)$_4$K$_2$KG (SEQ ID NO:36) AV15: VRLGWLLAPADLDAR (SEQ ID NO:37) (AV15)$_4$(KRG)$_2$KG (SEQ ID NO:38) | Epoxy-activated Eupergif C30N | | Anti-MAP sera | 0.1M acetic acid | |
| 5. | Tecnogen, Italy | TG19318 (PAM): (RTY)$_4$K$_2$KG (SEQ ID NO:39) | Epoxy-activated Eupergif C30N | 25 mg/ml gel | | 0.1M acetic acid | |
| 6. | Tecnogen, Italy | D-PAM, TG19320: KAPTIV-GY (SEQ ID NO:40) | Poly-acrylamide/azlactone-activated gel (Emphaze matrix) | | Serum | 0.1M acetic acid, pH 3.5 | 95%/ |
| 7. | Amersham Biosciences | Protein A | 4% Cross-link agarose | 20 mg/ml moist gel | | 0.1M citrate acid, pH 3.0 | |

TABLE 1-continued

Small ligands used in the purification of IgG.

| Company | Ligand | Support | Capacity | IgG Source | Elution | Purity/Recovery |
|---|---|---|---|---|---|---|
| 8. Amersham Biosciences | Protein G | Sepharose high performance | | | 0.1M Gly, pH 2.7 | |
| 9. Prometic Biosciences Ltd. | MAbsorbent A1P/A2P | 6% Cross-link agarose | 50 mg/ml resin | | 10/50 mM citrate buffer, pH 3.0 | |
| 10. University of Cambridge, UK | 22/8: Aromatic amines | Sepharose 6B | 51.9 g/g moist gel | HBP | 0.1M glycine-HCl, pH 2.9 (0.025M citric acid, pH 2.4) | 97.3/67% |
| 11. Hacettepe University, Turkey | Transition Metal ions | Poly(hydroxyethyl methacrylate) | | | 50 mM ethylenediaminetetraacetic acid (EDTA), pH 8.0 | |

SUMMARY OF THE INVENTION

A first aspect of the invention is an immunoglobulin binding peptide having the general formula, from amino terminus to carboxy terminus, of

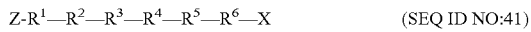   (SEQ ID NO:41)

wherein:

$R^1$ is H or Y;

$R^2$ is a hydrophobic, preferentially aromatic, amino acid (for example W, F, Y, V);

$R^3$ is a positively charged or aromatic amino acid (for example R, H, F, W);

$R^4$ is a hydrophobic or positively charged amino acid (for example G, Y, R, K, L);

$R^5$ is a positively charged or aromatic amino acid (for example W, F, R, H, Y);

$R^6$ a random amino acid but preferably hydrophobic or negatively charged (for example V, W, L, D, H);

X is present or absent and when present is a linking group; and

Z is present or absent and when present is a capping group bonded to the N terminus of $R^1$;

and wherein the amino acids of said peptide are in D form, L form, or a combination thereof.

In some embodiments of the foregoing, the peptide is preferably not not YYWLHH (SEQ ID NO: 8).

A further aspect of the invention is a solid support having an immunoglobulin binding peptide as described above immobilized thereon.

A further aspect of the invention is a method of binding an immunoglobulin, comprising: (a) providing a binding peptide as described herein; (b) contacting a composition containing an immunoglobulin to said binding peptide; and then (c) separating the binding peptide from the composition, with the immunoglobulin bound to the binding peptide.

A still further aspect of the invention is a method of identifying small peptide ligands with high affinity for immunoglobulins of interest, the method comprising the steps of: (a) screening a library of peptides, wherein the peptides are attached to a solid support, and wherein the peptides consist essentially of from 5 to 7 amino acid residues; (b) contacting a labeled immunoglobulin or labeled fragment thereof to the peptides; and then (c) determining the identity of the peptides bound to the the labeled immunoglobulin or fragment thereof.

The present invention is explained in greater detail in the following non-limiting Examples.

BRIEF DESCRIPTION OF THE DRAWINGS

FIG. 11. Effect of pH value of elution buffer on separation of HIgG from MEM. 0-30 minutes: PBS with 0.138 M NaCl, pH 7.4 loading buffer; 30-45 minutes: PBS with 0.45M NaCl; 45-90 minutes: increasing salt concentration in PBS to 1M; 90-110 minutes: pH 6 phosphate buffer; 110-130 minutes: pH 5 phosphate buffer; 130-150: pH 4 phosphate buffer; after 150 minutes: cleaning column using 2% acetic acid. (a) Pure HIgG at 5 mg/ml in PBS; (b) MEM with 5 mg/ml HIgG.

FIG. 17. Separation of HIgG from MEM on the HYFKFD (SEQ ID NO: 11) column. Samples were loaded in PBS at pH 7.4, washed with 0.14-1.14 M NaCl linear gradient for 30 minutes from 30-60 minutes. HIgG was eluted at about 70 minutes with PB at pH 4, and from 95 min the column was cleaned with 2% acetic acid. The flow rate was 0.4 ml/min. (a) Chromatogram of 5 mg/ml HIgG on HYFKFD (SEQ ID NO: 11). Dashed line: 5 mg/ml HIgG in MEM; solid line: 5 mg/ml HIgG in PBS. (b) Coomassie blue stained SDS-PAGE of the separation denoted in (a). Lane 1: molecular marker; lane 2: HIgG standard; lane 3: BSA standard; lane 4: 20% MEM; lane 5: 1:50 dilution of loading material (MEM+HIgG); lanes 6-14 correspond to the flow through, peaks 1, 1', 2, and 3 of injections, respectively. FT2, P12, P1'2 and P22 are the tails of peaks of FT, P1, P1' and P2. Lanes 1-14 are under reducing condition. Lanes 15-17 are under non-reducing condition (no reducing agent in sample preparation). P21 (lane 12) is the eluted HIgG peak in pH 4 PB.

FIG. 20. Separation of HIgG from MEM on the YYWLHH (SEQ ID NO: 8) column. Samples were loaded in PBS at pH 7.4, washed with 0.14-1.14 M NaCl linear gradient for 30 minutes from 30-60 minutes. HIgG was eluted at about 70 minutes with PB at pH 4, and from 95 min the column was cleaned with 2% acetic acid. The flow rate was 0.4 ml/min. (a) Chromatograms of samples on YYWLHH (SEQ ID NO: 8). Dotted line: 5 mg/ml HIgG in MEM; dashed line: 5 mg/ml HIgG in PBS; solid line: MEM. (b) Coomassie blue stained SDS-PAGE gel of, under reducing condition, the separation denoted in (a). Lane 1: molecular marker; lane 2: HIgG standard; lane 3: BSA standard; lane 4: 20% MEM; lane 5: 1:50 dilution of loading material (MEM+HIgG); lanes 6-14 correspond to the flow through, peaks 1, 2, and 3 of HIgG+MEM injection, respectively. FT2 and P22 are the tails of peaks of FT and P2. P12, P24, and P32 are the tails of peaks of P1, P23 and P3. P22 (lane 10) is the eluted HIgG peak in pH 4 PB.

Figure 1:
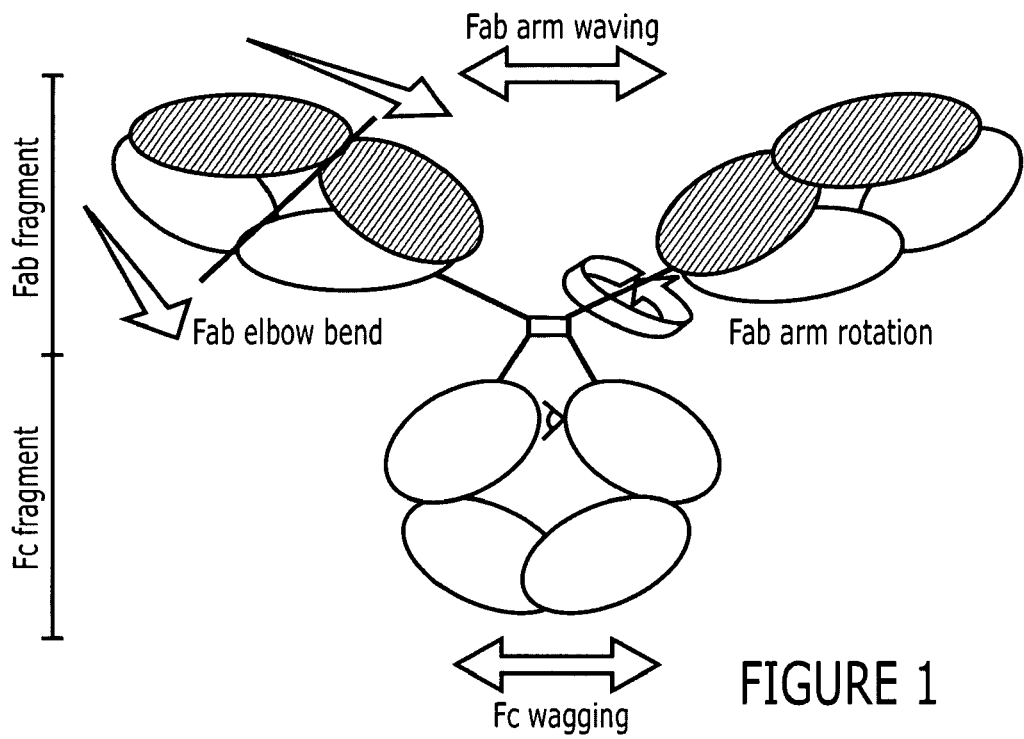
FIG. 1. Structure and flexibility of HIgG (Breckke et al., *Immunology Today* 16(2): 85-90 (1995)).

FIG. 21. Comparison of two substitutions of HWRGWV (SEQ ID NO:4) to separate HIgG from MEM using pH 4 PB. Samples were loaded in PBS at pH 7.4, washed with 0.5 M NaCl for 20 minutes from 25-45 minutes. HIgG was eluted at about 50 minutes with PB at pH 4, and the column was cleaned with 2% acetic acid. The flow rate was 0.4 ml/min. (a) Chromatogram of 5 mg/ml HIgG on HWRGWV. Line I: 5 mg/ml HIgG in PBS on 0.1 meq/g HWRGWV (SEQ ID NO: 4) column; line II: 5 mg/ml HIgG in PBS on 0.55 meq/g HWRGWV column; line III: 5 mg/ml HIgG in MEM on 0.55 meq/g HWRGWV (SEQ ID NO: 4) column; line IV: 5 mg/ml HIgG in MEM on 0.1 meq/g HWRGWV (SEQ ID NO: 4) column; (b) SDSPAGE gel of the separation on 0.55 meq/g HWRGWV. Lane 1: molecular marker; lane 2: HIgG standard; lane 3: BSA standard; lane 4: 20% MEM; lane 5: 1:50 dilution of loading material (MEM+HIgG); lanes 6-12 correspond to the flow through, peaks 1, 21, 22 and 3 of MEM+ HIgG injection, respectively. P23 and P32 are the tails of peaks P21, and P31. P21 (lane 8) is the eluted HIgG peak in pH 4 PB. The volumes of the collected peaks were adjusted to same. The gel was run under reducing condition.

Figure 22A:
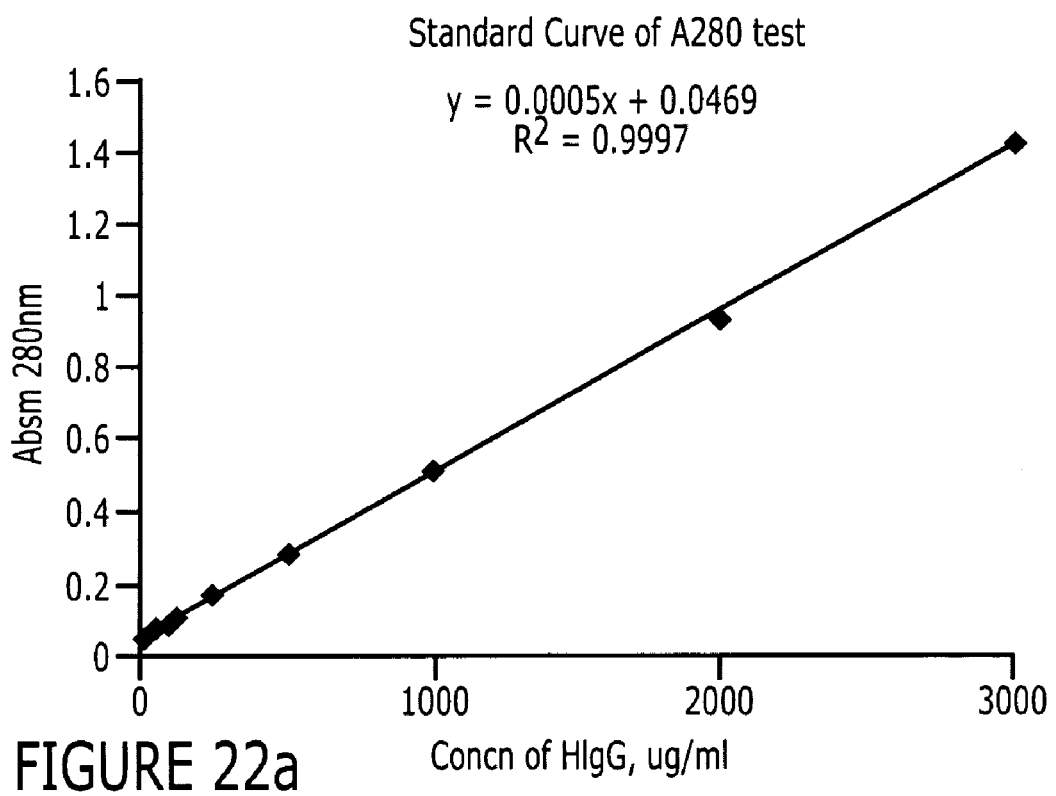
Figure 22B:
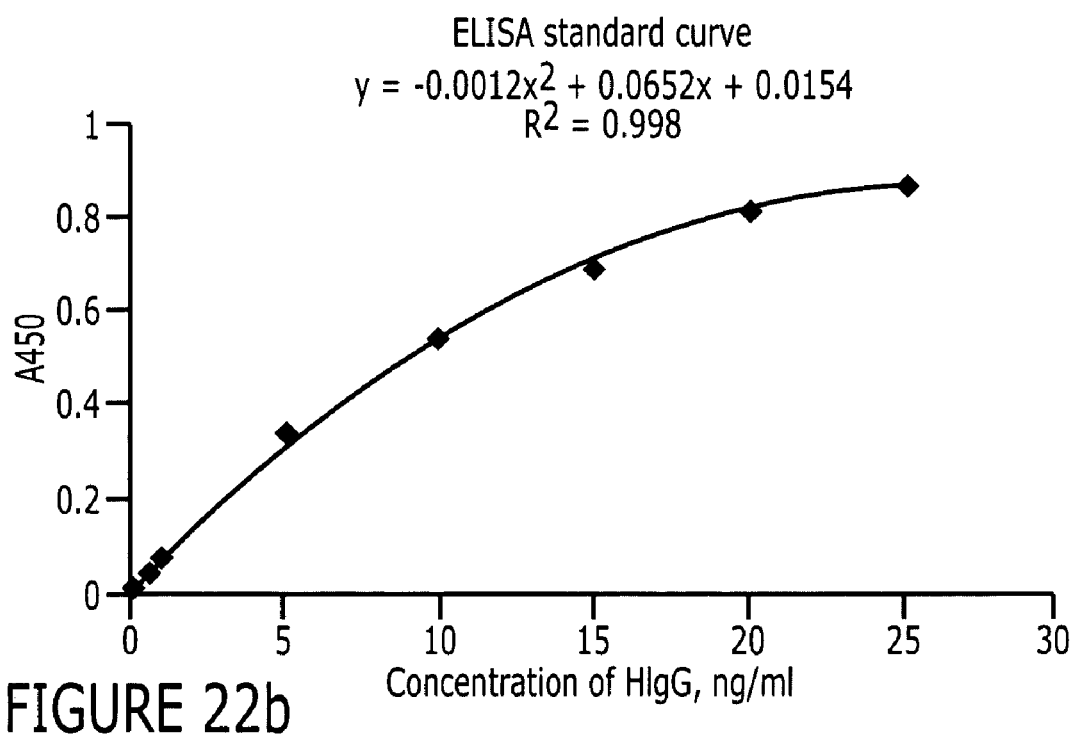

FIG. 22. Standard curve of total protein assay (a) and enzyme-linked immunosorbent assay (ELISA) for HIgG (b). In ELISA assay, the standard samples were incubated for 2 hours at room temperature on an orbital shaker at 600 rpm.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The disclosures of all United States patents cited herein are to be incorporated herein by reference in their entirety.

A. Definitions.

"Antibody" or "antibodies" "Antibodies" as used herein refers to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. Of these immunoglobulins, IgM and IgG are preferred, and IgG is particularly preferred. The antibodies may be of any species of origin, including (for example) mouse, rat, rabbit, horse, or human, or may be chimeric antibodies. The term "antibody" as used herein includes antibody fragments which retain the capability of binding to a target antigen or receptor, for example, Fab, $F(ab')_2$, Fc and Fv fragments, and the corresponding fragments obtained from antibodies other than IgG. Such fragments are also produced by known techniques.

"Composition" as used herein refers to a liquid containing at least one immunoglobulin, which is sought to be purified from other substances also present. Compositions are often complex mixtures or solutions containing many biological molecules such as proteins, antibodies, hormones and viruses as well as small molecules such as salts, sugars, and lipids. Examples of compositions that may include immunoglobulins of interest include, but are not limited to, blood or blood plasma, plasma fractions, ascites fluid, aqueous cell culture, milk, and colostrums.

"Label" or "detectable group" as used herein may be any suitable label or detectable group detectable by spectroscopic, photochemical, biochemical, immunochemical, electrical, optical or chemical means including but not limited to biotin, fluorophores, antigens, porphyrins, and radioactive isotopes. Labels useful in the present invention include biotin for staining with labeled avidin or streptavidin conjugate, magnetic beads (e.g., Dynabeads™), fluorescent dyes (e.g., fluorescein, fluorescein-isothiocyanate [FITC], Texas red, rhodamine, green fluorescent protein, enhanced green fluorescent protein, lissamine, phycoerythrin, Cy2, Cy3, Cy3.5, Cy5, Cy5.5, Cy7, Fluor X [Amersham], SyBR Green I & II [Molecular Probes], and the like), radiolabels (e.g., $^3H$, $^{35}S$, $^{14}C$, or $^{32}P$), enzymes (e.g., hydrolases, particularly phosphatases such as alkaline phosphatase, esterases and glycosidases, or oxidoreductases, particularly peroxidases such as horseradish peroxidase, and the like), substrates, cofactors, inhibitors, chemiluminescent groups, chromogenic agents, and colorimetric labels such as colloidal gold or colored glass or plastic (e.g., polystyrene, polypropylene, latex, etc.) beads.

"Ligand" as used herein refers to a molecule or group of molecules that bind to one or more specific sites of a receptor.

"Solid support" or "solid phase support" as used herein refers to an inert material or molecule to which a peptide ligand may be bound or coupled, either directly or indirectly through a linking group. The solid phase support is suitable for use in column chromatography or other types of purification.

"Alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkenyl," as used herein, refers to a straight or branched chain hydrocarbon containing from 2 to 10 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

"Lower alkenyl" as used herein, is a subset of alkenyl and refers to a straight or branched chain hydrocarbon group containing from 1 to 4 carbon atoms.

"Alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkyl and refers to a straight or branched chain hydrocarbon group containing from 1 to 4 carbon atoms.

The alkyl, alkenyl, and alkynyl groups of the invention can be substituted or unsubstituted and are either unless otherwise specified. When substituted the alkyl, alkenyl or alkynyl groups of the invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, "Aryl" as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 or more substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, "Arylalkyl," as used herein, refers to an aryl group, as defined herein, appended to the parent molecular moiety through an alkenyl group, as defined herein. Representative examples of arylalkenyl include, but are not limited to, 2-phenylethenyl, 3-phenylpropen-2-yl, 2-naphth-2-ylethenyl, and the like, which may be substituted or unsubstituted as noted above.

B. Peptides.

The peptides of the present invention have the general formula, from amino terminus to carboxy terminus, of Z-R'—$R^2$—$R^3$—$R^4$—$R^5$—$R^5$—X (SEQ ID NO:41), where $R^1$ is H, $R^2$ is W, F, Y or V, $R^3$ is R, H, F, or W, $R^4$ is G, Y, R or K, $R^5$ is W, F, R or H and $R^6$ is V, W, L or D. X may or may not be present but when present it is from 1-10 additional amino acids. Z may or may not be present but when present it is a capping group bonded to the N terminus of $R^1$. Furthermore, the amino acids of said peptide may be in D form, L form, or a combination thereof. (The single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr))

Specific examples of the peptides of this invention include, but are not limited to, HWRGWV (SEQ ID NO: 4), HYFKFD (SEQ ID NO: 11), HFRRHL (SEQ ID NO: 21), HVHYYW (SEQ ID NO: 12) and YYWLHH (SEQ ID NO: 8). These peptides may or may not have linking groups bonded to the carboxy terminus. Linking groups as used herein are described in more detail below. Furthermore, peptides of this invention may or may not have capping groups bonded to the amino terminus. When present the capping groups may consist of such groups as $R^{10}CO$—, $R^{10}$—O—CO—, $R^{10}$—PO—, $R^{10}$—$SO_2$— and arylalkyl-; where $R^{10}$ is selected from the group consisting of H, alkyl, alkenyl, alkynyl, aryl, and arylalkyl. Specific examples of capping groups include, but are not limited to, acetyl, benzoyl, formyl, trifluoroacetyl, benzyloxycarbonyl, tert-butyloxycarbonyl, biphenylylisopropyloxycarbonyl, triphenylmethyl, o-nitrobenzenesulfenyl, and diphenylphosphinyl.

In an alternate embodiment to the foregoing, the group Z may consist of the group $Z^2$-$Z^1$—, where Z is a capping group as described above, and $Z^1$ is 1, 2, or 3 additional amino acids.

C. Solid Supports and Peptides Coupled to Solid Supports.

Any suitable solid support may be used in the present invention. Solid supports include inorganic materials, organic materials, and combinations thereof. Examples of suitable solid support materials include membranes, semi-permeable membranes, capillaries, microarrays, multiple-well plates comprised of alumina, alumina supported polymers, polysaccharides including agarose, dextran, cellulose, chitosan, and polyacrylamide, polyacrylate, polystyrene, polyvinyl alcohol, glass, silica, silicon, zirconia, magnetite, semiconductors and combinations thereof. The solid support material may be in the form of beads, which are generally spherical. Alternatively, the support may be particulate or divided form having other regular or irregular shapes or it may be in the form of. Preferred solid support materials are those having minimal non-specific binding properties and that are physically and chemically resistant to the conditions used in the purification process employed in this invention such as changes in pH and ionic strength.

The solid support used in the present invention is preferably a polymer of acrylate. Examples of acrylate polymers include, but are not limited to, polymethacrylate, polyhydroxy methacrylate, polymethyl methacrylate, polyacrylamide, polyacrylonitrile and other acrylate derivatives. More preferably, the solid support is a methacrylate polymer. Most preferably, the methacrylate polymer is hydroxylated polymethacrylate amino resin with a bead size of 1000 Å and a particle size of 5-300 μm.

Ligands may be bound to solid support resin either directly or indirectly. When bound directly the ligand is coupled to the solid support material by formation of covalent chemical bonds between particular functional groups on the ligand (e.g., primary amines, sulfhydryls, carboxylic acids, hydroxyls, and aldehydes) and reactive groups on the support. A variety of activating compounds and schemes for directly bonding ligands to solid phase supports are known in the art (See U.S. Pat. No. 6,555,391, U.S. Pat. No. 6,773,599). Some examples of such activating compounds include cyanogen bromide, cyanuric chlorde, epichlorohydrin, divinyl sulphone, p-toluenesulphonyl chloride, 1,1'-carbonyldiimidazole, sodium meta-periodate, 2-fluro-1-methylpyridinium-toluene-4-sulphonate, glycidoxypropyltrimethoxysilane and 2,2,2-trifluroethanesulphonyl chloride. As indicated above, the procedures by which such activating steps are carried out are well known to those skilled in the art.

Ligands of this invention may or may not have linking or spacer groups bonded to the C terminus which when present may be used to bind the ligand to the solid support indirectly. The coupling of ligands to solid supports via spacer groups is a process well known in the art (See U.S. Pat. No. 5,273,660; U.S. Pat. No. 5,250,188; U.S. Pat. No. 5,190,661). When present the linking group may be a polymer or a monomer. A linking group may be a chain of from 1-10 amino acids. Other examples of linking groups include, but are not limited to, polyethylene glycol, polypropylene glycol, polyesters, polypeptides, polyethers, polysaccharides, glycidoxyalkyl, alkoxyalkyl, alkyl, glycidoxypropyl, ethyl, propyl, phenyl and methacryl; and silicon containing linking groups such as diethyl(triethoxysilylpropyl)malonate; 3-mercaptopropyltrimethoxysilane; 3-aminopropyltrimethoxysilane; N-[(3-trimethoxysilyl)propyl]ethylenediaminetriacetic acid; p-(chloromethyl)phenyltrimethoxysilane; vinyltriethoxysilane; 3-bromopropyltriethoxysilane; and 3-glycidoxypropyltrimethoxysilane.

D. Screening of Peptide Ligand Libraries for Peptide Ligands Binding Specifically to Immunoglobulin.

1. Preparation of the peptide ligand library. One embodiment of this invention is a method of identifying small peptide ligands with high affinity for immunoglobulin(s) of interest. This method comprises the screening of a library of peptides attached to a solid support, the peptides preferably being 5 to 7 amino acids in length, most preferably 6 amino acids in length.

Peptides of the present invention may be synthesized using any well-known technique in the art, including solid phase synthesis. Means for synthesizing peptide libraries on a solid phase support are well known in the art. (See U.S. Pat. No. 5,834,318; U.S. Pat. No. 6,207,807; U.S. Pat. No. 6,670,142; U.S. Pat. No. 6,599,875; R. Merrifield, J. Am. Chem. Soc. 85:2149-2154 (1963); G. Baray and R. Merrifield, Solid phase peptide synthesis, In The Peptides, E. Gross and J. Meinhofer, eds., Academic Press, New York, 1-284p (1980); G. Fields, Solid-Phase Peptide Synthesis, Academic Press, San Diego (1997), all of which are incorporated herein by reference).

In the present invention the peptide library is preferably synthesized on a solid phase support of hydroxylated polymethacrylate amino resin using fluorenylmethyoxycarbonyl (Fmoc) and tertiary butyloxycarbonyl (tBoc) chemistry. Most preferably the solid phase support is ToyopearlAF-amino650 EC resin. In this embodiment, a mixture of Fmoc-L-alanine and tBoc-L-alanine is coupled to the amino functionality on the resin. The tBoc groups are released and the free amino functionalities are protected by acetylating with acetic anhydride. Subsequently, the amino functionalities protected by Fmoc groups are released and used to link to other amino acids. All remaining amino groups are acetylated.

2. Labeling of immunoglobulin and Fc fragments and their detection. To identify peptide ligands having high affinity to immunoglobulin, the peptide ligand library is contacted with labeled immunoglobulin or labeled immunoglobulin fragments. Methods of labeling immunoglobulin or immunoglobulin fragments are well known in the art. (See, e.g., Harlow and Lane, 1988, Antibodies: A Laboratory Manual, Cold Spring Harbor Laboratory, New York; Ausubel et al., eds., Current Protocols In Molecular Biology, J. Wiley & Sons, New York (1999), both of which are incorporated herein by reference.)

Labels or detectable groups suitable for use in the present invention include but are not limited to biotin, fluorophores, antigens, porphyrins, and radioactive isotopes. Useful detectable groups are described above in further detail.

Means of detecting such labels or detectable groups are well known to those of skill in the art. Thus, for example, radiolabels and chemiluminescent labels may be detected using photographic film or scintillation counters, fluorescent markers may be detected using a photodetector to detect emitted light (e.g., as in fluorescence-activated cell sorting). Enzymatic labels are typically detected by providing the enzyme with a substrate and detecting the reaction product produced by the action of the enzyme on the substrate, and colorimetric labels are detected by simply visualizing the color associated with the label.

In the currently preferred embodiment, radioisotope labels are used. In the most preferred embodiment, $C^{14}$ radioisotope is used for labeling the immunoglobulin or immunoglobulin fragment. In this embodiment, the immunoglobulin or immunoglobulin fragment is labeled by reductive methylation utilizing sodium cyanoborohydride and $^{14}C$-formaldehyde. Labeled protein is separated from the $^{14}C$-formaldehyde using a desalting column. Liquid scintillation is used to determine the radioactivity of each fraction and the protein concentration is determined using the Micro BCA assay.

3. Binding of the peptide ligands to the radiolabeled immunoglobulin (or immunoglobulin fragment). The peptide library on the solid support resin is washed with 20% methanol and equilibrated at 4° C. in binding buffer. Preferably, the binding buffer is phosphate buffered saline; most preferably the binding buffer is phosphate buffered saline (PBS) containing 10 mM phosphate buffer, 2.0 mM KCl and 138 mM NaCl, pH 7.4.

Prior to contact with the labeled immunoglobulin and in order to reduce non-specific interactions between the radiolabeled immunoglobulins and the library, the peptide library beads are incubated with blocking solution, followed by an additional incubation with mammalian culture medium and human blood plasma (HBP). Preferably, the blocking solution is 1% Casein Hammersten Grade in PBS, and the mammalian cell culture medium is Minimal Essential Medium (MEM). The labeled immunoglobulin is then incubated with the library bead solution as a slurry for two hours at 20° C. Preferably, the immunoglobulin is labeled with radioisotopes; more preferably, the radioisotope is $^{14}C$. Following incubation, the slurry is transferred to a column. Preferably, the column is a Poly-Prep chromatography column.

The column containing the slurry is then washed with buffer. Preferably, the buffer is acetate buffer, more preferably, the buffer is acetate buffer, pH 5, containing Tween 20. Washed beads are suspended in 1% low melt agarose and poured onto a film. Preferably, the film is a 160-180 mm GelBond film and the density of the gel casting is 10 mg beads per gel casting. The gels are air dried and the radiolabeled immunoglobulin bound to the peptide ligands is detected using autoradiographic film. Positive beads, those containing peptide ligands binding to the labeled immunoglobulin, are collected and rescreened against labeled Fc fragment. The peptide ligands on the beads, which are positive after the second screen, are then sequenced using methods known in the art.

E. Methods of Use.

In a further embodiment of the present invention, the peptide ligands are used in the purification of immunoglobulins of interest from a composition comprising at least one immunoglobulin of interest and at least one other substance from which the immunoglobulin is to be separated. The peptide ligands, immobilized on a solid support or in solution, are contacted with a composition containing an immunoglobulin, the immunoglobulin then binding to the peptide ligand.

When using the peptides immobilized on a solid support, the composition containing the immunoglobulin may be contacted to the ligand-solid support either before or after the solid support material is packed into a column. For example, the peptide ligand-solid support material can be incubated with the composition containing the immunoglobulin and then this mixture can be packed into a column for further purification steps. Alternatively, the peptide ligand-solid support can be first packed into the column followed by the addition of the composition containing the immunoglobulin of interest. Preferably, the peptide ligand-solid support material is first packed in the column followed by the introduction of the composition containing the immunoglobulin of interest.

The peptide ligand-solid support material is introduced into the column using any conventional technique. Typically, the peptide ligand-solid support material is slurried in a suitable diluent and the resulting slurry pressure packed or pumped into the column. Suitable diluents include buffers such as phosphate buffered saline solutions; preferably the buffer is phosphate buffered saline (PBS) containing 10 mM phosphate buffer, 2.0 mM KCl and 138 mM NaCl, pH 7.4.

After the peptide ligand-solid support material is packed into the column, the column is pre-equilibrated by flushing with a diluent in order to remove any impurities and to equilibrate the support material in preparation for the addition of the immunoglobulin composition. Diluents suitable for this purpose include phosphate buffer, phosphate buffered saline, Tris buffers, sodium acetate buffer and citrate buffer. Preferably, the diluent is the binding buffer to be used in the introduction of the immunoglobulin composition to the column. A binding buffer is any buffer capable of promoting an interaction between immunoglobulin and the immobilized peptide ligand. Preferably, the binding buffer is phosphate buffered saline (PBS). More preferably, the binding buffer is phosphate buffered saline containing 10 mM phosphate buffer, 2.0 mM KCl and 138 mM NaCl, pH 7.4.

Following equilibration of the column, samples are added. Preferably samples are manually injected using a 100 μl loop. Each sample is injected at a flow rate of 50 μl/min for 10 minutes to allow sufficient residence time for binding.

The recovery of the immunoglobulin from the peptide ligand-solid support may involve any technique conventionally used in affinity chromatography to remove compounds from solid supports, including changes in pH or ionic strength. In one preferred embodiment of this invention, the immunoglobulin is eluted using phosphate buffer at pH 6. This relatively mild elution pH provides the advantage of maintaining the biological properties of the recovered immunoglobulin. Most preferably, following the addition of the immunoglobulin sample, the columns are washed sequentially with higher salt concentrations between 0.138 to 2 M NaCl, solutions with pH 6 to 4 and then 2% acetic acid in water.

It is noted that high salt concentrations appear not to be effective in eluting HIgG from the peptide ligand HWRGWV (SEQ ID NO:4); salt concentrations as high as 2M were found to be ineffective in eluting immunoglobulin from the peptide-ligand solid substrate. In addition, higher salt concentrations reduce the amount of immunoglobulin eluting at pH6. Exposure to higher salt concentrations may result in enhancement of hydrophobic interactions between the solid support material and the bound protein thus making elution of the immunoglobulin more difficult.

Elution of different immunoglobulins off of other ligands of this invention may require slightly different conditions. Variations necessary for elution of immunoglobulins from the peptide ligand-solid substrate material of this invention can be determined without undue experimentation using techniques well known in the art.

Eluted immunoglobulins are quantified using techniques well known in the art such as Micro-BCA (Pierce, Rockford, Ill.), absorbance at 280 or ELISA.

In an additional embodiment of the invention, the peptide ligands may be used in assays for the detection of antibodies in a solution or composition suspected of containing the same. The ligand may be coupled to a detectable group or label including, but not limited to, those described above. The contacting and separating steps can be carried out in solution or with immobilized peptide ligands. Methods of detecting labeled peptide ligands include but are not limited to those described above for the detection of labeled immunoglobulin. When carried out in solution, peptide ligand bound immunoglobulin can be separated and/or detected from the solution using a variety of techniques including, but not limited to, fluorescence-activated cell sorting, membrane filtration and mass spectrometry.

F. EXAMPLES

The present invention is described in greater detail in the following non-limiting examples.

Example 1

Peptide Synthesis

Figure 2:
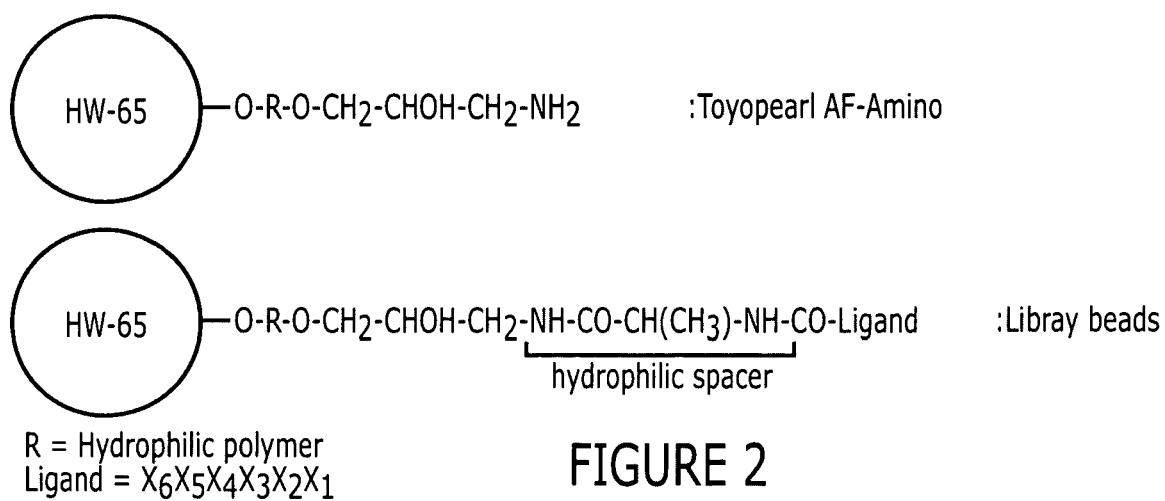
FIG. 2. Library bead structure.

The peptide libraries used in this study were synthesized by Peptides International (Louisville, Ky.) on Toyopearl AF-amino-650 EC resin (Tosoh Bioscience, Montgomeryville, Pa.). The base resin (FIG. 2) from Tosoh Bioscience is a hydroxylated polymethacrylate amino resin with a pore size of 1000 Å and a particle size of 100-300 μm. The large particle size is particularly advantageous for use in screening since it makes it easier to identify and sequence the particles. Fmoc-L-alanine, a protecting group, was coupled to the amino functionality on the resin. Subsequently, the amino functionalities protected by Fmoc groups were released and used to link to other amino acids. Eighteen of the twenty amino acids (excepting cysteine and methionine) were used in this library synthesis. The amino acid lengths used were six (hexameric library), three (trimeric library) or one (monomeric library) and the peptide density was 400 μmoles/gm. The structure of this library is shown in FIG. 2.

Once a ligand was identified, larger batches of peptide were produced for secondary and tertiary screening. Individual ligands were synthesized by Peptides International (Louisville, Ky.) on Toyopearl AF-Amino-650 M resin (Tosoh Bioscience, Montgomeryville, Pa.) following the procedure described by Buettner et al. (1996). This resin has a mean particle diameter of 65 μm. A mixture of Fmoc-L-alanine and tBoc group (tert butyloxycarbonyl)-L-alanine was coupled to the amino functionality on the resin. The tBoc groups were released and the free amino functionalities were protected by acetylating with acetic anhydride. Subsequently, the amino functionalities protected by Fmoc groups were released and used to link to other amino acids. All remaining amino groups were acetylated. The peptide density for these re-synthesized resins was 100 μmol/gm of resin.

Example 2

Positive Controls Used in Screenings

Two positive controls were used in this study to compare HIgG binding properties. They are protein A Sepharose CL-4B (protein A for short) and MAbsorbent A2P (A2P for short). Protein A Sepharose CL-4B (Amersham Biosciences, Piscataway, N.J.) is protein A immobilized by the CNBr method to 4% cross-linked agarose beads (Sepharose CL-4B) with a mean size of 90 μm. Protein A binds only to the Fc fragment of HIgG 1,2 and 4. MAbsorbent A2P (Prometic Biosciences, Burtonsville, Md.) is made by immobilizing a synthetic triazine based bifunctional ligand onto a 6% cross-linked agarose matrix (PuraBead 6XL) whose mean particle size is around 100 μm. MAbsorbent A2P binds to both Fc and Fab fragment as well as all sub-classes of IgG.

Example 3

Radiolabeling of Whole HIgG and Fc Fragment of HIgG

Radiolabeling process. Fc fragment and HIgG (Bethyl Laboratories, Inc. Montgomery, Tex.) were labeled by reductive methylation (Equation 1, below) utilizing sodium cyanoborohydride (NaCNBH3) and 14C-formaldehyde (H14CHO, PerkinElmer) (Jentoft and Dearborn, 1983). The 14C formaldehyde was added at a 3-fold molar excess over 5% of the total methylation sites (39 total in Fc and more than 85 in intact HIgG). Sodium cyanoborohydride was added at 10× the amount of formaldehyde. The reaction was performed at 4° C. overnight. Following the reaction, the labeled protein was separated from 14C-formaldehyde using an EconoPac 10DG Desalting Column (Biorad, Hercules, Calif.) equilibrated with 0.1 M sodium phosphate, pH 7.0. The radioactivity of each fraction was determined using a Pacard 1500 Tri-Carb Liquid Scintillation Analyzer (Meridan, Conn.) and CytoScint ES scintillation liquid from ICN (Mesa, Calif.). The protein concentration in each fraction was assayed by Micro BCA assay using a Shimadzu UV-160 UV-Vis Recording Spectrophotometer. An equation showing the reductive alkylation of amino groups using formaldehyde and sodium cyanoborohydride is shown below:

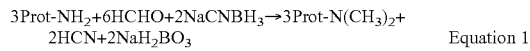

$$3\text{Prot-NH}_2 + 6\text{HCHO} + 2\text{NaCNBH}_3 \rightarrow 3\text{Prot-N(CH}_3)_2 + 2\text{HCN} + 2\text{NaH}_2\text{BO}_3 \quad \text{Equation 1}$$

Comparison of the binding ability of labeled and unlabeled protein. The binding of labeled and unlabeled Fc fragments to the two positive control resins, Protein A Sepharose CL-4B and MAbsorbent A2P were compared. The resins were washed as indicated by the manufacturer and equilibrated in 20 mM phosphate buffer for 1 hour. Radiolabeled and unlabeled Fc fragment was added into a known amount (2.6 mg) of resin and incubated for 30 minutes in a centrifugal filter vessel with a 0.45 μm Durapore membrane (Millipore, Milford, Mass.). The flow through was collected by centrifugation and the Fc concentration was measured at 280 nm (A280). The binding capacity of each resin was calculated by mass balance.

Example 4

Primary Screening

Hexamer peptide libraries on Toyopearl AF-Amino-650 EC resin were used to assess the binding of individual hexameric peptides to target protein. The library was washed with 20% methanol and equilibrated overnight at 4° C. with the binding buffer, phosphate buffered saline (PBS) (Sigma, St. Louis, Mo.) containing 10 mM phosphate buffer, 2.0 mM KCl and 138 mM NaCl, pH 7.4. The beads were first incubated with the blocking solution [1% (w/v) Casein Hammersten Grade in PBS, pH 7.4]. Human blood plasma (HBP) and mammalian culture medium MEM (Minimum Essential Medium) containing 10% fetal calf serum (FCS) and 5% tryptose phosphate broth (TPB), were also used as blockers after casein treatment to minimize nonspecific interactions between the library and 14C-protein. 14C-protein (1 μM) was added to the bead solution slurries and rotated for 2 hours at room temperature (20° C.). Following the incubation, the beads were transferred to a Poly-Prep chromatography column (Biorad, Hercules, Calif.) and washed thoroughly with pH 5 acetate buffer containing 0.05% (w/v) Tween 20 (Sigma, St. Louis, Mo.) until the radioactivity of the flow-through reached background levels. The washed beads were suspended in 1% low melting agarose (Biorad, Hercules, Calif.) at 45° C. and poured onto a 160-180 mm GelBond film (Bio Whittaker Molecular Applications, Rockland, Me.) to form a density of 10 mg beads/gel casting.

A Kodak Biomax MR autoradiography film (Fisher, Atlanta, Ga.) was exposed to the air-dried agarose gel. Positive signals on the film were confirmed by re-exposure of a new film to the gel. Mabsorbent A2P and Protein A Sepharose CL-4B, were used as the positive controls to confirm that binding was occurring during the screening process. Toyopearl AF acetylated 650 EC beads were used as a negative control to exclude the library matrix binding to target protein.

Several experiments were carried out to improve the screening conditions such as different blockers (Human plasma, MEM), wash pH (7.4 and 5), wash salt concentration (0.25-0.5 M NaCl). The positive beads from experiments of the first cycle of primary screening were collected and re-screened against 14C-Fc fragment using the procedure described above. Positive beads from the re-screened beads were then sent to Iowa State University (The Protein Facility Office of Biotechnology, Ames, Iowa) for sequencing by Edman degradation. In addition to the hexamer libraries, some screening experiments were done with libraries of peptide trimers and monomers to better understand the nature of the interactions between Fc and HIgG and the peptides.

Example 5

Secondary Screening

A secondary screening step was conducted in a batch format to confirm the binding of the target protein to the peptide ligands from the primary screening. Some peptides that bound weakly to the target protein could be eliminated by the secondary screening. A total of nine leads were examined together with two positive controls, Protein A Sepharose C1-4B and MABsorbent A2P, and two negative controls, acetylated and nonacetylated Toyopearl amino resin (Tosoh Bioscience). The batch format was used in both competitive and non-competitive modes. The non-competitive mode involved screening using only pure target proteins in PBS buffer. For the competitive mode, target proteins were spiked into mammalian culture medium MEM (Minimum Essential Medium) containing 10% fetal calf serum (FCS) and 5% tryptose phosphate broth (TPB).

Two target proteins, the Fc fragment of human IgG (HIgG) and intact HIgG, were applied at a concentration of 1 μM. To carry out the secondary screening, 20 mg of the re-synthesized resins were swelled with 20% methanol for one hour, then washed thoroughly and equilibrated with PBS buffer. The beads were incubated with 400 μl of 1 μM 14C-Fc or 14C-IgG in the corresponding solutions in a 0.5 ml centrifuge filter with a 0.45 μm Durapore membrane (Millipore, Milford, Mass.) on a rotating plate for two hours. The particles were washed with PBS buffer for 15 min, and then sequentially washed for one hour each with 400 μl of: 1 M NaCl in PBS, then 2% acetic acid (AcOH) and 6 M guanidine chloride (GdnHCl). After centrifugation each solution was collected into scintillation fluid for radioactivity counting. The total unbound protein was determined by combining the counts of unbound protein and the wash of PBS. Finally, resins were suspended in scintillation liquid and counted for radioactivity in the same manner, allowing a total radioactivity balance.

Example 6

Tertiary Screening

Adsorption isotherms and column chromatography studies were carried out to better understand the binding of the ligands to HIgG. Adsorption isotherms of the ligand HWRGWV (SEQ ID NO: 4) with a wide range of peptide densities, and the ligands HYFKFD (SEQ ID NO: 11), HVHYYW (SEQ ID NO: 12), HFRRHL (SEQ ID NO: 21), WHWRKR (SEQ ID NO: 7) and YYWLHH (SEQ ID NO: 8) at 0.1 meq/g were determined. In addition, the chromatographic performance of HWRGWV (SEQ ID NO: 4), HYFKFD (SEQ ID NO: 11), HVHYYW (SEQ ID NO: 12), HFRRHL (SEQ ID NO: 21), and YYWLHH (SEQ ID NO: 8) resins were investigated in a column format at a peptide density of 0.1 meq/g.

Adsorption isotherm measurements. Individual peptide sequences determined to bind the Fc fragment of HIgG in primary screening were synthesized directly onto Toyopearl AF-amino-650 M resin (Tosoh BioSciences, Montgomeryville, Pa.) at a substitution of 100 µmol/g resin (Peptides International, Louisville, Ky.). All remaining amino groups were acetylated. Adsorption isotherms were measured in a set of batch experiments at room temperature. All the experiments were performed at least in duplicate. Beads were washed thoroughly and equilibrated with PBS buffer. Centrifugal filters (0.5 ml) with 0.45 µm Durapore membranes (Millipore, Milford, Mass.) were used as adsorption vessels. Resins (10 mg of resin in each vessel) were then equilibrated overnight in PBS, pH 7.4 (Sigma Chemical, St. Louis, Mo.). After removing the PBS, 400 µl of HIgG solutions with concentrations from 0.05 to 10 mg/ml in PBS were added separately to the reaction vessels and incubated on an orbital shaker for 2 hours. The unbound HIgG fractions were collected by centrifugation and the protein concentrations were determined using a Micro-BCA Assay (Pierce, Rockford, Ill.) or by UV-absorbance at 280 nm. The amount of bound HIgG was calculated by mass balance. The data were fit to a Langmuir isotherm model (see Equation 2, below).

$$q = q_m C \div (K_d + C)$$ Equation 2.

where,
q=Concentration of bound adsorbate mg-protein/g-resin
C=Concentration of free adsorbate mg-protein/ml-solution
$K_d$=Dissociation constant mg/ml
$q_m$=Maximum capacity constant mg-protein/g-resin Chromatography format. To test the selectivity of the peptides that showed positive binding in the secondary screening, the performance of the peptide ligands was investigated in a chromatography column format. The resins were wet packed into 5×0.4 cm (ID) Omega columns (Upchurch, Oak Harbor, Wash.) and tested on a Waters 626 HPLC unit with a built in UV detector at 280 nm. Samples were manually injected using a 100 µl sample loop (Thomson, Springfield, Va.). The columns were pre-equilibrated with binding buffer (10 mM PBS containing 0.138M NaCl and 0.002M KCl, pH 7.4). Each sample was injected at a flow rate of 50 µl/min for 10 minutes to allow sufficient residence time for binding. The flow rate was increased for the remainder of the run to 0.4 ml/min unless otherwise noted. The columns were washed sequentially with the binding buffer, higher salt concentrations between 0.138 to 2 M NaCl in binding buffer, solutions with pH from 6 to 4, and then 2% acetic acid in water. As in the secondary screening, a noncompetitive format was used first in the tertiary screening. A solution of 5 mg/ml HIgG (Sigma, Atlanta, Tex.) in PBS buffer was injected into the column to verify the binding ability of selected resins. In the competitive tertiary screenings, MEM (containing 10% FCS and 5% TPB) spiked with HIgG at a 5 mg/ml was applied directly to the column.

To investigate the effect of salt in the binding buffer on the separation of HIgG from MEM, the salt concentration of binding buffer was increased to 0.3M NaCl. All experiments were conducted at room temperature. Fractions were collected and concentrated by centrifugation at 4° C., 11,000 rpm for 90-180 minutes using a Micro Con YM-3 filter (regenerated cellulose 3,000 MWCO, Millipore). Concentrated fractions were analyzed by sodium dodecyl sulfate-polyacrylamide gel electrophoresis (SDS-PAGE) to observe the protein compositions. The total protein concentration of the samples was measured at 280 nm and the specific concentration of HIgG was detected by enzyme-linked immunosorbent assay (ELISA) at 450 nm (described in detail below).

Example 7

Analytical Methods

Micro-BCA and A280. Total protein concentrations were quantified by either Micro-BCA (Pierce, Rockford, Ill.) or adsorption at 280 nm. The absorbance was measured in a µQant plate reader (Bio-Tek Instruments, Winooski, Vt.). The samples were loaded on a UV-microplate (Corning).

HIgG ELISA. Human IgG concentrations were determined by ELISA at room temperature. Human IgG from Bethyl Laboratories, Inc. (Montgomery, Tex.) was used as a standard protein. The capture antibody, goat anti-human IgG (Fc) (Bethyl) at a concentration of 5 µg/ml was coated on a microtitre plate (Nunc, Rochester, N.Y.). After coating and washing with wash solution (50 mM TBS containing 0.05% Tween 20, pH 8.0), the unspecific binding sites of the plate were blocked with Blocking Solution (50 mM TBS containing 1% BSA, pH 8.0). After removing the blocking solution, samples and protein standard solutions were added to the plate and incubated for 2 hours after the blocking step. As the detecting antibody, horseradish peroxidase goat anti-human IgG (H+ L) (Biomeda, Foster City, Calif.) at a 1:50,000 dilution was introduced to each well and incubated for 1 hour. After incubating with substrate TMB (3, 3', 5', 5' tetramethylbenzidine, Pierce, Rockford, Ill.) for 20 minutes, color development was stopped using 1M H2SO4. The absorbance at 450 nm was read on the µQant plate-reader and the concentration of HIgG was calculated according to the standard curve. All steps were conducted at room temperature.

Gel electrophoresis. The protein content of the concentrated chromatographic samples were determined by SDS-PAGE under reducing conditions using NuPAGE Novex 4-12% Bis-Tris gels (Invitrogen, Carlsbad, Calif.) on an XCell SuperLock™ Mini-Cell system from Invitrogen (Carlsbad, Calif.). The gels were stained either by SimpleBlue SafeSatin or by SilverXpress Silver Stain (Invitrogen, Carlsbad, Calif.). The gels were scanned on HP Scanjet 4570C and their density was analyzed using the software ImageJ 1.32j (Wayne Rasband, National Institutes of Health, USA).

Example 8

Radiolabeling of HIgG and Fc Fragment of HIgG

By using a reductive methylation reaction, the target proteins (Fc fragment and intact HIgG) were radiolabeled by 14C. The radiolabeled proteins had a radioactivity of approximately 1014 decompositions per minute (dpm)/mole protein which corresponds to approximately 2% of maximum labeling for the Fc fragment and about 4% for the whole HIgG.

The binding properties of labeled and unlabelled Fc to the two positive control resins, Protein A Sepharose CL-4B (Amersham) and synthetic peptide MAbsorbent A2P (Prometic Biosciences) were compared. Compared to the advertised binding capacity of 20 mg IgG/ml of Protein A resin, unlabeled Fc was found to bind approximately 10 mg/ml of Protein A resin while the labeled Fc binding ability decreased to about 5 mg/ml of Protein A (Table 1). Similarly, the binding capacity of resin MAbsorbent A2P, claimed to be 50 mg human IgG/ml of resin, decreased from 16 mg Fc/ml of resin for unlabeled Fc to 9 mg/ml for labeled HIgG.

TABLE 1

Binding ability comparison between $^{14}$C-labeled and unlabeled Fc

| Resin | Unlabeled Fc, mg/ml | $^{14}$C-Fc, mg/ml |
| --- | --- | --- |
| Protein A | 9.9 | 4.9 |
| A2P | 16.1 | 9.1 |

Example 9

Primary Screening Results

As shown above, radiolabeling decreases the binding ability of the Fc fragment. A low methylation percentage is desired in order to keep the biological properties of labeled protein nearly the same as the natural target. Less than 4% of the amino groups on HIgG and 2% of its Fc fragment were methylated in our study. Casein, human plasma and MEM were used to block the nonspecific binding sites for HIgG on library beads. Optimization of the experimental conditions in the primary screening showed that the usage of a pH 4 wash led to fewer positive beads. It was difficult to compare the intensity of the signals obtained from different particles on different GelBond gels, due to the difference in particle size, development conditions and gel coverage. Therefore, a rescreening process was employed to delineate the difference by putting all picked positive beads onto a single GelBond gel. Four libraries were screened in the primary study. One was a "big bead" hexameric library built on Toyopearl AF-Amino-650 EC resin. The other three were "small bead" monomeric, trimeric and hexameric libraries all built on Toyopearl AF-Amino-650 M resin. Two radiolabeled proteins, intact HIgG and its Fc fragment, were used in screening. Leads identified during primary screening were sequenced by Edman chemistry and the results are shown in Table 2. A total of 4% (0.7 gram) of the "big bead" hexameric library has been randomly screened with 11 peptides being identified in screening against Fc fragment and 8 peptides in screening against intact HIgG and then re-screened by Fc. A total of 663 mg of a hexameric library without H at the N-terminus, 75.8 mg trimeric, and 6 mg monomeric "small bead" libraries were also screened against Fc fragment and a total of 15 ligands were identified.

TABLE 2

Sequences obtained after primary screening. Sequences begin with N-terminal amino acid.

| Library | Big bead hexameric | SEQ ID No | Big bead hexameric | SEQ ID No | Small bead monomeric | Small bead trimeric | Small bead hexameric (No H at N-terminus) | SEQ ID No |
| --- | --- | --- | --- | --- | --- | --- | --- | --- |
| | $^{14}$C-Fc | — | $^{14}$C-HIgG and $^{14}$C-Fc | — | $^{14}$C-Fc | $^{14}$C-Fc | $^{14}$C-Fc | — |
| | HYGLGW | SEQ ID NO: 1 | HWGPTK | SEQ ID NO: 9 | Y | HIW | APHHLL | SEQ ID NO: 26 |
| | HEILYW | SEQ ID NO: 2 | HIQLDG | SEQ ID NO: 19 | H | KGE | KGXQXX | SEQ ID NO: 27 |
| | HFDKGF | SEQ ID NO: 3 | HYIDAK | SEQ ID NO: 15 | I | YHQ | PTHLFP | SEQ ID NO: 28 |
| | HWRGWV | SEQ ID NO: 4 | HVHYYW | SEQ ID NO: 12 | Y | HIW | KLQMVX | SEQ ID NO: 29 |
| | HANGFL | SEQ ID NO: 5 | HPWYVT | SEQ ID NO: 17 | | | KXXGX | SEQ ID NO: 30 |
| Protein | HRPKIF | SEQ ID NO: 6 OR 34 | HWIDPL | SEQ ID NO: 10 | | | KRXXX | SEQ ID NO: 31 |
| | HFDKGF | SEQ ID NO: 3 | HYFKFD | SEQ ID NO: 11 | | | KGGXX | SEQ ID NO: 32 |
| | HETRFS | SEQ ID NO: 24 | HLKWYA | SEQ ID NO: 16 | | | | |
| | HWGTIA | SEQ ID NO: 25 | | | | | | |
| | HDVFHT | SEQ ID NO: 18 | | | | | | |
| | HVWQLK | SEQ ID NO: 20 | | | | | | |

It is interesting to note that the first amino acid (N-terminus) of all the positive beads identified from the big bead library is histidine (H). This complete sequence homology with the same amino acid showing at the same location on a hexamer is extremely unusual and has not been seen in prior experience in this laboratory. To confirm the results, three negative beads were sent for sequencing and no histidine was found in the first cycle. This gives us confidence that the finding of histidine in this first location is a true result and not an artifact from the sequencing.

The second amino acids among the ligands identified in big bead library showed high homology too. Sixty-three percent of these amino acids are hydrophobic when screened against Fc fragment and amazingly 100% are hydrophobic, more specifically aromatic, when screened against intact HIgG. These sequences indicate that the combination of an aromatic amino acid and histidine may play an important role in peptide binding to HIgG. It is also interesting to note that there are two identical sequences, HFDKGF (SEQ ID NO: 3), in the screening of big bead library using Fc fragment. This also does not happen very often, since the probability of picking out two beads with exactly the same sequence from screening over 6×105 resin particles is extremely small.

To test the binding of the single amino acid histidine to HIgG, a small bead monomeric library was screened against 14C-Fc fragment. It was found that not only histidine, but also tyrosine and isoleucine can bind to HIgG. This is an indication that the identified ligands probably bind to HIgG through the whole sequence instead of through histidine alone, though H plays a very important role.

To eliminate the effects of histidine on screening, and to see if there was any other potential binding mechanism through another terminal amino acid, a small bead hexameric library without histidine at the N-terminus was screened against 14C-Fc fragment. The results are listed in Table 2. Lysine turned out to be a very important amino acid at the terminal end in the identified ligands with a frequency of 71% when N-terminal histidine was excluded from the library sequences. With this extremely high homology, it might be possible to decrease the cost of ligand by truncating a hexamer to a trimer. Trimer leads were identified by screening a trimeric library. The results impose more emphasis on lysine, histidine and tyrosine, the first amino acids identified in other screens.

Example 10

Secondary Screening

The secondary screening was used to confirm the ability of the peptide ligands from the primary screening to bind HIgG and Fc fragment efficiently and determine whether they bind in preference to non-specific blocking proteins. Six leads from the first column in Table 2, HYGLGW (SEQ ID NO: 1), HEILYW (SEQ ID NO: 2), HFDKGF (SEQ ID NO: 3), HWRGWV (SEQ ID NO: 4), HANGFL (SEQ ID NO: 5) and HRPKIF (SEQ ID NO: 6 OR 34) were re-synthesized and tested in the first round of secondary screening. The results of this first round are shown in Table 3. All leads in the second column, HDVFHT (SEQ ID NO: 18) and HVWQLK (SEQ ID NO: 20) in the first column of Table 2, together with HIW, KLQWVH, (SEQ ID NO: 22) HFRRHL (SEQ ID NO: 21) and KRGFYY (SEQ ID NO: 23) were re-synthesized and tested in the second round of secondary screening. The results of the second round of secondary screening are shown in Table 4. Ligands were picked with the criteria that each represents a different group sorted according to the properties of amino acids in each position. KLQWVH (SEQ ID NO: 22) is from KLQMVX (SEQ ID NO: 29), with the substitution of M with W and X with H because no methionine exits in our peptide library and, interestingly, it is an exact reverse sequence of HVWQLK (SEQ ID NO: 20) in the first column of Table 2. HFRRHL (SEQ ID NO: 21) is from the subunit, GFRKYLHFRRHLL (SEQ ID NO: 33), of a multiple antigenic peptide (MAP) (A. Verdoliva, et al., Journal of Chromatography B-Biomedical Applications 664(1):175-183. (1995)) synthesized to purify polyclonal antibodies raised against MAP. KRGFYY(SEQ ID NO:23) is a combination of KRXXXX (SEQ ID NO: 35), KXXGX (SEQ ID NO: 30), and aromatic amino acids F and YY presenting in identified ligands (Table 2).

TABLE 3

Percentage of binding of target protein to ligands tested in the first round of secondary screening. Protein A and A2P are two positive controls and acetylated and non-acetylated amino resin are two negative controls.

| Peptide Bound % | | HIgG | | Fc fragment | |
| --- | --- | --- | --- | --- | --- |
| | | Non-competitive (Micro-BCA) | Competitive | Non-competitive | Competitive |
| HYGLGW | SEQ ID NO: 1 | 17.89 | 14.48 | 19.75 | 4.91 |
| HEILYW | SEQ ID NO: 2 | 9.16 | 5.50 | 18.01 | 3.20 |
| HFDKGF | SEQ ID NO: 3 | 10.66 | 6.01 | 12.95 | 4.28 |
| HWRGWV | SEQ ID NO: 4 | 62.23 | 24.42 | 82.49 | 8.13 |
| HANGFL | SEQ ID NO: 5 | 10.52 | 5.58 | 10.23 | 25.64 |
| HRPLIF | SEQ ID NO: 6 | 11.20 | 4.51 | 21.46 | 24.48 |
| WHWRKR | SEQ ID NO: 7 | 66.25 | 10.88 | 88.17 | 16.48 |

TABLE 3-continued

Percentage of binding of target protein to ligands tested in the first round of secondary screening. Protein A and A2P are two positive controls and acetylated and non-acetylated amino resin are two negative controls.

| Peptide Bound % | | Non-competitive HIgG (Micro-BCA) | Competitive | Fc fragment Non-competitive | Competitive |
|---|---|---|---|---|---|
| YYWLHH | SEQ ID NO: 8 | 91.29 | 41.88 | 40.36 | 8.85 |
| Protein A | — | 87.4 | 83.43 | 93.67 | 78.63 |
| A2P | — | 94.43 | 89.30 | 86.48 | 43.34 |
| Toyo Non-Ac resin | — | 11.48 | 0.69 | 90.60 | 11.94 |
| Toyo Ac-amino resin | — | 14.66 | 4.15 | 7.18 | 4.99 |

The first round of secondary screening of the ligands identified in the primary screening against Fc fragment of HIgG. A total of eight ligands were examined in the first round of secondary screening. They are HYGLGW (SEQ ID NO: 1), HEILYW (SEQ ID NO: 2), HFDKGF (SEQ ID NO: 3), HWRGWV (SEQ ID NO: 4), HANGFL (SEQ ID NO: 5), HRPKIF (SEQ ID NO: 6), WHWRKR (SEQ ID NO: 7) and YYWLHH (SEQ ID NO: 8). The first six leads were found in the screening of big bead hexameric library against 14C-Fc fragment. Among these six, HWRGWV (SEQ ID NO: 4) is the best binder to either HIgG or Fc fragment. Two other ligands, WHWRKR (SEQ ID NO: 7) and YYWLHH (SEQ ID NO: 8), were included in the secondary screening because they have structures similar to HWRGWV (SEQ ID NO: 4) found in the primary screening of human IgG. Lead WHWRKR (SEQ ID NO: 7), was identified by P. Gurgel, et al. (*Separation Science and Technology*, 36, 2411-2431 (2001)) to isolate alpha-lactalbumin from whey protein isolate (WPI). Lead YYWLHH (SEQ ID NO: 8) was originally identified by G. Wang et al. (J. Peptide Research, 64, 51-64 (2004)) to isolate Staphyloccocal enterotoxin B from complex mixtures.

The secondary screening results shown in Table 3 indicate that three peptides, HWRGWV (SEQ ID NO: 4), WHWRKR (SEQ ID NO: 7) and YYWLHH (SEQ ID NO: 8), bind the most target protein in both competitive and non-competitive modes. It is interesting to note that all of those three leads have similarities in the type and hydrophobicity of residues in their sequences. They bind both IgG and Fc more than 60% in PBS, though only 42% at most in MEM under competitive condition. All the peptides seem to bind Fc more efficiently than HIgG in PBS, however, they bind Fc less efficiently than HIgG in MEM. It is likely that the presence of the Fab fragment affects the interaction between peptides and the Fc fragment. It was found that the A2P resin binds both the Fc and HIgG so tightly that elution using 2% acetic acid is not sufficient for complete removal. This is a potential disadvantage of A2P that would require significant modifications of elution conditions to obtain active protein. Amazingly, under non-competitive conditions, YYWLHH (SEQ ID NO: 8), protein A and A2P all bind more than 90% of Fc and HIgG. Under competitive conditions, however, the bound HIgG on YYWLHH (SEQ ID NO: 8) drops to 42% while Protein A and A2P still bind more than 80%. The secondary screening reduced the number of lead candidates from 6 down to only one (HWRGWV (SEQ ID NO: 4)), which was used in additional studies.

The second round of secondary screening of the ligands identified in primary screening against intact HIgG. In addition to HWRGWV (SEQ ID NO: 4), WHWRKR (SEQ ID NO: 7), and YYWLHH (SEQ ID NO: 8), three ligands, HYFKFD (SEQ ID NO: 11), HVHYYW (SEQ ID NO: 12), and HFRRHL (SEQ ID NO: 21) were identified as good binders by selectively binding more than 40% HIgG in the presence of MEM (Table 4) and chosen for tertiary screening. HYFKFD (SEQ ID NO: 11) and HVHYYW (SEQ ID NO: 12) are the ligands found the best among the resynthesized ligands identified in the second round of the hexameric library screening against intact HIgG (Table 2). HFRRHL (SEQ ID NO: 21) is a truncation of the subunit, GFRKYLHFRRHLL (SEQ ID NO: 33), of a multiple antigenic peptide (MAP) synthesized to purify polyclonal antibodies raised against MAP. The HIgG selectivity of these three ligands over MEM proteins is higher than that of HWRGWV (SEQ ID NO: 4) and close to YYWLHH (SEQ ID NO: 8) (Table 3). However, the data of Table 4 cannot be directly compared with these of Table 3 because, in addition to normal experimental variations, the radiolabel extent of HIgG was 3.6% for the results shown in Table 3 and 2.9% for those in Table 4. The secondary screening, as mentioned before, was conducted using HIgG radiolabeled through reductive methylation reaction (Equation 1). The higher the radiolabel extent, the more hydrophobic HIgG is and sequentially the less binding ability HIgG has. This is also the reason that ligands HLKWYA (SEQ ID NO: 16) and HPWYVT (SEQ ID NO: 17) (Table 4) were not selected for tertiary screening even though they also selectively bind 23-26% HIgG which are comparable to 24% of the ligand HWRGWV (SEQ ID NO: 4) (Table 3).

TABLE 4

Secondary screening of the leads identified in the primary screening of big bead library against $^{14}$C-HIgG and of small bead library against $^{14}$C-Fc fragment indicated in Table 2.

|  |  |  | Competitive condition | | Non-competitive | |
|---|---|---|---|---|---|---|
|  | Sequence |  | Bound | Unbound | Bound | Unbound |
| Leads | HWGPTK | SEQ ID NO: 9 | 19.93 | 80.07 | 14.39 | 85.61 |
|  | HWIDPL | SEQ ID NO: 10 | 19.91 | 80.09 | 9.03 | 90.97 |
|  | HYFKFD | SEQ ID NO: 11 | 43.26 | 56.74 | 69.31 | 30.69 |
|  | HVHYYW | SEQ ID NO: 12 | 43.27 | 56.73 | 55.49 | 44.51 |
|  | HIWA | SEQ ID NO: 13 | 12.87 | 87.13 | 7.90 | 92.10 |
|  | KGEA | SEQ ID NO: 14 | 7.34 | 92.66 | 6.08 | 93.92 |
|  | HYIDAK | SEQ ID NO: 15 | 8.64 | 91.36 | / | / |
|  | HLKWYA | SEQ ID NO: 16 | 23.47 | 76.53 | / | / |
|  | HPWYVT | SEQ ID NO: 17 | 26.96 | 73.04 | / | / |
|  | HDVFHT | SEQ ID NO: 18 | 8.55 | 91.45 | / | / |
|  | HIQLDG | SEQ ID NO: 19 | 10.03 | 89.97 | / | / |
|  | HVWQLK | SEQ ID NO: 20 | 15.05 | 84.95 | / | / |
|  | HFRRHL | SEQ ID NO: 21 | 40.87 | 59.13 | / | / |
|  | KLQWVH | SEQ ID NO: 22 | 12.15 | 87.85 | / | / |
|  | KRGFYY | SEQ ID NO: 23 | 17.27 | 82.73 | / | / |
| Control | Protein A | — | 89.15 | 10.85 | 87.40 | 12.60 |
|  | Non-Ac | — | 9.04 | 90.96 | 3.48 | 96.52 |

Example 11

Adsorption Isotherms

Figure 3A:
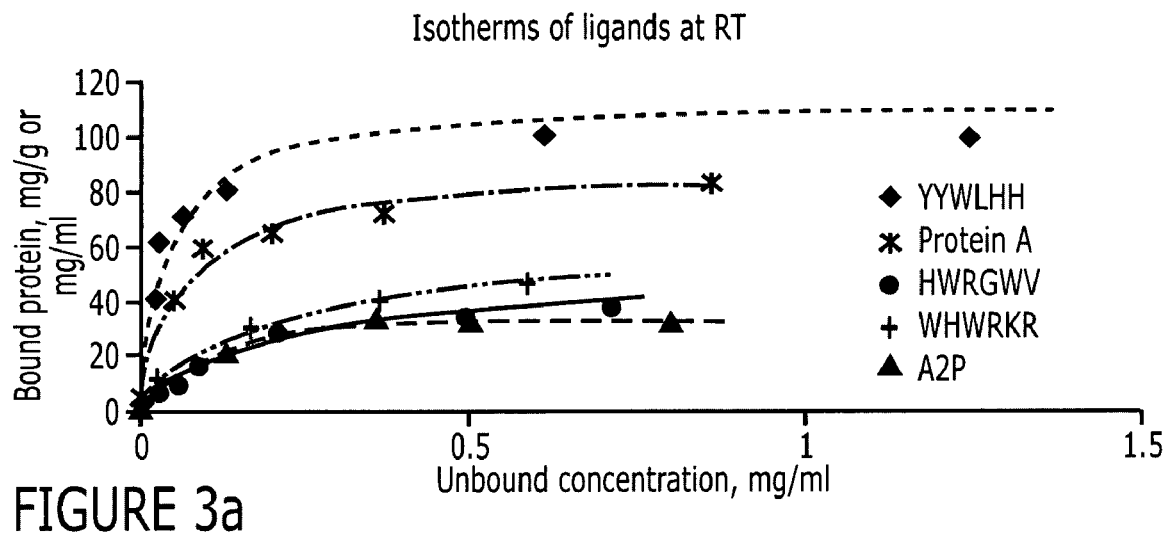
FIG. 3. Isotherms for HIgG adsorption to HWRGWV (SEQ ID NO: 4), YYWLHH (SEQ ID NO: 8), WHWRKR (SEQ ID NO: 7), A2P and Protein A. (a) A Langmuir fit; (b) double reciprocal curve of bound and unbound proteins.
Figure 3B:
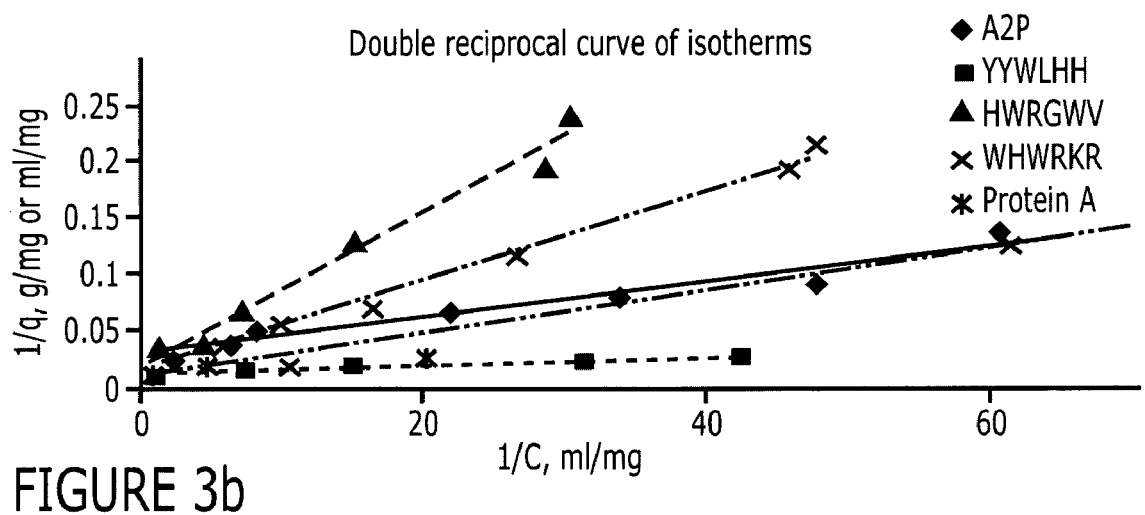

Adsorption isotherms of HWRGWV (SEQ ID NO: 4), YYWLHH (SEQ ID NO: 8), and WHWRKR (SEQ ID NO: 7). The adsorption isotherm provides values of the binding capacity and affinity of the peptide resins from the secondary screening that bind HIgG. Three leads (HWRGWV (SEQ ID NO: 4), YYWLHH (SEQ ID NO: 8), and WHWRKR (SEQ ID NO: 7) at a peptide density of 0.1 meq/g), as well as two positive controls (Protein A and A2P) were studied. The adsorption data was fit directly to a Langmuir model and the results are shown in Table 5 and FIG. 3a. The values of the Langmuir isotherm parameters were also fit using a double reciprocal plot shown in FIG. 3b. The dissociation constants (Kd) and maximum capacity constants (qm) for each ligand are listed in Table 5. Values of Kd obtained from the double reciprocal plots and the direct Langmuir fit agree fairly well, but the binding capacity values from the double reciprocal analysis do not agree well with the binding data. The reason for this is that the double reciprocal analysis weighs the low concentration data more strongly. The capacities of the two positive controls obtained by isotherms are pretty close to the manufacturers' claims, 20 mg/ml and 20-30 mg/ml for protein A and A2P respectively. However, the qm values from double reciprocal curve are higher than those shown in the Langmuir curve except for A2P and protein A. The Kd values for the peptide ligands are in the range from $10^{-6}$ to $10^{-7}$ M which are well within the proper range for affinity chromatography and close to those found for the Protein A and A2P resins.

TABLE 5

Parameters Kd and qm obtained using double reciprocal curve (DR) as well as a direct fit of the Langmuir isotherm to the raw data (Lauqmuir).

|  | SEQ ID No | $K_d$, M | | $q_m$, mg/g | |
|---|---|---|---|---|---|
|  |  | DR curve | Langmuir | DR curve | Langmuir |
| A2P* | — | 3.38E-07 | 3.87E-07 | 30.1 | 35.1 |
| HWRGWV | SEQ ID NO: 4 | 2.80E-06 | 1.33E-06 | 54.8 | 50.0 |
| Protein A | — | 6.16E-07 | 4.32E-07 | 74.1 | 88.1 |
| WHWRKR | SEQ ID NO: 7 | 2.47E-06 | 1.39E-06 | 81.9 | 62.4 |
| YYWLHH | SEQ ID NO: 8 | 2.15E-07 | 2.97E-07 | 95.1 | 113.4 |

TABLE 5-continued

Parameters Kd and qm obtained using
double reciprocal curve (DR) as well as
a direct fit of the Langmuir isotherm
to the raw data (Laugmuir).

| SEQ ID | $K_d$, M | | $q_m$, mg/g | |
|---|---|---|---|---|
| No | DR curve | Langmuir | DR curve | Langmuir |

*The unit of binding capacity of A2P is mg/ml because A2P was provided as a slurry and measured in volume. Protein A Sepharose CL-4B came as a dry product and the capacity is given in mg protein/g resin.

Figure 4:
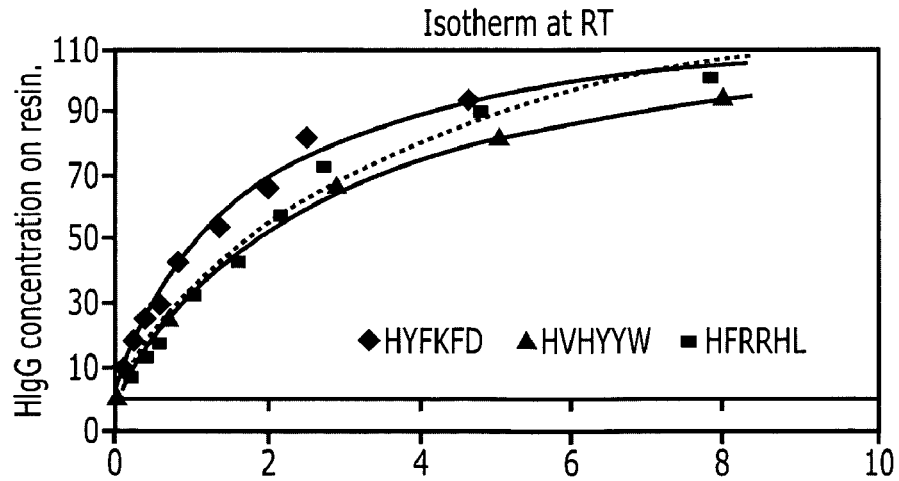
FIG. 4. Langmuir fits of isotherms for HIgG adsorption to HYFKFD (SEQ ID NO: 11), HVHYYW (SEQ ID NO: 12), and HFRRHL (SEQ ID NO: 21).

Adsorption isotherms of HYFKFD (SEQ ID NO: 11), HFRRHL (SEQ ID NO: 21), and HVHYYW (SEQ ID NO: 12). The isotherms of ligands HYFKFD (SEQ ID NO: 11), HVHYYW (SEQ ID NO: 12), and HFRRHL (SEQ ID NO: 21) are shown in FIG. 4. The lines represent the best Langmuir fit for each set of data points. The substitution level of these three resins is 0.1 meq/g. The concentration of HIgG adsorbed on the solid phase keep increases with increasing HIgG concentration in solution, up to values of 8 mg/ml. The dissociation constants of these three ligands are in the range of $10^{-5}$ M (Table 6), approximately 10 times higher than that of HWRGWV (SEQ ID NO: 4) at a substitution of 0.1 meq/g. Therefore, the binding of HIgG to these three ligands (HYFKFD (SEQ ID NO: 11), HVHYYW (SEQ ID NO: 12), and HFRRHL (SEQ ID NO: 21)) is weaker than to HWRGWV (SEQ ID NO: 4) at the same peptide density. The maximum binding capacity values listed in Table 6 are in the range of 130-160 mg/g, approximately twice that of HWRGWV (SEQ ID NO: 4), shown in Table 5. Since the surface area of the resin is approximately 30 m²/g and a monolayer of human IgG (235×44×44 Å) (Fair and Jamieson, *J. of Colloidal and Interface Science*, 7(2): 525-534 (1980)) may have a density of approximately 2.4-13 mg/m², it is likely that a monolayer of antibody should exhibit a maximum binding capacity of roughly 72-390 mg/g. The maximum capacities measured for the peptides in Tables 5 and 6 are in this range. It is possible that these peptides are forming a monolayer of bound protein, a phenomenon that has been seen previously with the adsorption of other proteins such as fibrinogen to peptide resins.

TABLE 6

Parameters Kd and qm obtained using a
direct fit of the Langmuir isotherm to
the raw data (Langmuir).

| Ligand | SEQ ID No | $q_m$, mg/g | $K_d$, M |
|---|---|---|---|
| HYFKFD | SEQ ID No: 11 | 126.8 | 1.14E-05 |
| HVHYYW | SEQ ID No: 12 | 129.0 | 2.03E-05 |
| HFRRHL | SEQ ID No: 21 | 157.9 | 2.64E-05 |

Figure 5:
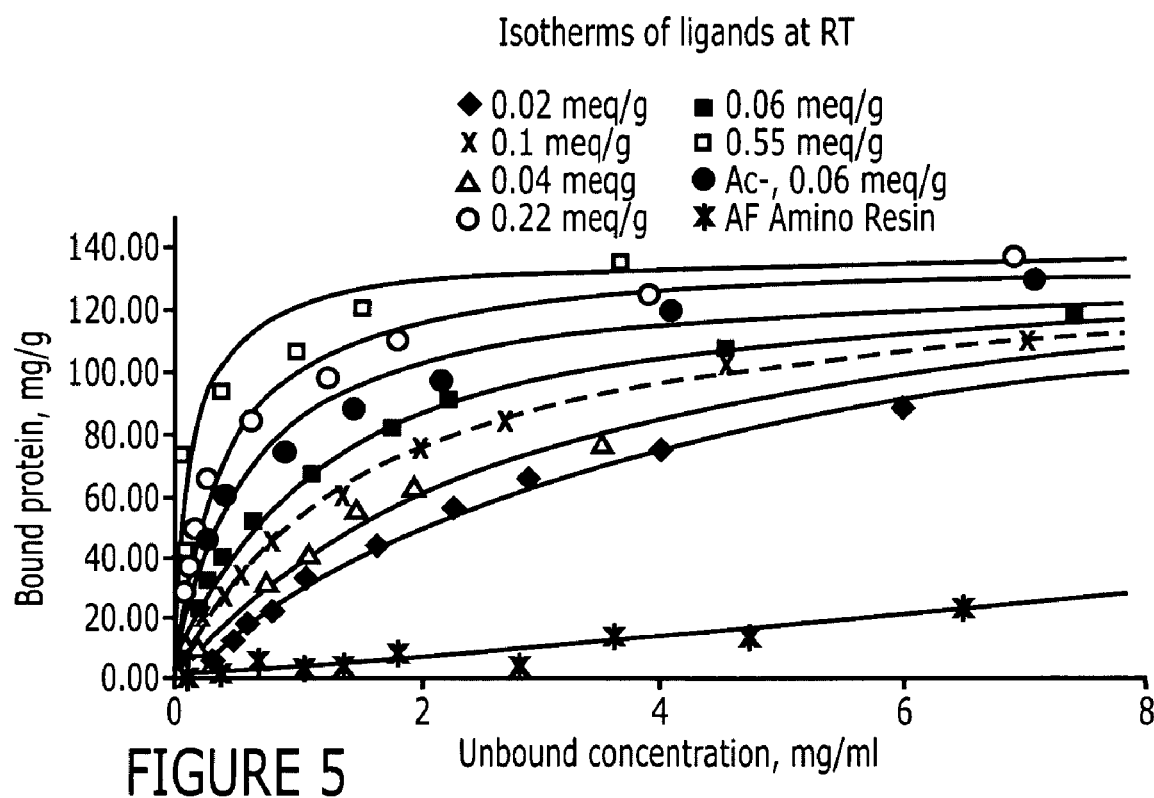
FIG. 5. Effect of peptide density on the adsorption of HIgG to HWRGWV (SEQ ID NO: 4). Experimental data were measured in batch experiment in PBS at pH 7.4
Figure 6A:
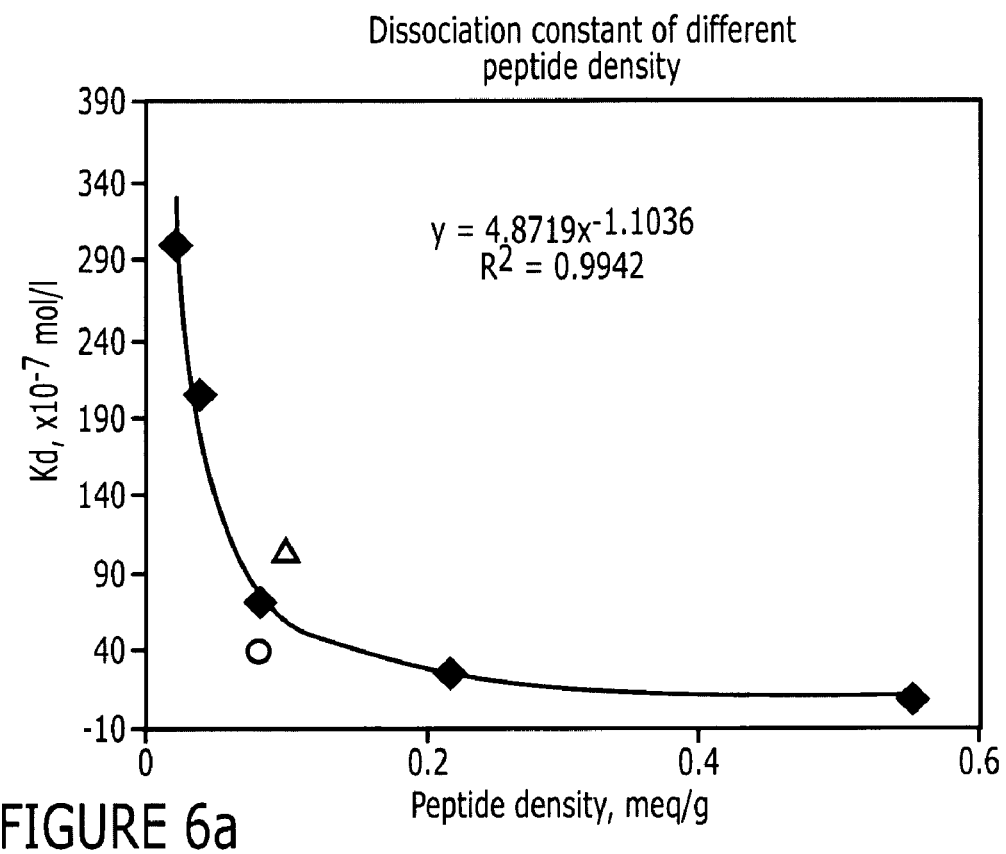
FIG. 6. Effect of peptide density on the capture of HIgG from HWRGWV (SEQ ID NO: 4). The triangles represent the data of 0.1 meq/g substitution synthesized in a batch different from others, while the circles are the data of Ac-HWRGWV (SEQ ID NO: 4).
Figure 6B:
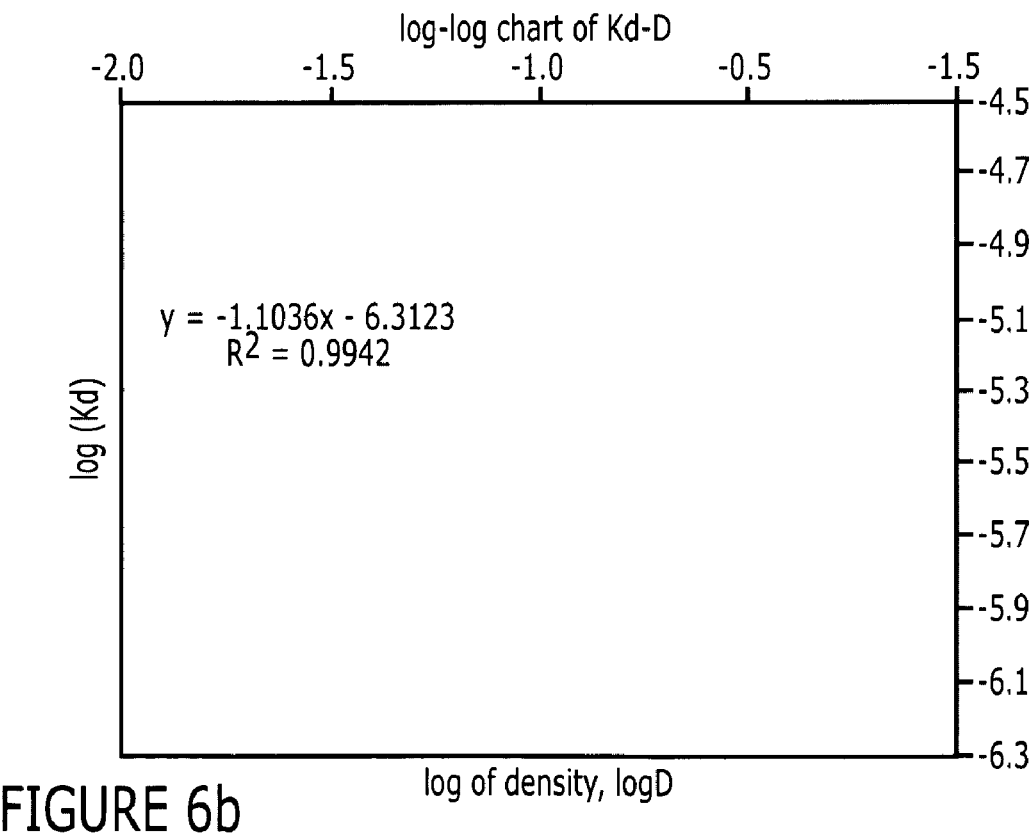

Adsorption isotherms of HWRGWV (SEQ ID NO: 4) with different substitutions. All substitutions of HWRGWV (SEQ ID NO: 4) ligand were weighed in dry powder and equilibrated in PBS overnight. The effect of peptide density on the adsorption isotherms at room temperature is shown in FIG. 5. The Langmuir equation was used to fit the isotherms in FIG. 5. The maximum binding capacities (qm) and dissociation constants (Kd) obtained from these isotherm curves are listed in Table 7.

In Table 7, "Ac-" denotes the acetylated HWRGWV (Ac-HWRGWV) (SEQ ID NO: 4) where the N-terminal amine group was acetylated with acetic acid to eliminate the charge of the terminus. Table 7 shows a general trend of increased maximum binding capacities and decreased dissociation constants with increasing peptide density, except for the resin with a substitution density of 0.1 meq/g. This resin was synthesized at a different time from the others shown in FIG. 5 and Table 7, using the same solid phase chemistry. Since the number of sequence errors in peptide synthesis can vary from batch to batch, this might account for the difference in trends with this particular resin. The correlation coefficients for the Langmuir fits to the isotherm data are very good when the peptide densities are equal to or less than 0.1 meq/g but they do not fit as well at higher peptide substitutions (data not shown). It is interesting to note that Ac-HWRGWV (SEQ ID NO: 4) binds HIgG approximately as well as HWRGWV (SEQ ID NO: 4) does, indicating that the terminal H amino group has little influence in binding and that the rest of the peptide has the ability to bind HIgG. HWRGWV (SEQ ID NO: 4) and its acetylated form exhibit maximum binding capacities of 130 mg/g (Table 7).

The results in Table 7 also indicate the stoichiometry of binding of HIgG to resins of different substitutions. At low peptide densities, the ratio of ligand to protein at the maximum capacity is approximately 21, while at the highest peptide density the ratio is approximately 600. Since the strength of interaction is increasing with increasing peptide density this is indicative that there is a multipoint interaction between the ligands the protein on the surface.

TABLE 7

Effect of peptide density and acetylation on the maximum capacity
($q_m$) and dissociation constant ($K_d$)

| Substiturions, mmol/g | $q_m$, mg/g | $K_d$, M | peptide/protein, mol/mol |
|---|---|---|---|
| 0.022 | 158.1 | 3.00E-05 | 21 |
| 0.040 | 147.8 | 2.03E-05 | 41 |
| 0.080 | 131.8 | 7.25E-06 | 91 |
| 0.080, Ac— | 130.8 | 3.80E-06 | 92 |
| 0.10 | 133.6 | 1.04E-05 | 112 |
| 0.22 | 136.8 | 2.58E-06 | 241 |
| 0.55 | 137.6 | 9.47E-07 | 600 |

Example 12

Chromatographic Separation of HIgG from MEM

Figure 7:
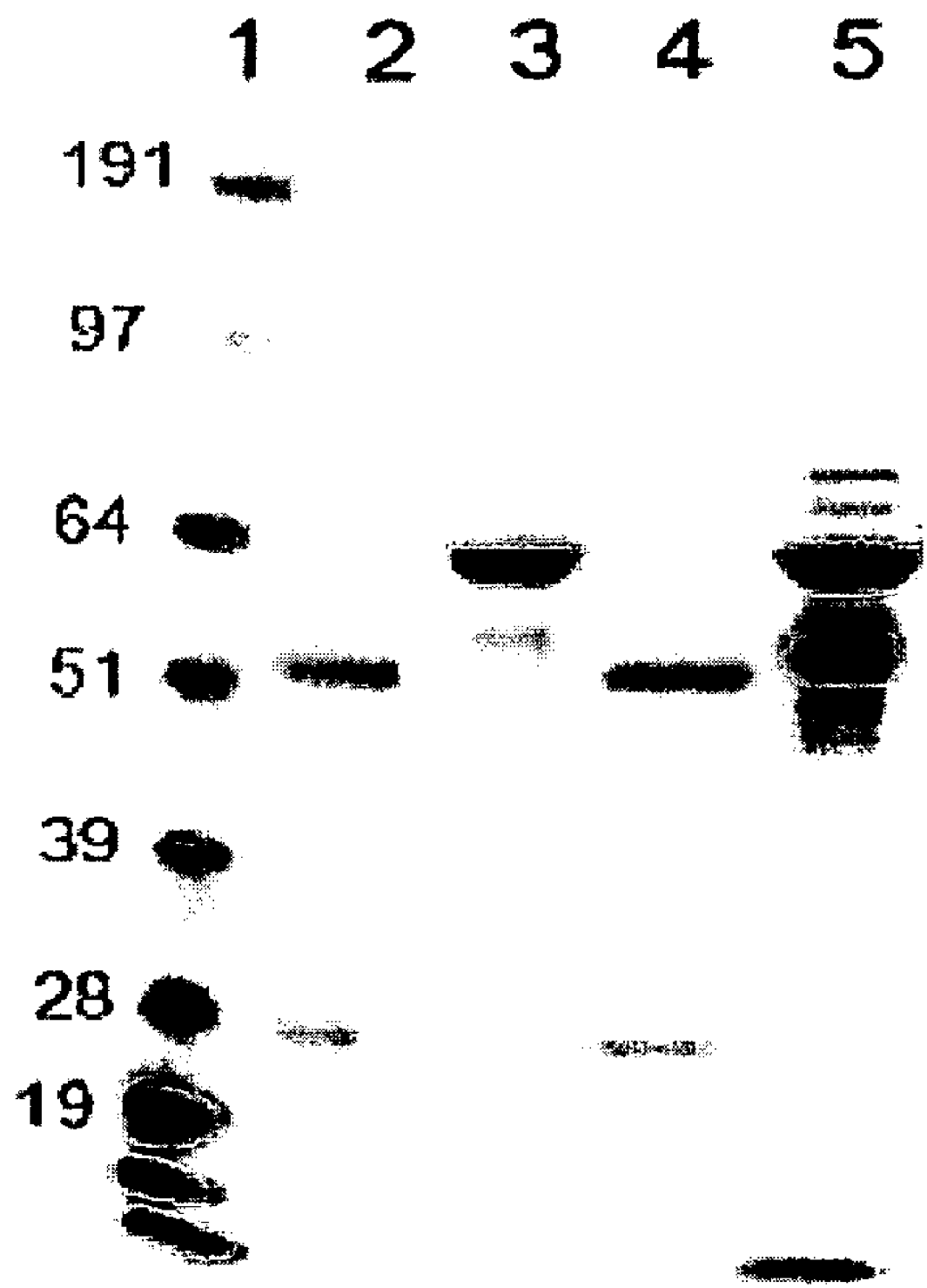
FIG. 7. Protein compositions of MEM analyzed by SDS-PAGE stained by SimpleBlue. Lane 1: molecular marker; Lane 2: HIgG standard (1 µg loaded); Lane 3: BSA standard (0.8 µg loaded); Lane 4: BIgG standard (1 µg loaded); Lane 5: 20% MEM.

HIgG contains a large number of different antigen specific antibodies and subclasses of IgG. At the same time, the competitive medium used in this study, MEM, is also a complex mixture of proteins, peptides, vitamins and other nutrients, containing 10% fetal calf serum (FCS) and 5% tryptose phosphate broth (TPB). FCS consists of serum proteins, with a large amount of serum albumin, a small amount of immunoglobulins (including Bovine IgG), transferrin, and lipoproteins (J. Harris, *Blood Separation and Plasma Fractionation*, John Wiley & Sons, New York, 325p (1990)). Tryptose is an enzymatic protein digest, consisting of a large number of peptide fragments. FIG. 7 is an SDS-PAGE gel of MEM. The BSA band at molecular weight of 64 kD dominates the MEM lane (lane 5). The band at 51 kD is probably a mixture of a small amount of Bovine IgG (BIgG) and some unknown proteins. The absence of a strong band at 28 kD indicates that MEM may contain some BIgG but at a very low level. Besides those bands, there are still large numbers of other proteins present in MEM. Therefore, attempting to purify HIgG in one-step using affinity chromatography from such a mixture is a difficult challenge due to the potential competition from nonspecific binding of other species.

Example 13

Chromatography on HWRGWV

Figure 8:
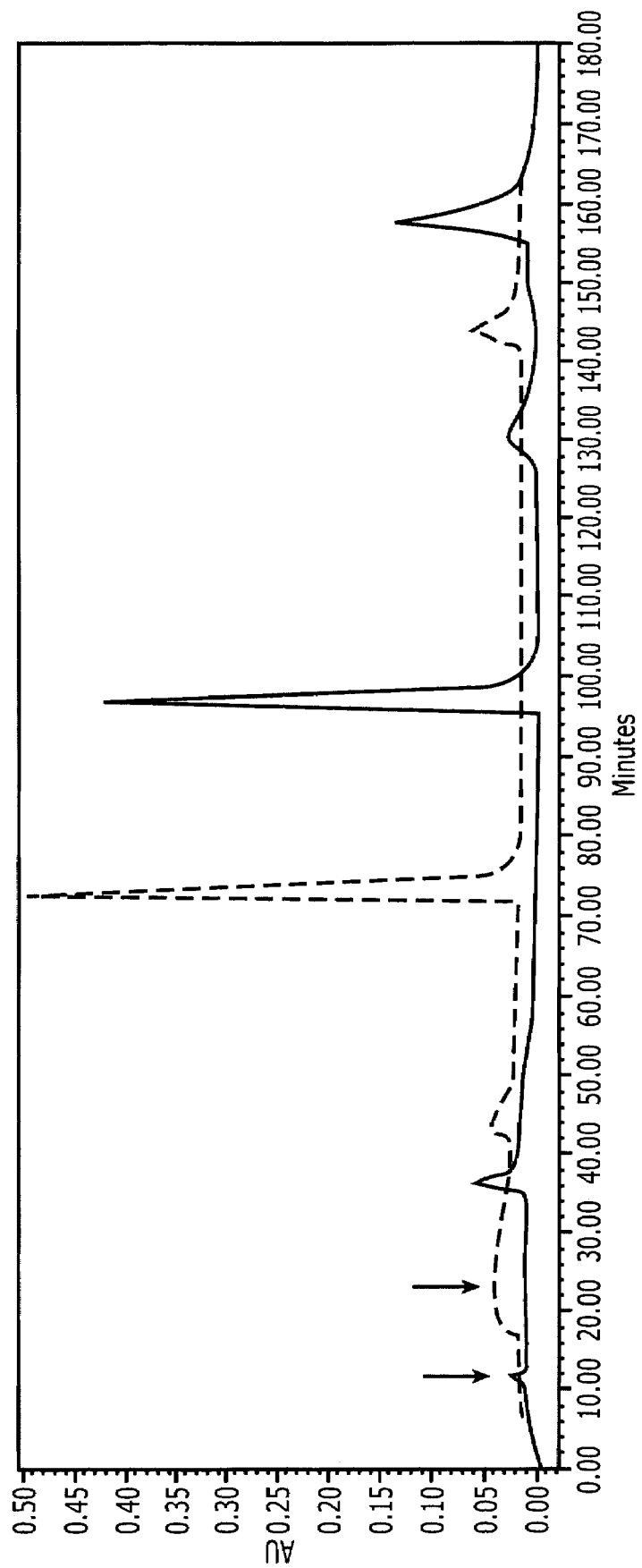
FIG. 8. Effect of salt concentration in loading buffer on the binding of HIgG to HWRGWV (SEQ ID NO: 4). Solid line: pure HIgG was loaded in PBS with 0.138M NaCl. Wash conditions are: 30-90 minutes: 0.5 M NaCl; 90-110 minutes: pH 6 PB; 110-130 minutes: pH 5 PB; 130-150 minutes: pH 4 PB; 150-180 minutes: 2% acetic acid. Dashed line: pure HIgG was loaded in PBS with 0.3M NaCl. Wash conditions are: 30-60 minutes: 0.5M NaCl; 60-80 minutes: pH 6 PB; 80-105 minutes: pH 5 PB; 105-130 minutes: pH 4 PB; 130-160 minutes: 2% acidic acid.

One lead (HWRGWV (SEQ ID NO: 4)) was selected from the first round of secondary screening for additional studies of chromatographic performance. To obtain a good separation of HIgG from MEM, different loading, washing and elution conditions were tried by changing salt concentrations, buffer systems, and pH values. PBS with 0.138M NaCl at pH 7.4 was used as the primary loading buffer. This is close to the buffer conditions normally found in the supernatant of mammalian cell culture. To study the effect of salt on the adsorption of HIgG to HWRGWV (SEQ ID NO: 4), the NaCl concentration in the loading buffer was increased to 0.3M. With the increase of the salt concentration, the binding of HIgG to HWRGWV (SEQ ID NO: 4) decreased resulting in a much broader flow through peak (see peaks with arrows, FIG. 8). Note that in both cases a majority of the HIgG was eluted using pH 6 phosphate buffer (PB).

Figure 9:
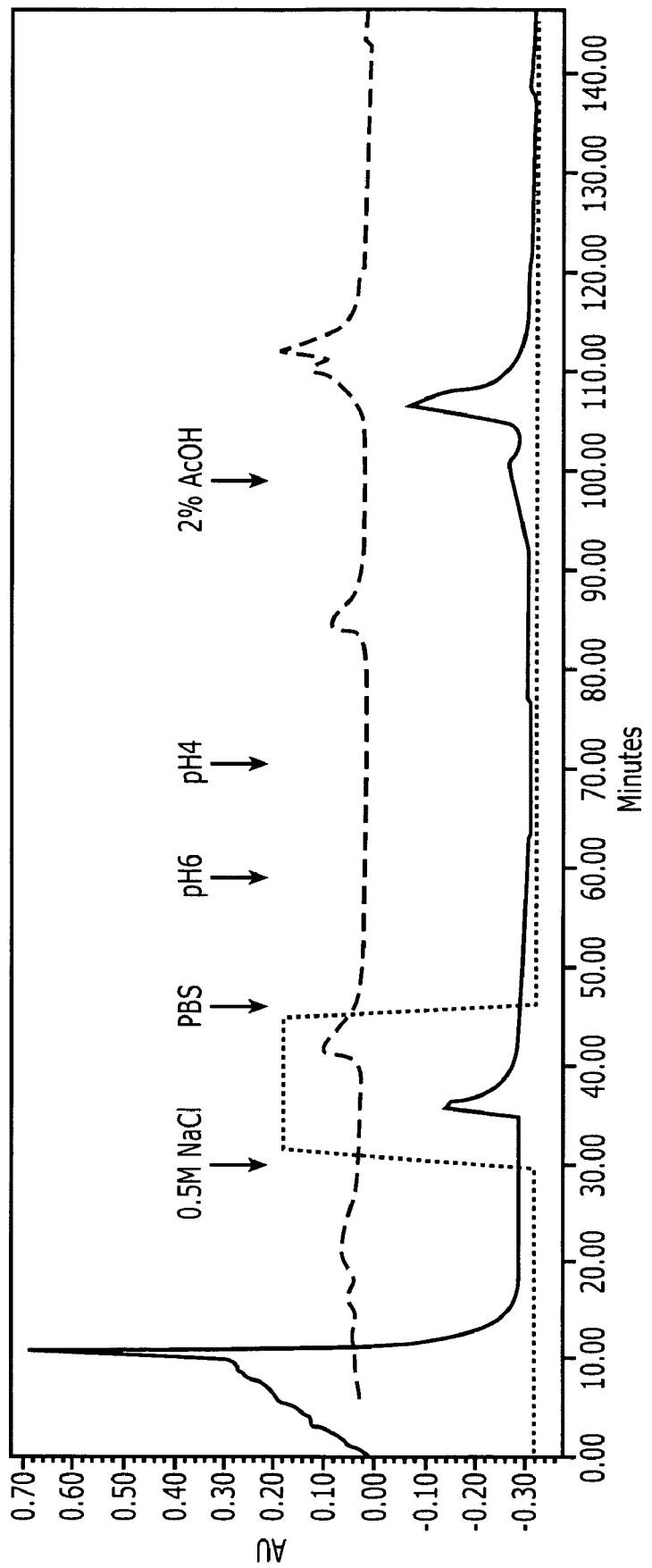
FIG. 9. Effect of loading pH on absorbance of HIgG on HWRGWV (SEQ ID NO: 4). Samples were loaded at pH 7.8 PBS, washed sequentially with 15 minutes of each PBS, PBS with 0.5M NaCl, pH 6 PB and pH 4 PB, and the column was then cleaned with 2% acetic acid. Dashed line: pure HIgG at 5 mg/ml in PBS; solid line: MEM without human IgG. Dotted line indicates the salt gradient.

When the pH of the loading PBS buffer was increased from 7.4 to 7.8, the binding strength was enhanced (FIG. 9). HIgG was not eluted until the pH was decreased to 4 in PB. This compares to the results in FIG. 8 where HIgG loaded into the column at pH 7.4 was eluted at pH 6. MEM exhibited a high flow through peak of unbound proteins at the higher pH of 7.8, but similar results are evident at pH 7.4 (not shown). Compared to the solid line in FIG. 8, corresponding to the pH 7.4 loading at low salt concentration, more HIgG was eluted in 2% acidic acid when the material was loaded at pH 7.8. This might be due to some denaturation of the protein at the higher pH.

Figure 10A:
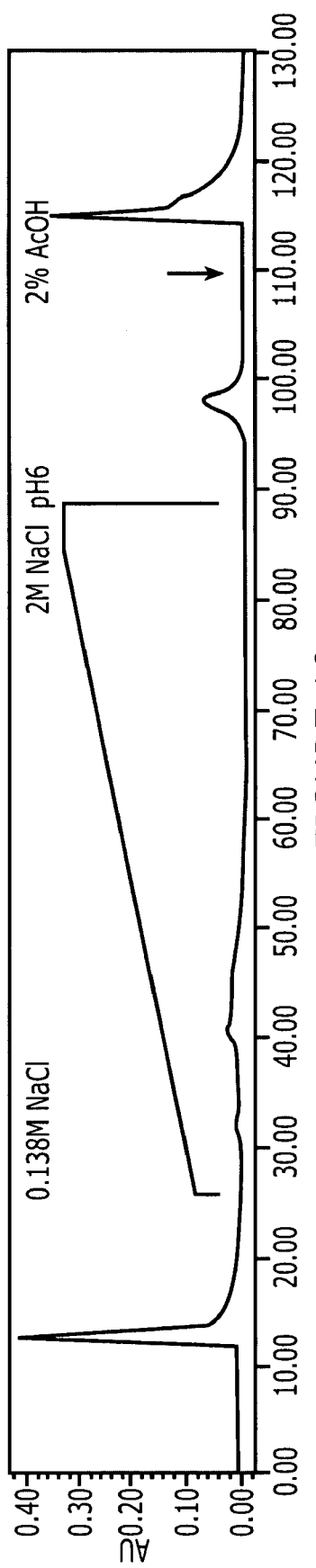
FIG. 10. Elution of HIgG with linear gradient of salt concentration from 0.138M-2M NaCl during 25-85 minutes. Samples were loaded in 10 mM PBS containing 0.138 M NaCl, pH 7.4 and eluted using pH 6 phosphate buffer. The column was cleaned with 2% acetic acid. (a) Injection of MEM with 1.5 mg/ml HIgG. (b) Injection of 1.5 mg/ml pure HIgG.
Figure 10B:
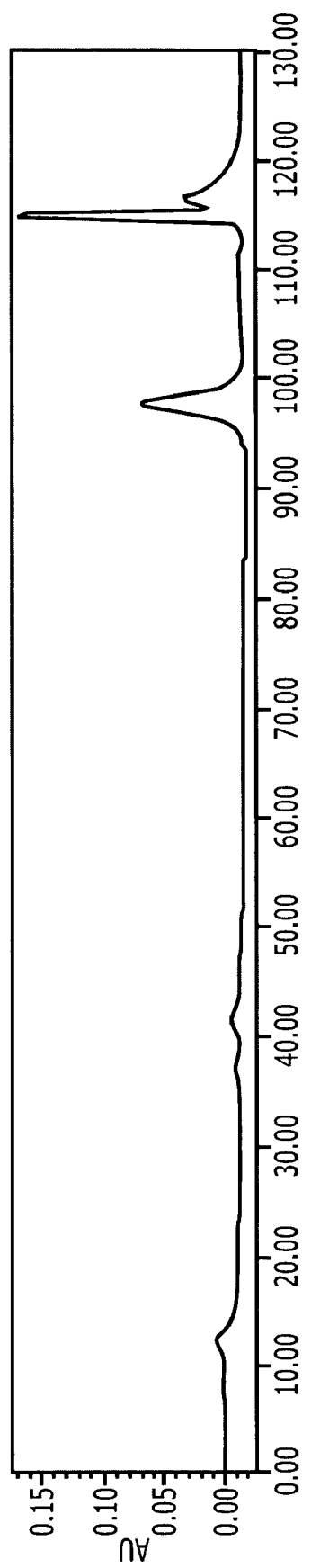

FIG. 10 shows an attempt at elution of HIgG on HWRGWV (SEQ ID NO: 4) at high salt concentration. In this case, HIgG was loaded into the column at low salt and low pH in PBS (10 mM, 0.138 M NaCl, pH 7.4) and it is clear that increasing the salt concentration even to 2M NaCl in PBS resulted in almost no elution. MEM, similar to the results indicated in FIG. 9, exhibited a large flow through peak of unbound proteins, but little material was eluted in high salt concentration. As can be seen, a portion of the HIgG was eluted in pH 6 phosphate buffer (PB) and the remainder in 2% acidic acid. The pH 6 elution peak in FIG. 10 seems smaller than the peak eluted with 2% acetic acid, as compared to the results shown in FIG. 8. It is possible that the exposure of bound protein to high salt concentrations can enhance hydrophobic interactions with the resin, making it more difficult to elute the bound HIgG.

Figure 12:
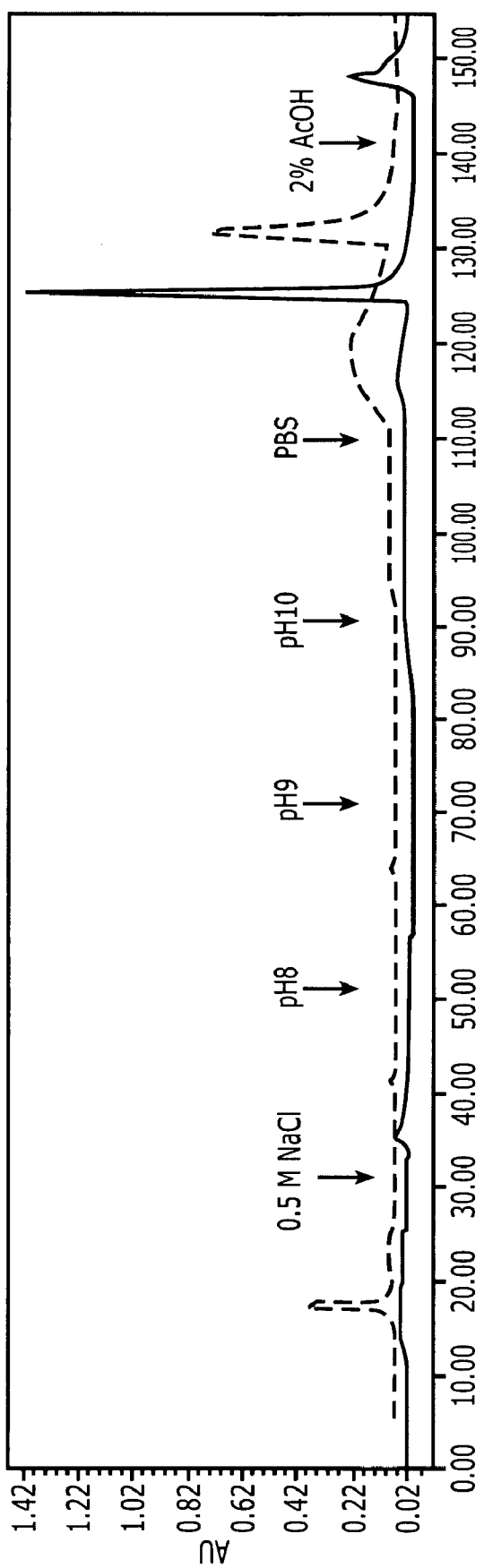
FIG. 12. Effect of higher pH elution on separation of HIgG from MEM. Loading was done at pH 7.4 in PBS buffer, washing was begun at 50 minutes using phosphate buffer at pH of 8, 9 and 10, each for 15 minutes. The column pH was then lowered to pH 7.4 for 10 minutes and then cleaned with 2% acetic acid. Solid line: 5 mg/ml pure HIgG in PBS; dashed line: 5 mg/ml HIgG in MEM.

To examine the effect of pH on the elution of HIgG, phosphate buffers (PB) with different pH values were employed (FIG. 11 and FIG. 12). In FIG. 11 we show a case where samples of pure HIgG and HIgG spiked in MEM were loaded on an HWRGWV (SEQ ID NO: 4) column in loading buffer at pH 7.4 and low salt. The columns were then eluted with pH 6, 5 and 4 PB. It was observed that most of the HIgG (54%) came off the column with pH 6, 7% with pH 5 and little with pH 4. This chromatogram suggests that HIgG can be eluted in a very mild pH condition which is an advantage to maintain the biological properties of HIgG.

The results in FIG. 12 indicate that increasing the elution pH from 7.4 to values as high as 10 does not yield any separation. Interestingly, though, HIgG was eluted when the buffer pH was lowered to 7.4 in PBS. Neither HIgG nor any of the MEM proteins elute under these conditions. Clearly, basic pH values result in strong adsorption of all of the major components to the resin. These results indicate that the adsorption process is largely controlled by charge-charge interactions since HIgG and most of the MEM proteins are negatively charged at pH values greater than 8 and the ligand HWRGWV (SEQ ID NO: 4) is positively charged at all pH between 7 and 10. However, as was seen in FIG. 10, HIgG cannot be eluted with 2M NaCl. This indicates that even though the HIgG and MEM proteins have to have the proper charge to bind to the resin, the binding is not completely dominated by charge-charge interactions. As is usual with peptide resins, the binding is the result of a combination of charge and hydrophobic interactions.

Figure 13A:
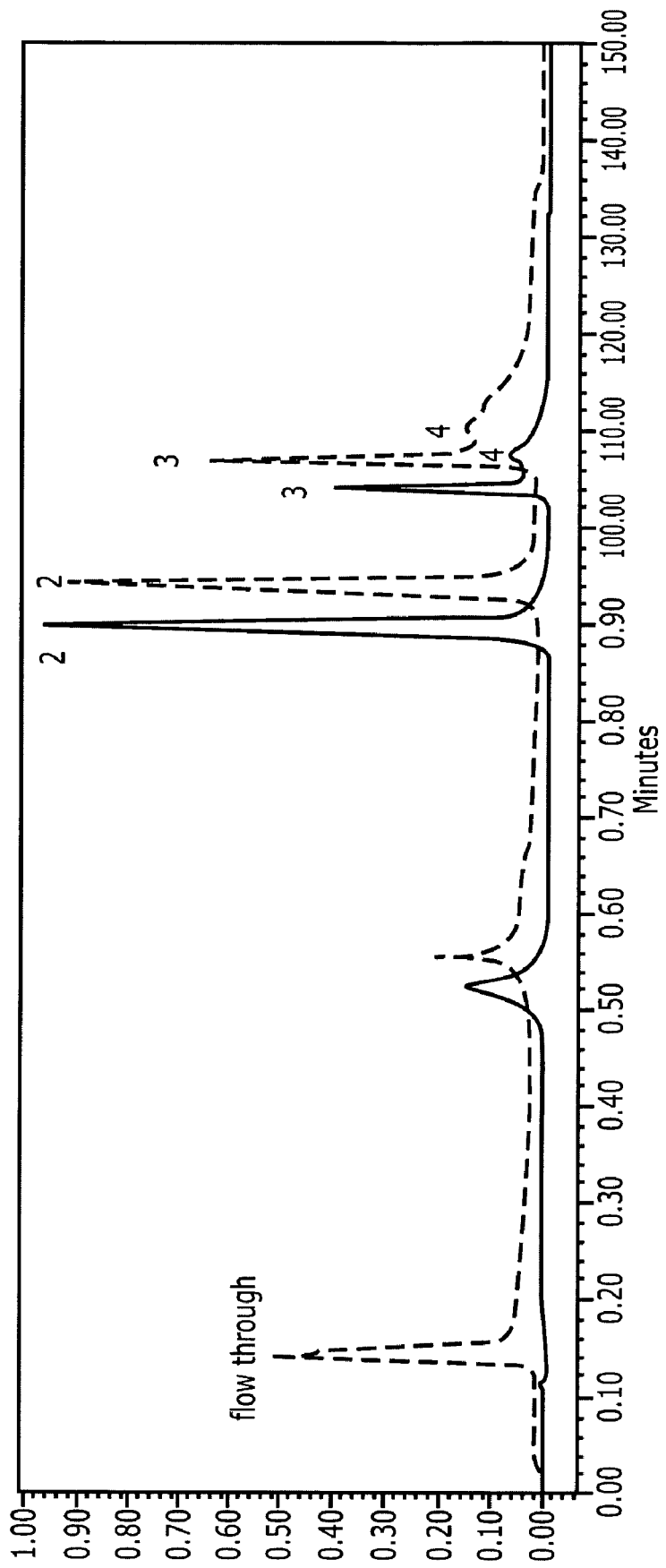
FIG. 13. Effect of sodium acetate on separation of HIgG from MEM. Samples were loaded in PBS at pH 7.4, washed with a linear gradient of 0-0.3 M sodium acetate during 30-60 minutes. HIgG was eluted at about 80 minutes with acetate buffer at pH 4, and the column was cleaned with 2% acetic acid. The flow rate was 0.2 ml/min. Solid line: 5 mg/ml pure HIgG in PBS; dashed line: MEM with 5 mg/ml HIgG. (a) Chromatogram of HIgG purification. (b) SDS-PAGE profiles of the separation denoted in (a) stained by silver and SimpleBlue, respectively. Lane 1: molecular marker; lane 2: HIgG standard; lane 3: BIgG standard; lane 4: 20% MEM; lane 5: MEM without FCS; lane 6: the flow through of the pure HIgG injection; lanes 7-9: peaks 1, 2, 3 and 4 of the pure HIgG injection, respectively. Lanes 10-14 correspond to the flow through, and peaks 1-4 of the MEM injection containing 5 mg/ml HIgG. The volumes of the collected peaks were not same. Gels were run under reducing conditions.
Figure 13B:
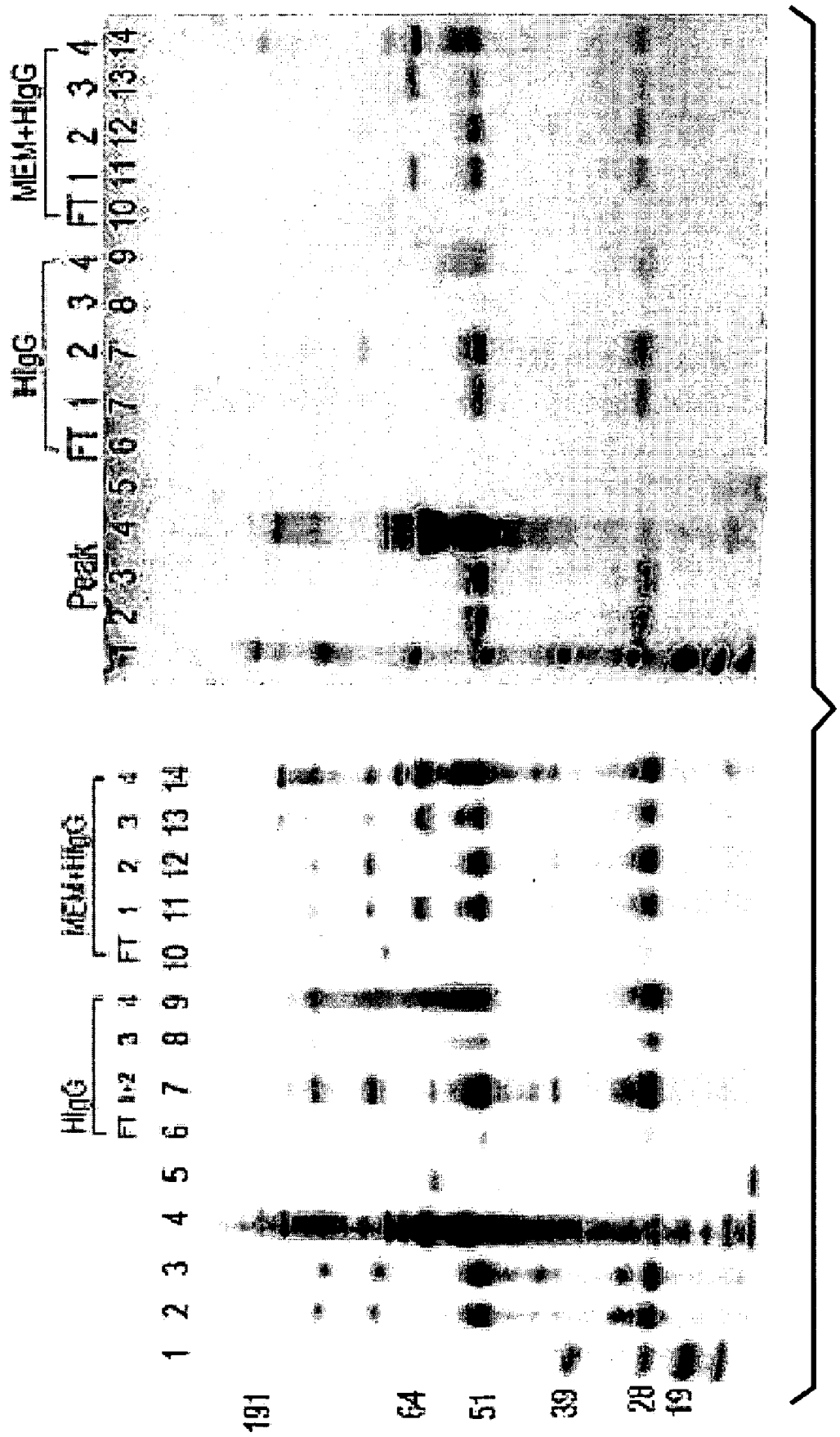

The effect of using acetate as a wash and elution buffer is shown in FIG. 13. In this case the proteins were loaded at pH 7.4 in PBS and a gradient of acetate was used to wash the column, followed by a pH 4 acetate buffer elution. Note that the peak with the highest HIgG concentration, obtained by the pH 4 elution, contains almost no BSA. This is lane 12 in the gels shown in FIG. 13b. The yield of HIgG according to the peak area in this particular peak of the chromatogram is about 26.7% but it seems to be nearly pure HIgG. HIgG is also present in the high acetate wash and the 2% acetic acid wash, but this material contains more BSA than the pH 4 elution peak. It is not clear what the role of acetate is in affecting this separation but it does suggest that acetate buffer might be a good elution medium for this separation.

Figure 14A:
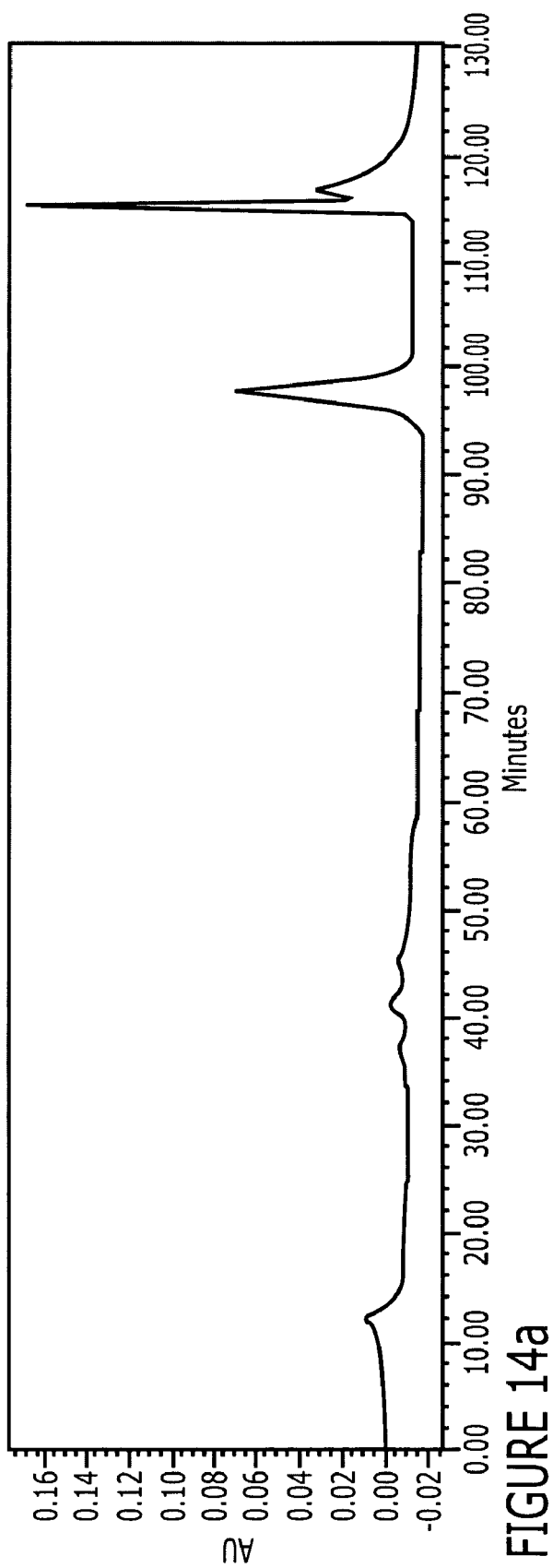
FIG. 14. Effect of different buffer system on separation of HIgG from MEM. Samples were loaded at pH 7.4 in both PBS and citrate buffer, and sequentially washed with linear gradients from 30 to 85 minutes using NaCl concentrations from 0.138 M to 2 M in PBS or 0 M to 2M in citrate. The 2M NaCl condition was maintained for 5 minutes, at which time the pH was changed to 4 in both PB and citrate buffers and maintained for 20 minutes. The columns were then washed with 2% acetic acid. (a) PBS buffer system; (b) citrate buffer system.
Figure 14B:
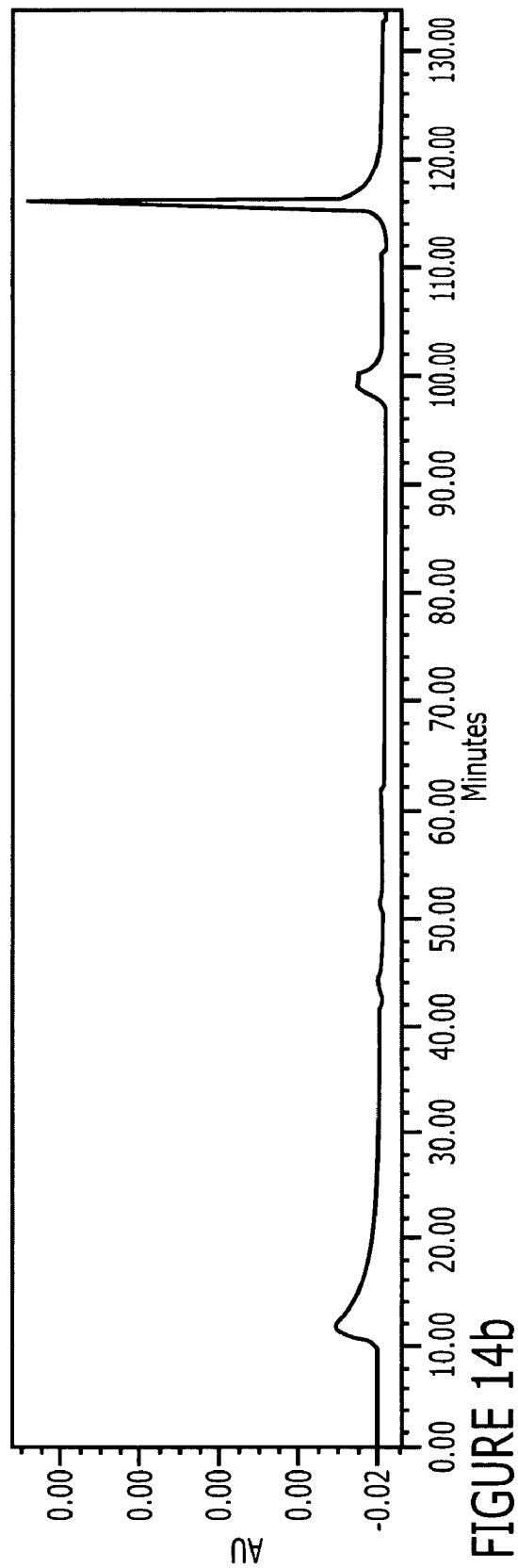

Additional experiments on the effect of the buffer were carried out by comparing salt washes and pH 4 elution results in phosphate buffer (PB) to citrate buffer. The results are shown in FIG. 14. Clearly, HWRGWV (SEQ ID NO: 4) exhibits stronger binding in citrate buffer than in PBS since HIgG can only be eluted more efficiently at pH 4 in PBS and not in citrate. As a result of these experiments with acetate and citrate it was decided that the PB system is the best to use for separations at this time since it leads to the best combination of ease of elution and purity.

Several runs of the purification of HIgG from MEM were carried out to test reproducibility. We also used these examples to quantify by densitometry the purity and yield of the resulting HIgG. The results are shown in FIG. 15. For these experiments, the MEM and HIgG solution was loaded in PBS at pH 7.4. Elution was carried out using a 0.5 M NaCl wash in PB, followed by a change to pH 4. The column was washed using 2% acetic acid. FIG. 15a shows the chromatograms obtained with injections using pure HIgG. Clear elution peaks show up under pH 4 with little material being eluted at 0.5 M NaCl and in the acetic acid wash. The gel in FIG. 15c clearly confirms that peak 3 in the chromatogram in FIG. 15a contains most of the injected HIgG mixture.

Figure 15B:
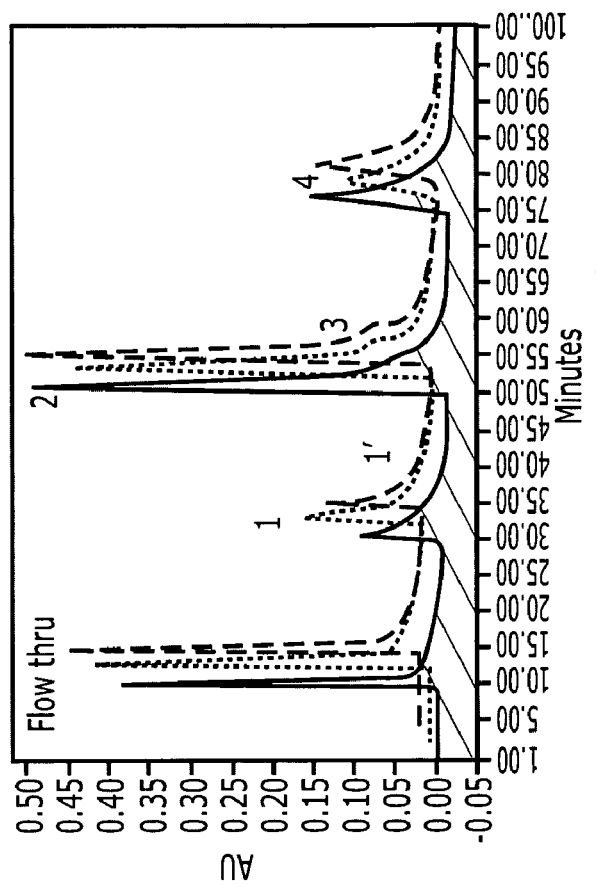
FIG. 15. Separation of HIgG from MEM using pH 4 PB. Samples were loaded in PBS at pH 7.4, washed with 0.5 M NaCl for 20 minutes from 25-45 minutes. HIgG was eluted at about 50 minutes with PB at pH 4, and the column was cleaned with 2% acetic acid. The flow rate was 0.4 ml/min. (a) Chromatogram of 5 mg/ml pure HIgG in PBS on HWRGWV (SEQ ID NO:4) (three repetitions). (b) Chromatogram of MEM with 5 mg/ml HIgG on HWRGWV column (SEQ ID NO:4) (three repetitions). (c) SDS-PAGE of the separation denoted in (a) and (b). Lane 1: molecular marker; lane 2: HIgG standard; lane 3: BSA standard; lane 4: BIgG standard; lane 5: 20% MEM; lane 6:1:50 dilution of loading material (MEM+HIgG); lanes 7-11 correspond to the flow through, peaks 1, 2, 3 and 4 of pure HIgG injection (a), respectively. Lanes 12-17 correspond to the flow through, peaks 1, the tail of peak 1, peak 2, 3 and 4 of chromatogram (b), respectively. The volumes of the collected peaks were adjusted to same. The gel was run under reducing condition. (d)-(h) are the densitometer profiles of SDS-PAGE gel in (c): (d) plot of 1:50 dilution of loading material (MEM+HIgG) (lane 6); (e) plot of peak 2 with pure HIgG injection (lane 10); (f) plot of peak 2 with mixture of MEM and HIgG injection (lane 15); (g) plot of standard HIgG lane (lane 2); (h) plot of 20% MEM standard (lane 5).
Figure 15A:
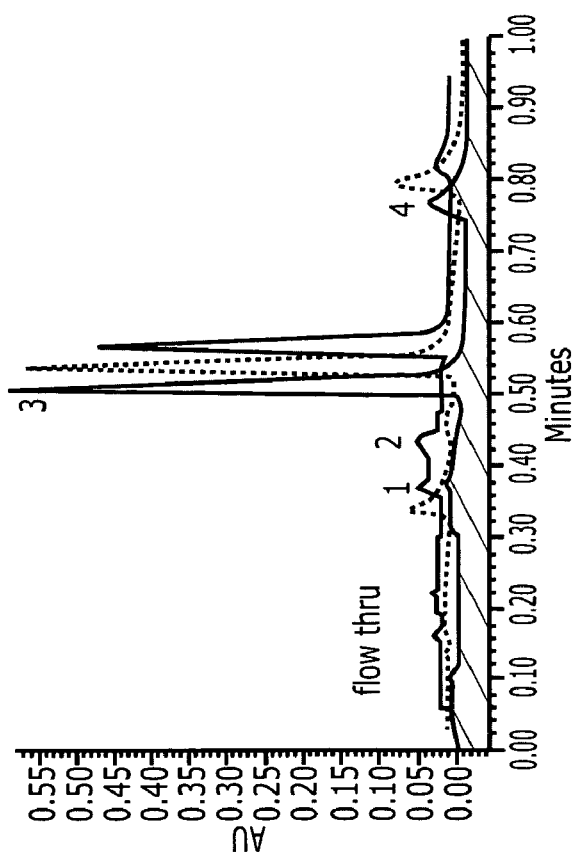

FIG. 15b shows the chromatogram of the mixture injection of MEM and HIgG. There is evidence of a significant flow through peak that contains MEM proteins as well as larger peaks obtained from 0.5 M NaCl wash and the 2% acetic acid wash. There is also some evidence of broadening of the pH 4 elution, indicating the potential co-elution of MEM proteins together with HIgG components. The SDS-PAGE gels in FIG. 15c clearly indicate that most of the BSA present in MEM came out in peak 1 of FIG. 15b. The "shoulder peak" 1' also contained some HIgG. The gels also indicate that peak 2 contained the majority of the HIgG along with a relatively small amount of BSA.

Figure 15C:
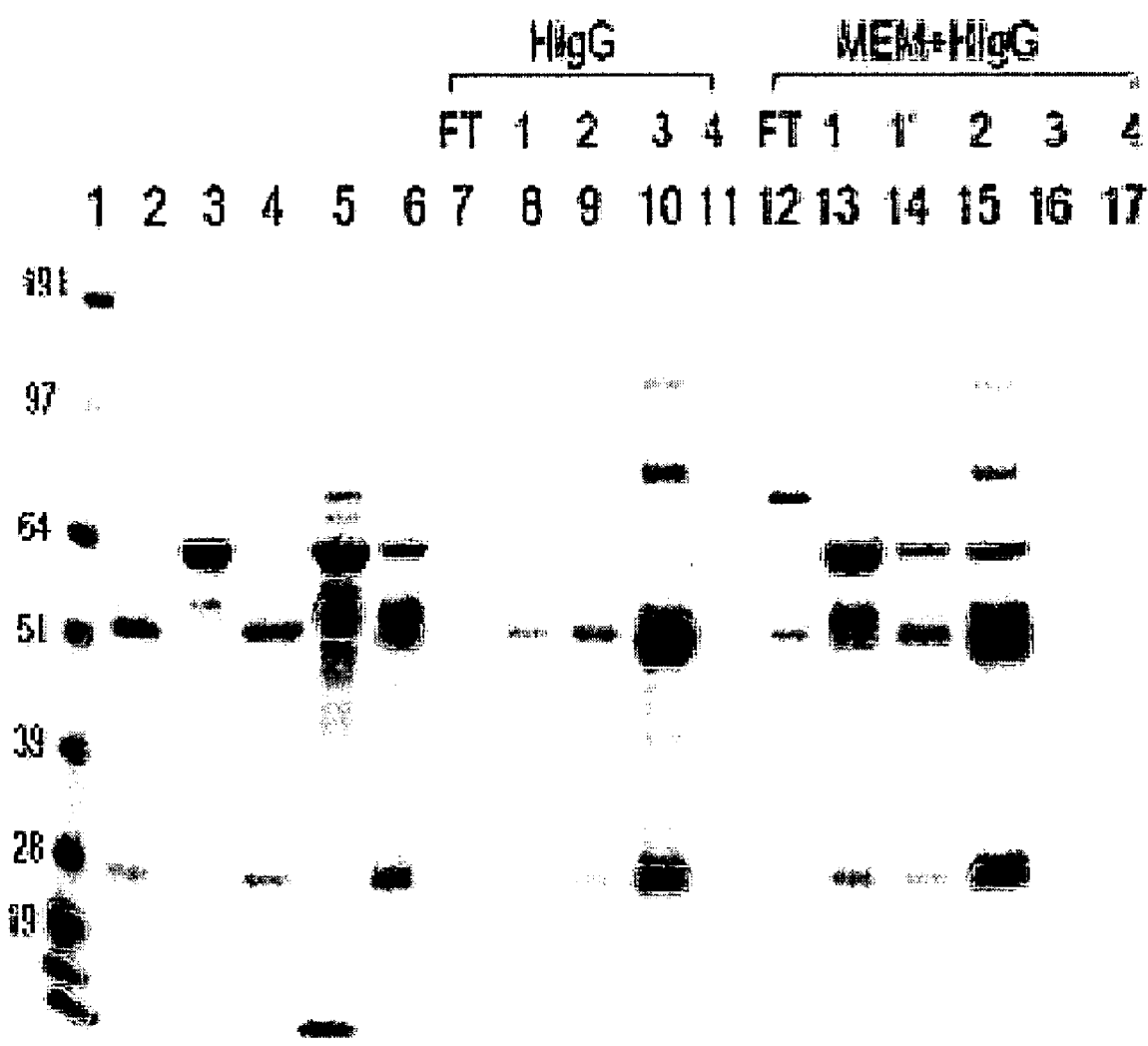
Figure 15D:
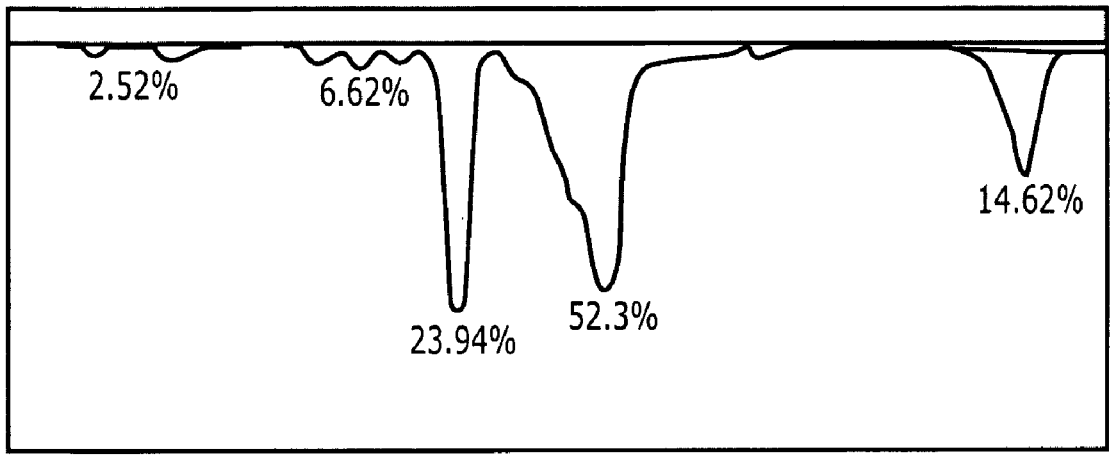
Figure 15E:
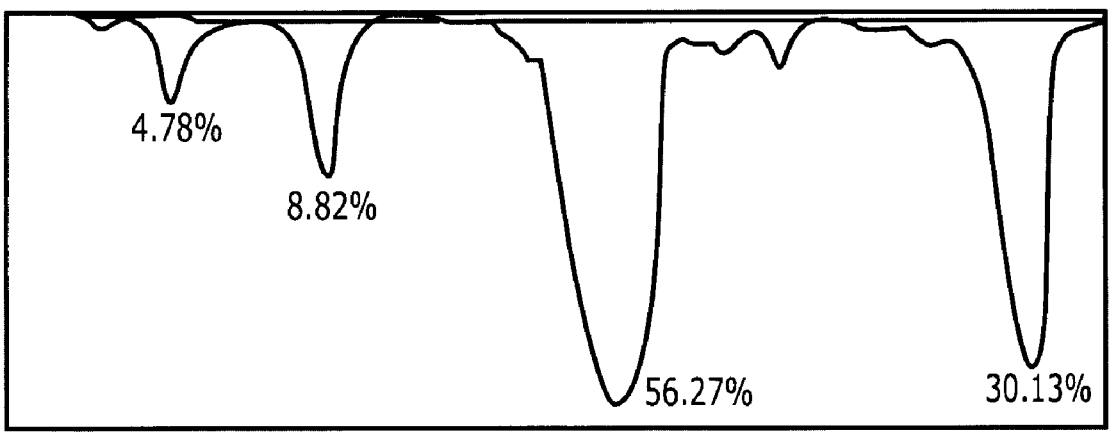
Figure 15F:
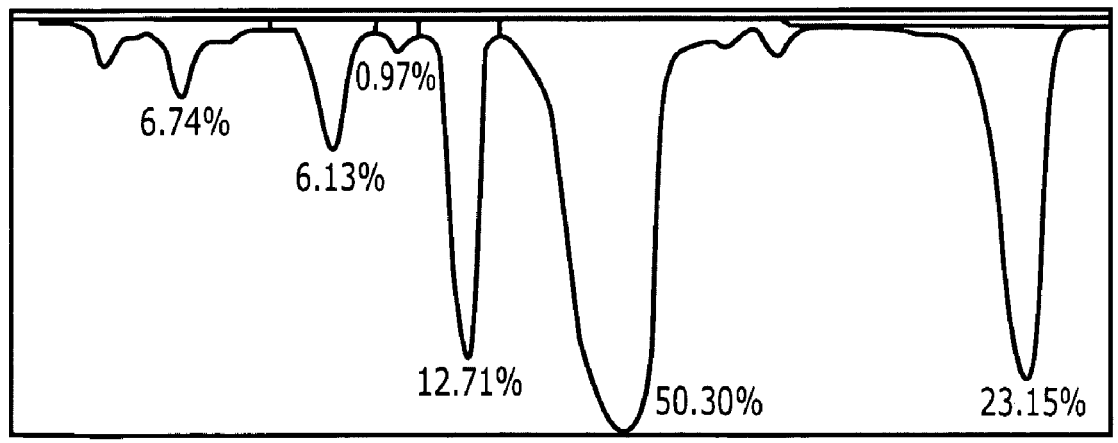
Figures 15G, 15H:
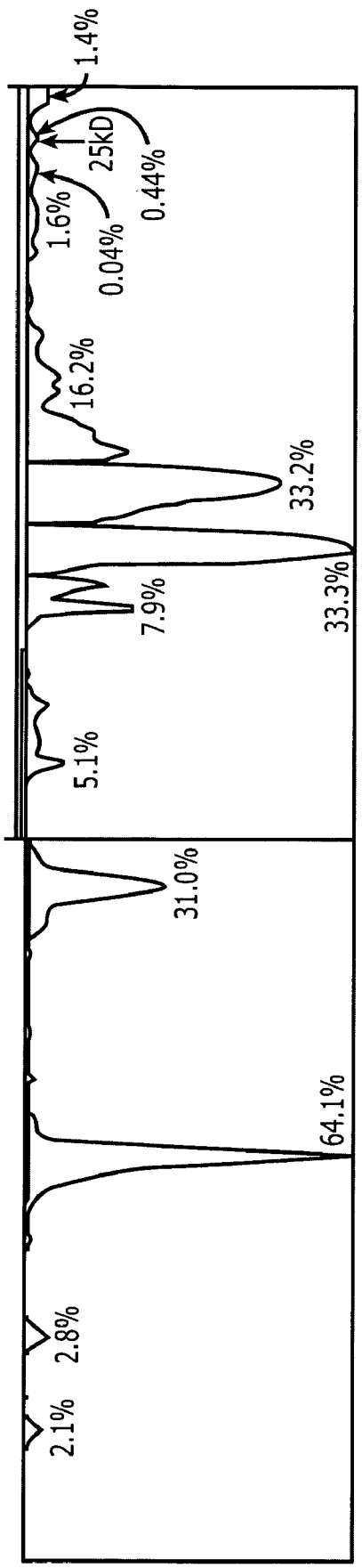

FIG. 15d-h shows the densitometry analyses of lanes 6, 10, 15, 2, and 5 of the gels shown in FIG. 15c. The areas associated with the various peaks in the densitometry plots are shown in Table 8 and Table 9. Comparison of FIG. 15e and FIG. 15f clearly shows the presence of BSA in peak 2 of the mixture elution at pH 4. FIG. 15h shows that the area percentage of the MEM band at 25 kD is only 0.44%, indicating that the 25 kD bands in all lanes come only from HIgG. As a result, we used the 25 kD band as the standard lane in making estimates of the purity and the yield.

In Table 8, the HIgG 25 kD peak in lane 2, corresponding to the pure HIgG standard, is 31% of the total area. The HIgG 25 kD peak for pure HIgG is 31% of the total area. This indicates that the percentage of HIgG in lane 15, corresponding to the pH 4 elution of MEM with HIgG, is roughly 75% (23/31). The BSA peak in lane 15 corresponds to 12.7% of the total area. As a result it is possible to estimate that the ratio of HIgG to BSA in lane 15 is approximately 6:1 (75/12.7). The ratio of HIgG:BSA in the injected material is about 1.6:1 since the ratio of the HIgG 25 kD area to the BSA area in lane 6 (23.9/112.3).

TABLE 8

Percentage of the area of each band in the SDS-PAGE gel lanes 2, 6, 10 and 15 (FIG. 15 (c)). Band 1 and 2 are the aggregated IgG; bands 3 and 7 are not identified. The HIgG percentage was calculated according to 25 kD HIgG band.

| Densitometer profile | Lane | | | |
|---|---|---|---|---|
| | 2 (g) | 6 (d) | 10 (e) | 15 (f) |
| 1 | 21 | 3.5 | 4.8 | 6.7 |
| 2 | 2.8 | 5.5 | 8.8 | 6.1 |
| 3 | | | | 1.0 |
| BSA (64 kD) | | 23.9 | | 12.7 |
| HIgG (52 kD) | 64.1 | 52.4 | 56.3 | 50.3 |
| HIgG (25 kD) | 31.0 | 14.6 | 30.1 | 23.1 |
| Percentage of HIgG | 100 | 47.2 | 97.2 | 74.7 |

Table 9 shows that the area corresponding to the HIgG peak at 25 kD in all the lanes (lanes 12-17), from flow through to peaks 1-4, adds up to 6,757 units. The area of HIgG (25 kD) in the product peak 2 is 4,616. We can hence approximate the yield of HIgG as 68% (4616/6757).

TABLE 9

Area of each band in SDS-PAGE gel MEM + HIgG lanes (FIG. 15c). The first row is the peaks corresponding to the chromatogram (FIG. 15b). The yield was calculated according to the 25 kD HIgG bands.

| Peak | FI | 1 | 1' | 2 | 3&4 |
|---|---|---|---|---|---|
| 1 | | 188 | 174 | | |
| 2 | 1260 | 170 | 95 | 2733 | |
| BSA (64 kD) | 219 | 4892 | 1479 | 2511 | 216 |
| HIgG (52 kD) | 1159 | 4160 | 2171 | 9209 | |
| 3 | | | | 557 | |
| HIgG (25 kD) | 366 | 1016 | 759 | 4616 | |
| 4 | | | | 100 | |
| Yield of HIgG | | | | | 68% |

Figure 16:
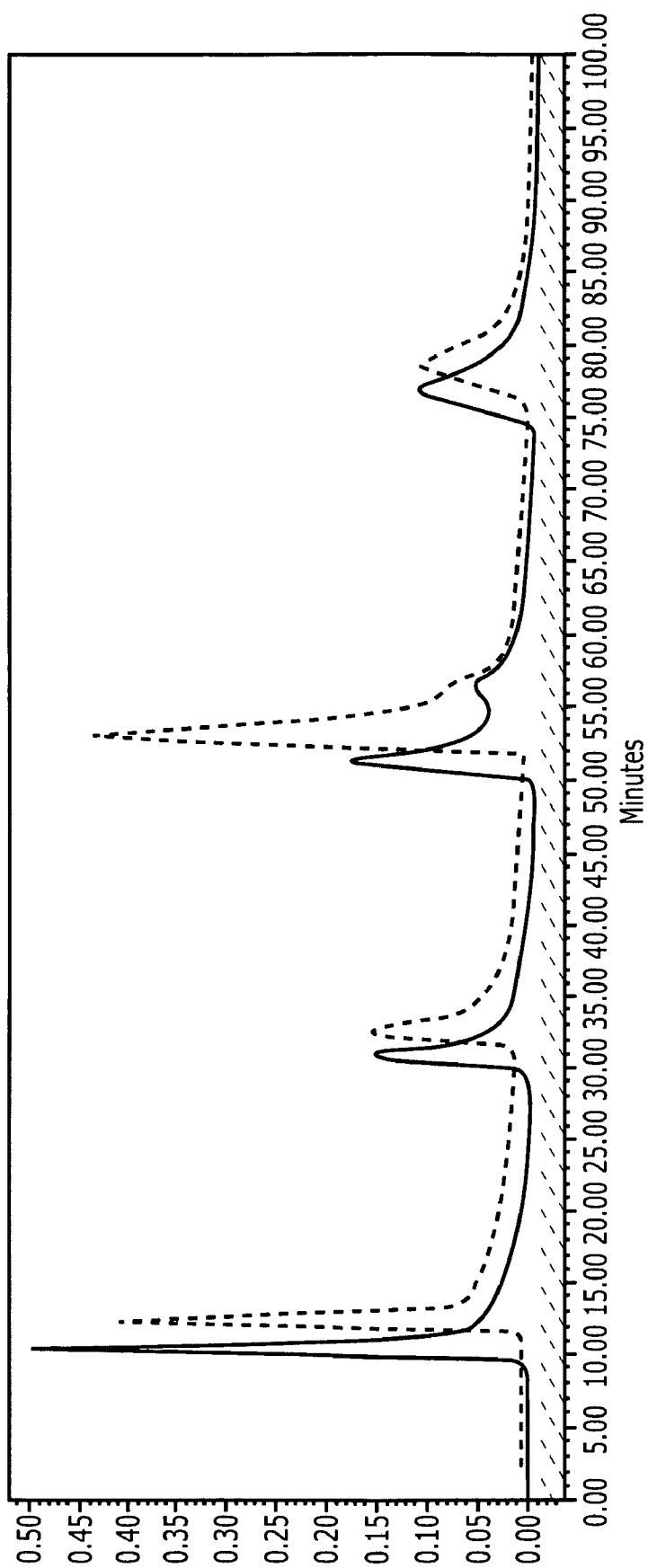
FIG. 16. Effect of different HIgG concentration on separation of HIgG from MEM. Samples were loaded in PBS at pH 7.4, washed with 0.5 M NaCl for 20 minutes from 25-45 minutes. HIgG was eluted at about 50 minutes with PB at pH 4, and the column was cleaned with 2% acetic acid. The flow rate was 0.4 ml/min. Solid line: 1.5 mg/ml HIgG in MEM; dashed line: 5 mg/ml HIgG in MEM.

The concentration of monoclonal HIgG in cell culture supernatant is anywhere between 0.1-2 mg/ml. To meet this purpose, the separations of MEM with different HIgG concentrations were compared (FIG. 16). The chromatogram profiles are the same, and the only difference is the significantly smaller elution peak at pH 4 PB. This result signifies that the profiles of HIgG separation at 5 mg/ml are applicable to the separation of HIgG at 1.5 mg/ml.

Example 14

Chromatography on HYFKFD (SEQ ID NO: 11), HFRRHL (SEQ ID NO: 21), HVHYYW (SEQ ID NO: 12), and YYWLHH (SEQ ID NO: 8)

Resins HYFKFD (SEQ ID NO: 11), HFRRHL (SEQ ID NO: 21), and YYWLHH (SEQ ID NO: 8) were packed dry and equilibrated in PBS for at least 12 hours (minimum of 10 column volumes). Resin HVHYYW (SEQ ID NO: 12) was also packed dry, but was submitted to a 20% methanol wash before rinsing with PBS. The chromatographic conditions for these four ligands were same. Samples were injected using a 100 μl sample loop, followed by a 30 minute wash step using PBS. Weakly bound proteins were washed off using a 0.14-1.14 M linear sodium chloride gradient for 30 min trailed by a 5-minute wash step at the high salt concentration. Human IgG was eluted using phosphate buffer (PB) pH 4.0 for 30 minutes and the column was cleaned by using a 2% acetic acid solution for another 30 min. Peaks were collected from the beginning of each peak until the signal returned to baseline level, with a maximum of 2 ml/fraction, which led to some peaks being divided into two fractions. The split peaks are coded FT11 and FT12, or P11 and P12, while P2 is used to denote the peak containing most of the HIgG from the elution with phosphate buffer pH 4.0.

The chromatogram of HYFKFD (SEQ ID NO: 11) (FIG. 17a) demonstrates that HIgG is mainly eluted in pH 4 PB (P2), while a small amount of HIgG is contained in both FT and P1. Higher salt concentrations can get rid of most BSA as indicated in lanes 9-11 (FIG. 17b). The observation of the small peak in the 2% AcOH wash (P3) shows that the HIgG binds HYFKFD (SEQ ID NO: 11) with great selectivity.

Figure 18A:
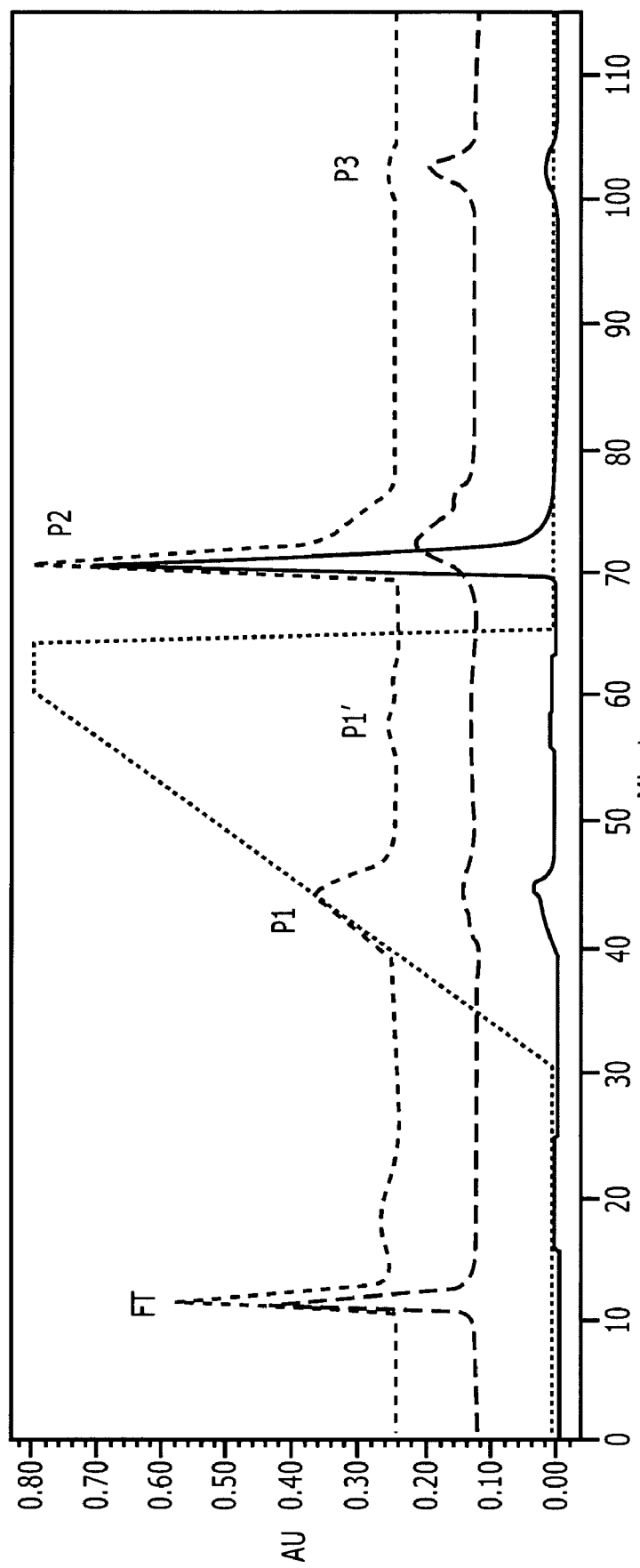
FIG. 18. Separation of HIgG from MEM on the HFRRHL (SEQ ID NO: 21) column. Samples were loaded in PBS at pH 7.4, washed with 0.14-1.14 M NaCl linear gradient for 30 minutes from 30-60 minutes. HIgG was eluted at about 70 minutes with PB at pH 4, and from 95 min the column was cleaned with 2% acetic acid. The flow rate was 0.4 ml/min. (a) Chromatogram of 5 mg/ml HIgG and/or MEM on HFRRHL (SEQ ID NO: 21). Dotted line: 5 mg/ml HIgG in MEM; dashed line: MEM; solid line: 5 mg/ml HIgG in PBS. Coomassie blue (b) and silver (c) stained SDS-PAGE of the separation denoted in (a). Lane 1: molecular marker; lane 2: HIgG standard; lane 3: BSA standard; lane 4: 20% MEM; lane 5: 1:50 dilution of loading material (MEM+HIgG); lanes 6-14 correspond to the flow through, peaks 1, 1', 2, and 3 of injections, respectively. FT2, P12 and P13, and P22 are the tails of peaks of FT, P1, and P2. Lanes 1-14 are under reducing condition. Lanes 15-17 are under non-reducing condition (no reducing agent in sample preparation). P21 (lane12) is the eluted HIgG peak in pH 4 PB.
Figures 18B, 18C:
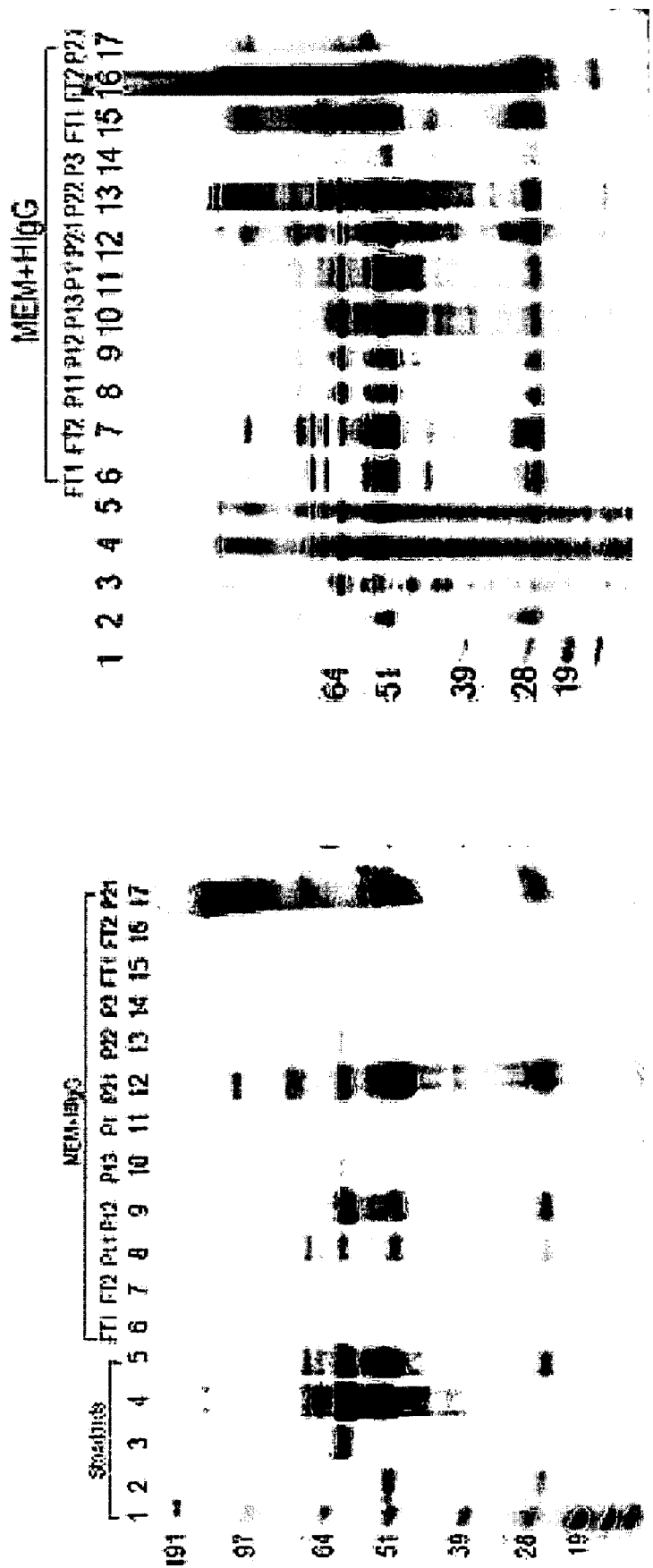

The ligand HFRRHL (SEQ ID NO: 21), binding approximately 41% HIgG in MEM (Table 4), can separate HIgG from MEM in a column format. The results are shown in FIG. 18. Most HIgG was retained until pH 4 PB elution. The separation profile is similar to that of HYFKFD (SEQ ID NO: 11) (FIG. 17a) but with larger P1 and smaller P1', which suggests that the electrostatic interactions between proteins and HFRRHL (SEQ ID NO: 21) are weaker than those between proteins and HYFKFD (SEQ ID NO: 11).

Figure 19A:
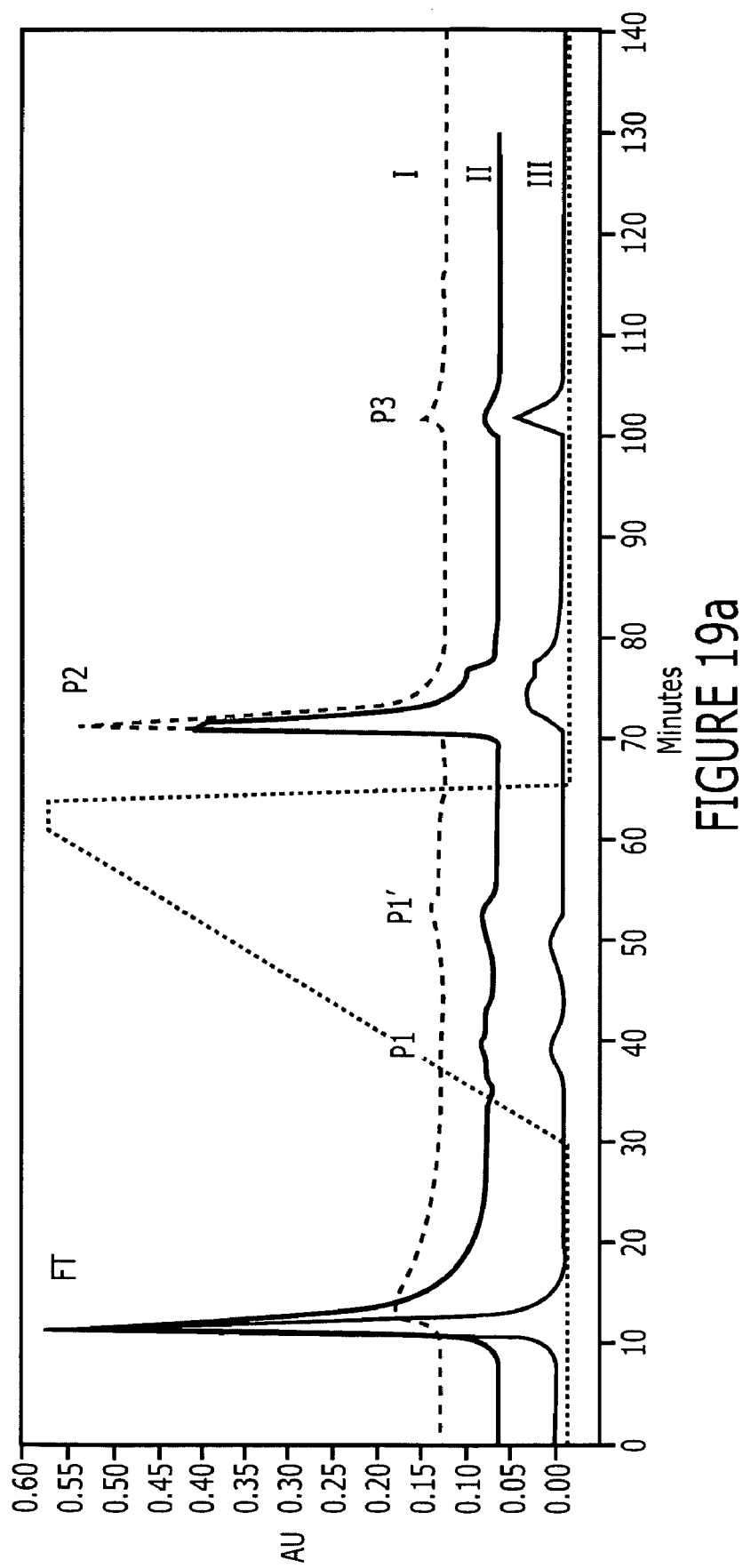
FIG. 19. Separation of HIgG from MEM on the HVHYYW (SEQ ID NO: 12) column. Samples were loaded in PBS at pH 7.4, washed with 0.14-1.14 M NaCl linear gradient for 30 minutes from 30-60 minutes. HIgG was eluted at about 70 minutes with PB at pH 4, and from 95 min the column was cleaned with 2% acetic acid. The flow rate was 0.4 ml/min. (a) Chromatogram of each sample on HVHYYW (SEQ ID NO: 12). Line I: 5 mg/ml HIgG in PBS; line II: 5 mg/ml HIgG in MEM; line III: MEM. Coomassie blue (b) and silver (c) stained SDS-PAGE gel, under reducing condition, of the separation denoted in (a). Lane 1: molecular marker; lane 2: HIgG standard; lane 3: BSA standard; lane 4: 20% MEM; lane 5: 1:50 dilution of loading material (MEM+HIgG); lanes 6-10 correspond to the flow through, peaks 1, 1', 2, and 3 of pure HIgG injections, respectively. Lanes 11-17 correspond to the flow through (FT), peaks 1, 1', 2, and 3 of MEM+HIgG injections, respectively. FT2 and P22 are the tails of peaks of FT and P2. P21 (lane 15) is the eluted HIgG peak in pH 4 PB, corresponding to P2.
Figures 19B, 19C:
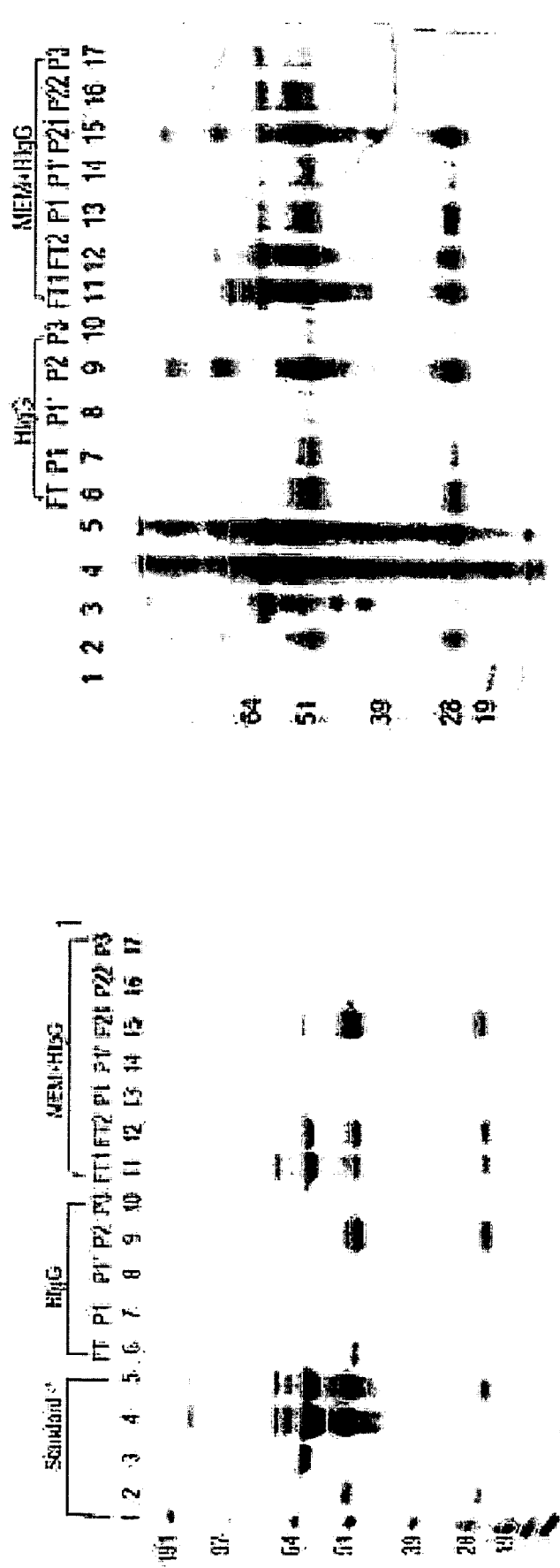

FIG. 19 is the chromatogram and SDS-PAGE profiles of ligand HVHYYW (SEQ ID NO: 12). HIgG is mainly eluted by pH 4 PB (P2). Compared to HYFKFD (SEQ ID NO: 11) and HFRRHL (SEQ ID NO: 21), HVHYYW (SEQ ID NO: 12) exhibits a larger flow through peak of pure HIgG (dotted line). This may indicate that the binding of HIgG to HVHYYW (SEQ ID NO: 12) is weaker or slower than to HYFKFD (SEQ ID NO: 11) and HFRRHL (SEQ ID NO: 21). This is consistent with the results of the isotherms. At the chromatographic protein concentration working range (approximately 5 mg/ml), the binding capacities of both HYFKFD (SEQ ID NO: 11) and HFRRHL (SEQ ID NO: 21) are larger than that of HVHYYW (SEQ ID NO: 12). With an injection concentration of 5 mg/ml, HYFKFD (SEQ ID NO: 11) and HFRRHL (SEQ ID NO: 21) capture more HIgG than HVHYYW (SEQ ID NO: 12) does. Furthermore, HYFKFD (SEQ ID NO: 11), with a higher association constant than HVHYYW (SEQ ID NO: 12), binds HIgG stronger than HVHYYW (SEQ ID NO: 12) does.

The chromatographic separation of HIgG from MEM on YYWLHH (SEQ ID NO: 8) column is showed in FIG. 20. The chromatograms are different from those obtained on HYFKFD (SEQ ID NO: 11), HFRRHL (SEQ ID NO: 21), and HVHYYW (SEQ ID NO: 12). HIgG was eluted mainly in P22 (lane 10), some in P23 (lane 11), and some in P3 (lanes 13 and 14) though the protein concentrations were too low to be seen in lanes 6-9. Also, smaller FT and larger 2% AcOH (P3) peaks signify that the binding of YYWLHH (SEQ ID NO: 8), not only to HIgG but to other contaminant proteins, is much stronger than other ligands. This is understandable because the YYWLHH (SEQ ID NO: 8) is not a ligand found by screening against HIgG. The binding specificity to HIgG is low even though the interaction is strong.

Example 16

Comparison of HWRGWV with Different Substitutions

The chromatograms of HWRGWV (SEQ ID NO: 4) at two substitutions, 0.55 and 0.1 meq/g, are shown in FIG. 21. The SDS-PAGE results at 0.1 and 0.55 meq/g substitution are shown in FIG. 15c and FIG. 21b, respectively. Larger P1 and smaller P2 (P21 and P22) peaks are observed in the lower 0.1 meq/g substitution. These differences in P1 and P2 confirm the isotherm finding that the binding of HIgG to HWRGWV (SEQ ID NO: 4) with higher peptide density is strengthened. The gel (FIG. 21b) also indicates that the HIgG was mainly eluted in P21 (lane 8) by pH 4 PB, though a slight amount was observed in P22 (lane 9) and P31 (lane 10). The splitting of the peak P2 into P21 and P22 suggests the possibility of a better separation of HIgG rich P21 and BSA rich P22.

Example 17

Purity and Recovery of Isolated HIgG

The recovery and the purity of HIgG peaks from different ligands are listed in Table 10. Except for samples HP28 and HF1, two sets of data are displayed. One is from the ELISA assay and another is from densitometer analysis using software "ImageJ" as explained in section 4.4.1. The data from ELISA and from ImageJ both demonstrate the same trend. HIgG ELISA displays no cross-reaction with bovine IgG (data not shown) so all the IgG identified is HIgG. The total protein concentration was detected by absorption at 280 nm. The standard curves of both A280 and ELISA assay are shown in Appendix II.

Comparing the ImageJ results to the first ligand identified, HWRGWV (SEQ ID NO: 4), the other four ligands, HYFKFD (SEQ ID NO: 11), HFRRHL (SEQ ID NO: 21), HVHYYW (SEQ ID NO: 12), and YYWLHH (SEQ ID NO: 8) yield higher purities of isolated HIgG but lower recovery value. It is evident that the HWRGWV (SEQ ID NO: 4) at 0.55 meq/g produced higher purity and recovery, of 80% and 77% by ELISA, than its 0.1 meq/g·substitution with comparison of the data achieved from ImageJ. This is consistent with their isotherms. Higher density results in higher binding amount and affinity to HIgG.

A noticeable ligand is HYFKFD (SEQ ID NO: 11) which isolated HIgG from MEM with a high purity of 90% and a recovery of 47.7% by both ELISA and ImageJ (HY2). The chromatogram and its SDS-PAGE gel are shown in FIG. 17. The chromatographic conditions of this ligand are subject to further optimization, which might produce even higher purity as well as higher recovery.

Different pretreatments of resin can also lead to different chromatographic separation results. As displayed in Table 10, runs HV2 and HY2 yielded better separation results than runs HV3 and HY1. HVHYYW (SEQ ID NO: 12) favored methanol swelling (HV2 and HV3) whereas HYFKFD (SEQ ID NO: 11) worked best without methanol swelling (HY1 and HY2). The chromatographic separations and the SDS-PAGE gels of runs HY2 and HV2 are shown in FIG. 17 and FIG. 19, respectively. The reason for this phenomenon has not been determined.

The chromatographic performance of ligands HYFKFD (SEQ ID NO: 11), HVHYYW (SEQ ID NO: 12), HFRRHL (SEQ ID NO: 21), YYWLHH (SEQ ID NO: 8), and HWRGWV (SEQ ID NO: 4) (0.55 meq/g) were also studied using 50 mM Tris buffered saline (TBS, Sigma) with 0.138 M NaCl in column formats. It was found that, for all ligands, the separation of HIgG from MEM in TBS system is not as good as in the PBS system (data not shown).

TABLE 10

The recovery and purity of HIgG separated from MEM on each ligand by chromatography.

| | ELISA assay | | ImageJ | | | | Note | |
|---|---|---|---|---|---|---|---|---|
| Runs | Rec, % | Purity, % | Rec, % | Purity, % | Ligand | SEQ ID No | MeOH swelled | Chromatographic conditions |
| HP28 | / | / | 74 | 68 | HWRGWV | SEQ ID No: 4 | No | 1-26**, PBS |
| HW2 | 80.28 | 76.85 | 73 | 73 | HWRGWV, 0.55 meq/g | SEQ ID No: 4 | No | 1-26**, PBS |
| HF1 | / | / | 76 | 78 | HFRRHL | SEQ ID No: 21 | No | 2-1*, PBS |
| HY1 | 37.47 | 75.10 | 39 | 82 | HYFKFD | SEQ ID No: 11 | Yes | 2-1, PBS |
| HY2 | 47.71 | 90.15 | 60 | 92 | HYFKFD | SEQ ID No: 11 | No | 2-1, PBS |
| HV2 | 29.95 | 89.59 | 53 | 84 | HVHYYW | SEQ ID No: 12 | Yes | 2-1, PBS |

TABLE 10-continued

The recovery and purity of HIgG separated from
MEM on each ligand by chromatography.

| | ELISA assay | | ImageJ | | | | Note | |
|---|---|---|---|---|---|---|---|---|
| Runs | Rec, % | Purity, % | Rec, % | Purity, % | Ligand | SEQ ID No | MeOH swelled | Chromatographic conditions |
| HV3 | 49.11 | 78.10 | 39 | 65 | HVHYYW | SEQ ID No: 12 | No | 2-1, PBS |
| YY1 | 59.18 | 75.83 | 47 | 76 | YYWLHH | SEQ ID No: 8 | No | 2-1, PBS |

*linear salt gradient washes off the weakly bound protein, pH 4 PB elutes HIgG.
**0.5 M NaCl washes off the weakly bound protein, pH 4 PB elutes HIgG.

That which is claimed is:

1. An immunoglobulin binding peptide that binds to the Fc region of an antibody selected from the group consisting of:
   (a) the peptide HWRGWV (SEQ ID NO: 4),
   (b) the peptide HYFKFD (SEQ ID NO: 11).
   (c) the peptide HFRRHL (SEQ ID NO: 21),
   (d) the peptide HVHYYW (SEQ ID NO: 12),
   (e) peptides of (a), (b), (c), or (d) having a linking group bonded to the C terminus thereof; and
   (f) peptides of (a), (b), (c), (d), or (e) having a capping group bonded to the N terminus thereof;
   and wherein the amino acids of said peptide are in L form.

2. The peptide of claim 1, wherein said capping group is selected from the group consisting of: $R^{10}CO-$, $R^{10}-O-CO-$, $R^{10}-PO-$, $R^{10}-SO_2-$, and arylalkyl; wherein $R^{10}$ is selected from the group consisting of H, alkyl, alkenyl, alkynyl, aryl, and arylalkyl.

3. The peptide of claim 1, wherein said capping group is selected from the group consisting of: acetyl, benzoyl, formyl, trifluoroacetyl, benzyloxycarbonyl, tert-butyloxycarbonyl, biphenylylisopropyloxycarbonyl, triphenylmethyl, o-nitrobenzenesulfenyl, and diphenyiphosplilnyl.

4. The peptide of claim 1, wherein said linking group is a chain of from 1 to 10 amino acids.

5. The peptide of claim 1, wherein said linking group is selected from the group consisting of polyethylene glycol, polypropylene glycol, polyesters, polypeptides, polyethers, and polysaccharides.

6. The peptide of claim 1 coupled to a detectable group.

7. The peptide of claim 6, wherein said detectable group is selected from the group consisting of fluorescent groups, radioactive groups, and enzymatic groups.

8. A solid support having an immunoglobulin binding peptide according to claim 1 immobilized thereon.

9. The solid support of claim 8, wherein said solid support is a bead, particle, membrane, semi-permeable membrane, capillary, microarray or multiple well plate.

10. The solid support of claim 8, wherein said solid support comprises an inorganic material.

11. The solid support of claim 8, wherein said solid support comprises an inorganic material selected from the group consisting of glass, alumina, silica, silicon, zirconia, magnetite, semiconductors, and combinations thereof.

12. The solid support of claim 8, wherein said solid support comprises an organic material.

13. The solid support of claim 8, wherein said solid support comprises an organic material selected from the group consisting of polysaccharides including agarose, dextran, cellulose, chitosan, polyacrylamide, polyacrylate, polystyrene, polyvinyl alcohol, and combinations thereof.

14. The solid support of claim 8, wherein said solid support is a polymer of an acrylate.

15. The solid support of claim 14, wherein said polymer is a methacrylate polymer.

16. The solid support of claim 14, wherein the polymer of an acrylate is hydroxylated polymethacrylate amino resin.

17. A method of binding an immunoglobulin, comprising:
   (a) providing a binding peptide according to claim 1;
   (b) contacting a composition containing an immunoglobulin to said binding peptide; and then
   (c) separating said binding peptide from said composition, with said immunoglobulin bound to said binding peptide.

18. The method of claim 17, wherein said peptide is coupled to a solid support, and wherein said separating step is carried out by separating said solid support from said composition.

19. The method of claim 18, further comprising the step of separating said immunoglobulin from said solid support.

20. The method of claim 18, wherein said solid support is a bead, particle, membrane, semi-permeable membranes, capillary, microarray or multiple well plate.

21. The method of claim 17, wherein said contacting step (b) is carried out in solution.

22. The method of claim 21, wherein said separating step (c) is carried out by fluorescence-activated cell sorting, membrane filtration, or mass spectrometry.

23. The method of claim 17, wherein said composition comprises blood or blood plasma.

24. The method of claim 17, wherein said composition comprises plasma fractions.

25. The method of claim 17, wherein said composition comprises ascites fluid, milk or colostrum.

26. The method of claim 17, wherein said composition comprises an aqueous cell culture containing said immunoglobulin.

27. The method of claim 17 wherein said immunoglobulin is a monoclonal antibody.

28. The method of claim 17, wherein said immunoglobulin is mammalian immunoglobulin.

29. The method of claim 17, wherein said immunoglobulin is selected from the group consisting of human, goat, bovine, mouse, rat, rabbit, monkey, horse, and sheep immunoglobulin.

30. The method of claim 17, wherein said immunoglobulin is selected from the group consisting of IgG, IgM, IgA, IgD and IgE.

31. The method of claim 17, wherein said immunoglobulin is a human IgG.

32. The method of claim 17, wherein said immunoglobulin is a humanized IgG.

33. The method of claim 17 wherein said immunoglobulin is a polyclonal antibody.

* * * * *

UNITED STATES PATENT AND TRADEMARK OFFICE
CERTIFICATE OF CORRECTION

PATENT NO. : 7,408,030 B2  Page 1 of 1
APPLICATION NO. : 11/035016
DATED : August 5, 2008
INVENTOR(S) : Carbonell et al.

It is certified that error appears in the above-identified patent and that said Letters Patent is hereby corrected as shown below:

On the Title Page:
Item 56, Other Publications: Please correct "alpha-lactalburnin,"
to read -- alpha-lactalburmin, --
in the following Reference: "Gurgel PV, et al., "Identification of peptide ligands generated by combinatorial chemistry that bind alpha-lactalburnin," Separation Science and Technology (2001), vol. 36(11), pp.2411-2431, Marcel Dekker, Inc., NY, NY."

Column 51, Claim 3, Line 31: Please correct "and diphenyiphosplilnyl."
to read -- and diphenylphosphinyl --

Signed and Sealed this

Fourth Day of November, 2008

JON W. DUDAS
*Director of the United States Patent and Trademark Office*

SEQUENCE LISTING

```
<160> NUMBER OF SEQ ID NOS: 41

<210> SEQ ID NO 1
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 1

His Tyr Gly Leu Gly Trp
1               5

<210> SEQ ID NO 2
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 2

His Glu Ile Leu Tyr Trp
1               5

<210> SEQ ID NO 3
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 3

His Phe Asp Lys Gly Phe
1               5

<210> SEQ ID NO 4
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 4

His Trp Arg Gly Trp Val
1               5

<210> SEQ ID NO 5
```

```
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 5

His Ala Asn Gly Phe Leu
1               5

<210> SEQ ID NO 6
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 6

His Arg Pro Leu Ile Phe
1               5

<210> SEQ ID NO 7
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 7

Trp His Trp Arg Lys Arg
1               5

<210> SEQ ID NO 8
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 8

Tyr Tyr Trp Leu His His
1               5

<210> SEQ ID NO 9
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 9

His Trp Gly Pro Thr Lys
1               5

<210> SEQ ID NO 10
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 10

His Trp Ile Asp Pro Leu
1               5

<210> SEQ ID NO 11
<211> LENGTH: 6
```

```
<212> TYPE: PRT
<213> ORGANISM: Artificial
<220> FEATURE:
<223> OTHER INFORMATION: Immunoglobulin binding peptide sequence

<400> SEQUENCE: 11

His Tyr Phe Lys Phe Asp
1               5

<210> SEQ ID NO 12
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 12

His Val His Tyr Tyr Trp
1               5

<210> SEQ ID NO 13
<211> LENGTH: 4
<212> TYPE: PRT
<213> ORGANISM: Artificial
<220> FEATURE:
<223> OTHER INFORMATION: Immunoglobulin binding peptide sequence

<400> SEQUENCE: 13

His Ile Trp Ala
1

<210> SEQ ID NO 14
<211> LENGTH: 4
<212> TYPE: PRT
<213> ORGANISM: Artificial
<220> FEATURE:
<223> OTHER INFORMATION: Immunoglobulin binding peptide sequence

<400> SEQUENCE: 14

Lys Gly Glu Ala
1

<210> SEQ ID NO 15
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 15

His Tyr Ile Asp Ala Lys
1               5

<210> SEQ ID NO 16
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 16

His Leu Lys Trp Tyr Ala
1               5

<210> SEQ ID NO 17
<211> LENGTH: 6
<212> TYPE: PRT
```

```
<213> ORGANISM: Artificial
<220> FEATURE:
<223> OTHER INFORMATION: Immunoglobulin binding peptide sequence

<400> SEQUENCE: 17

His Pro Trp Tyr Val Thr
1               5

<210> SEQ ID NO 18
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 18

His Asp Val Phe His Thr
1               5

<210> SEQ ID NO 19
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 19

His Ile Gln Leu Asp Gly
1               5

<210> SEQ ID NO 20
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 20

His Val Trp Gln Leu Lys
1               5

<210> SEQ ID NO 21
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 21

His Phe Arg Arg His Leu
1               5

<210> SEQ ID NO 22
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 22

Lys Leu Gln Trp Val His
1               5

<210> SEQ ID NO 23
<211> LENGTH: 6
<212> TYPE: PRT
<213> ORGANISM: Artificial
```

```
<220> FEATURE:
<223> OTHER INFORMATION: Immunoglobulin binding peptide sequence

<400> SEQUENCE: 23

Lys Arg Gly Phe Tyr Tyr
1               5

<210> SEQ ID NO 24
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 24

His Glu Thr Arg Phe Ser
1               5

<210> SEQ ID NO 25
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 25

His Trp Gly Thr Ile Ala
1               5

<210> SEQ ID NO 26
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 26

Ala Pro His His Leu Leu
1               5

<210> SEQ ID NO 27
<211> LENGTH: 6
<212> TYPE: PRT
<213> ORGANISM: Artificial
<220> FEATURE:
<223> OTHER INFORMATION: Immunoglobulin binding peptide sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 27

Lys Gly Xaa Gln Xaa Xaa
1               5

<210> SEQ ID NO 28
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 28

Pro Thr His Leu Phe Pro
```

-continued

```
<210> SEQ ID NO 29
<211> LENGTH: 6
<212> TYPE: PRT
<213> ORGANISM: Artificial
<220> FEATURE:
<223> OTHER INFORMATION: Immunoglobulin binding peptide sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 29

Lys Leu Gln Met Val Xaa
1               5

<210> SEQ ID NO 30
<211> LENGTH: 5
<212> TYPE: PRT
<213> ORGANISM: Artificial
<220> FEATURE:
<223> OTHER INFORMATION: Immunoglobulin binding peptide sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 30

Lys Xaa Xaa Gly Xaa
1               5

<210> SEQ ID NO 31
<211> LENGTH: 5
<212> TYPE: PRT
<213> ORGANISM: Artificial
<220> FEATURE:
<223> OTHER INFORMATION: Immunoglobulin binding peptide sequence
<220> FEATURE:
<221> NAME/KEY: misc_feature
<222> LOCATION: (3)..(5)
<223> OTHER INFORMATION: Xaa can be any naturally occurring amino acid

<400> SEQUENCE: 31

Lys Arg Xaa Xaa Xaa
1               5

<210> SEQ ID NO 32
<211> LENGTH: 5
<212> TYPE: PRT
<213> ORGANISM: Artificial
<220> FEATURE:
<223> OTHER INFORMATION: Immunoglobulin binding peptide sequence
<220> FEATURE:
<221> NAME/KEY: misc_feature
<222> LOCATION: (4)..(5)
<223> OTHER INFORMATION: Xaa can be any naturally occurring amino acid

<400> SEQUENCE: 32

Lys Gly Gly Xaa Xaa
1               5

<210> SEQ ID NO 33
<211> LENGTH: 13
<212> TYPE: PRT
<213> ORGANISM: Artificial
```

<220> FEATURE:
<223> OTHER INFORMATION: Immunoglobulin binding peptide sequence

<400> SEQUENCE: 33

Gly Phe Arg Lys Tyr Leu His Phe Arg Arg His Leu Leu
1               5                   10

<210> SEQ ID NO 34
<211> LENGTH: 6
<212> TYPE: PRT
<213> ORGANISM: Artificial
<220> FEATURE:
<223> OTHER INFORMATION: Immunoglobulin binding peptide sequence

<400> SEQUENCE: 34

His Arg Pro Lys Ile Phe
1               5

<210> SEQ ID NO 35
<211> LENGTH: 12
<212> TYPE: PRT
<213> ORGANISM: Artificial
<220> FEATURE:
<223> OTHER INFORMATION: Immunoglobulin binding peptide sequence

<400> SEQUENCE: 35

Glu Pro Ile His Arg Ser Thr Leu Thr Ala Leu Leu
1               5                   10

<210> SEQ ID NO 36
<211> LENGTH: 56
<212> TYPE: PRT
<213> ORGANISM: Artificial
<220> FEATURE:
<223> OTHER INFORMATION: Immunoglobulin binding peptide sequence

<400> SEQUENCE: 36

Gly Phe Arg Lys Tyr Leu His Phe Arg Arg His Leu Leu Gly Phe Arg
1               5                   10                  15

Lys Tyr Leu His Phe Arg Arg His Leu Leu Gly Phe Arg Lys Tyr Leu
            20                  25                  30

His Phe Arg Arg His Leu Leu Gly Phe Arg Lys Tyr Leu His Phe Arg
        35                  40                  45

Arg His Leu Leu Lys Lys Lys Gly
    50                  55

<210> SEQ ID NO 37
<211> LENGTH: 15
<212> TYPE: PRT
<213> ORGANISM: Artificial
<220> FEATURE:
<223> OTHER INFORMATION: Immunoglobulin binding peptide sequence

<400> SEQUENCE: 37

Val Arg Leu Gly Trp Leu Leu Ala Pro Ala Asp Leu Asp Ala Arg
1               5                   10                  15

<210> SEQ ID NO 38
<211> LENGTH: 68
<212> TYPE: PRT
<213> ORGANISM: Artificial
<220> FEATURE:
<223> OTHER INFORMATION: Immunoglobulin binding peptide sequence

<400> SEQUENCE: 38

```
Val Arg Leu Gly Trp Leu Leu Ala Pro Ala Asp Leu Asp Ala Arg Val
1               5                   10                  15

Arg Leu Gly Trp Leu Leu Ala Pro Ala Asp Leu Asp Ala Arg Val Arg
                20                  25                  30

Leu Gly Trp Leu Leu Ala Pro Ala Asp Leu Asp Ala Arg Val Arg Leu
            35                  40                  45

Gly Trp Leu Leu Ala Pro Ala Asp Leu Asp Ala Arg Lys Arg Gly Lys
    50                  55                  60

Arg Gly Lys Gly
65

<210> SEQ ID NO 39
<211> LENGTH: 16
<212> TYPE: PRT
<213> ORGANISM: Artificial
<220> FEATURE:
<223> OTHER INFORMATION: Immunoglobulin binding peptide sequence

<400> SEQUENCE: 39

Arg Thr Tyr Arg Thr Tyr Arg Thr Tyr Arg Thr Tyr Lys Lys Lys Gly
1               5                   10                  15

<210> SEQ ID NO 40
<211> LENGTH: 8
<212> TYPE: PRT
<213> ORGANISM: Artificial
<220> FEATURE:
<223> OTHER INFORMATION: Immunoglobulin binding peptide sequence

<400> SEQUENCE: 40

Lys Ala Pro Thr Ile Val Gly Tyr
1               5

<210> SEQ ID NO 41
<211> LENGTH: 6
<212> TYPE: PRT
<213> ORGANISM: Artificial
<220> FEATURE:
<223> OTHER INFORMATION: Immunoglobulin binding peptide sequence
<220> FEATURE:
<221> NAME/KEY: MISC_FEATURE
<222> LOCATION: (1)..(1)
<223> OTHER INFORMATION: Xaa can be histidine or tyrosine and may be
      optionally bonded to a capping group Z
<220> FEATURE:
<221> NAME/KEY: MISC_FEATURE
<222> LOCATION: (2)..(2)
<223> OTHER INFORMATION: Xaa can be tryptophan, phenylalanine,
      tyrosine, or valine
<220> FEATURE:
<221> NAME/KEY: MISC_FEATURE
<222> LOCATION: (3)..(3)
<223> OTHER INFORMATION: Xaa can be arginine, histidine, phenylalanine,
      or tryptophan
<220> FEATURE:
<221> NAME/KEY: MISC_FEATURE
<222> LOCATION: (4)..(4)
<223> OTHER INFORMATION: Xaa can be glycine, tyrosine, arginine,
      lysine, or leucine
<220> FEATURE:
<221> NAME/KEY: MISC_FEATURE
<222> LOCATION: (5)..(5)
<223> OTHER INFORMATION: Xaa can be tryptophan, phenylalanine,
      arginine, histidine, or tyrosine
<220> FEATURE:
<221> NAME/KEY: MISC_FEATURE
<222> LOCATION: (6)..(6)
<223> OTHER INFORMATION: Xaa can be valine, tryptophan, leucine,
      aspartic acid, or histidine, and may be optionally bonded to
      linking group X
```

```
<400> SEQUENCE: 41

Xaa Xaa Xaa Xaa Xaa Xaa
1               5
```